(12) United States Patent
Klein et al.

(10) Patent No.: US 9,034,883 B2
(45) Date of Patent: *May 19, 2015

(54) VASOPROTECTIVE AND CARDIOPROTECTIVE ANTIDIABETIC THERAPY

(75) Inventors: Thomas Klein, Radolfzell (DE); Andreas Daiber, Scheesel (DE); Odd-Eric Johansen, Hovik (NO); Michael Mark, Biberach an der Riss (DE); Sanjaykumar Patel, Bracknell (GB); Hans-Juergen Woerle, Munich (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/295,174

(22) Filed: Nov. 14, 2011

(65) Prior Publication Data

US 2012/0121530 A1 May 17, 2012

Related U.S. Application Data

(60) Provisional application No. 61/492,391, filed on Jun. 2, 2011, provisional application No. 61/421,400, filed on Dec. 9, 2010, provisional application No. 61/415,545, filed on Nov. 19, 2010.

(30) Foreign Application Priority Data

| Nov. 15, 2010 | (EP) | 10191261 |
| May 31, 2011 | (EP) | 11168317 |
| Jun. 22, 2011 | (EP) | 11170992 |

(51) Int. Cl.

| A61K 31/52 | (2006.01) |
| C07D 473/12 | (2006.01) |
| A61K 31/519 | (2006.01) |
| C07D 473/06 | (2006.01) |
| A61K 31/397 | (2006.01) |
| A61K 31/522 | (2006.01) |
| A61K 31/5377 | (2006.01) |
| A61K 31/616 | (2006.01) |
| A61K 31/727 | (2006.01) |
| A61K 31/785 | (2006.01) |
| A61K 38/26 | (2006.01) |
| A61K 38/28 | (2006.01) |
| A61K 45/06 | (2006.01) |

(52) U.S. Cl.
CPC ............ *A61K 31/519* (2013.01); *C07D 473/06* (2013.01); *C07D 473/12* (2013.01); *A61K 31/397* (2013.01); *A61K 31/522* (2013.01); *A61K 31/5377* (2013.01); *A61K 31/616* (2013.01); *A61K 31/727* (2013.01); *A61K 31/785* (2013.01); *A61K 38/26* (2013.01); *A61K 38/28* (2013.01); *A61K 45/06* (2013.01)

(58) Field of Classification Search
CPC .......................... C07D 473/06; C07D 473/12
USPC ..................... 514/263.21; 544/268
See application file for complete search history.

(56) References Cited

U.S. PATENT DOCUMENTS

| 2,056,046 A | 9/1936 | Fourneau |
| 2,375,138 A | 5/1945 | Salvin |
| 2,629,736 A | 2/1953 | Krimmel |
| 2,730,544 A | 1/1956 | Sahyun |
| 2,750,387 A | 6/1956 | Krimmel |
| 2,928,833 A | 3/1960 | Leake et al. |
| 3,174,901 A | 3/1965 | Sterne |
| 3,236,891 A | 2/1966 | Seemuller |
| 3,454,635 A | 7/1969 | Muth |
| 3,673,241 A | 6/1972 | Marxer |
| 3,925,357 A | 12/1975 | Okada et al. |
| 4,005,208 A | 1/1977 | Bender et al. |
| 4,061,753 A | 12/1977 | Bodor et al. |
| 4,382,091 A | 5/1983 | Benjamin et al. |
| 4,599,338 A | 7/1986 | Regnier et al. |
| 4,639,436 A | 1/1987 | Junge et al. |
| 4,687,777 A | 8/1987 | Meguro et al. |
| 4,743,450 A | 5/1988 | Harris et al. |
| 4,816,455 A | 3/1989 | Schickaneder et al. |
| 4,873,330 A | 10/1989 | Lindholm |
| 4,968,672 A | 11/1990 | Jacobson et al. |
| 5,041,448 A | 8/1991 | Janssens et al. |

(Continued)

FOREIGN PATENT DOCUMENTS

| AU | 2003280680 A1 | 6/2004 |
| AU | 2009224546 A1 | 9/2009 |

(Continued)

OTHER PUBLICATIONS

Heise et al., Treatment with BI 1356, a Novel and Potent DPP-IV Inhibitor, Significantly Reduces Glucose Excursions after an oGTT in Patients with Type 2 Diabetes, Jun. 2007, Diabetes, vol. 56 supp. 1, p. A156.*

Ferreira et al., Effects of Sitagliptin Treatment on Dysmetabolism, Inflammation, and Oxidative Stress in an Animal Model of Type 2 Diabetes (ZDF Rat), 2010, Mediators of Inflammation, vol. 2010, pp. 1-11.*

He, Y. L. et al., "Bioequivalence of Vildagliptin/Metformin Combination Tablets and Coadministration of Vildagliptin and Metformin as Free Combination in Healthy Subjects". J. Clinical Pharmacology, 2007, vol. 47, No. 9, Abstracts of the 36th Annual Meeting of the American College of Clinical Pharmacology, San Francisco, CA, Abstract 116, p. 1210.

(Continued)

*Primary Examiner* — Ali Soroush
(74) *Attorney, Agent, or Firm* — Michael P. Morris; David L. Kershner

(57) ABSTRACT

The present invention relates to certain DPP-4 inhibitors for treating and/or preventing oxidative stress, vascular stress and/or endothelial dysfunction as well as to the use of such DPP-4 inhibitors in treatment and/or prevention of diabetic or non-diabetic patients, including patient groups at risk of cardiovascular and/or renal disease.

5 Claims, 11 Drawing Sheets

(56) References Cited

U.S. PATENT DOCUMENTS

| | | |
|---|---|---|
| 5,051,517 A | 9/1991 | Findeisen et al. |
| 5,084,460 A | 1/1992 | Munson, Jr. et al. |
| 5,130,244 A | 7/1992 | Nishimaki et al. |
| 5,164,526 A | 11/1992 | Macher |
| 5,219,870 A | 6/1993 | Kim |
| 5,223,499 A | 6/1993 | Greenlee et al. |
| 5,234,897 A | 8/1993 | Findeisen et al. |
| 5,258,380 A | 11/1993 | Janssens et al. |
| 5,266,555 A | 11/1993 | Findeisen et al. |
| 5,273,995 A | 12/1993 | Roth |
| 5,284,967 A | 2/1994 | Macher |
| 5,300,298 A | 4/1994 | LaNoue |
| 5,329,025 A | 7/1994 | Wong et al. |
| 5,332,744 A | 7/1994 | Chakravarty et al. |
| 5,389,642 A | 2/1995 | Dorsch et al. |
| 5,399,578 A | 3/1995 | Buhlmayer et al. |
| 5,407,929 A | 4/1995 | Takahashi et al. |
| 5,461,066 A | 10/1995 | Gericke et al. |
| 5,470,579 A | 11/1995 | Bonte et al. |
| 5,591,762 A | 1/1997 | Hauel et al. |
| 5,594,003 A | 1/1997 | Hauel et al. |
| 5,602,127 A | 2/1997 | Hauel et al. |
| 5,614,519 A | 3/1997 | Hauel et al. |
| 5,719,279 A | 2/1998 | Kufner-Muhl et al. |
| 5,728,849 A | 3/1998 | Bouchard et al. |
| 5,753,635 A | 5/1998 | Buckman et al. |
| 5,830,908 A | 11/1998 | Grunenberg et al. |
| 5,879,708 A | 3/1999 | Makino et al. |
| 5,958,951 A | 9/1999 | Ahrndt et al. |
| 5,965,555 A | 10/1999 | Gebert et al. |
| 5,965,592 A | 10/1999 | Buhlmayer et al. |
| 6,011,049 A | 1/2000 | Whitcomb |
| 6,107,302 A | 8/2000 | Carter et al. |
| 6,166,063 A | 12/2000 | Villhauer |
| 6,248,758 B1 | 6/2001 | Klokkers et al. |
| 6,303,661 B1 | 10/2001 | Demuth et al. |
| 6,342,601 B1 | 1/2002 | Bantick et al. |
| 6,372,940 B1 | 4/2002 | Cavazza |
| 6,548,481 B1 | 4/2003 | Demuth et al. |
| 6,579,868 B1 | 6/2003 | Asano et al. |
| 6,727,261 B2 | 4/2004 | Gobbi et al. |
| 6,784,195 B2 | 8/2004 | Hale et al. |
| 6,821,978 B2 | 11/2004 | Chackalamannil et al. |
| 6,869,947 B2 | 3/2005 | Kanstrup et al. |
| 6,995,183 B2 | 2/2006 | Hamann et al. |
| 7,060,722 B2 | 6/2006 | Kitajima et al. |
| 7,074,794 B2 | 7/2006 | Kitajima et al. |
| 7,074,798 B2 | 7/2006 | Yoshikawa et al. |
| 7,074,923 B2 | 7/2006 | Dahanukar et al. |
| 7,109,192 B2 | 9/2006 | Hauel et al. |
| 7,179,809 B2 | 2/2007 | Eckhardt et al. |
| 7,183,280 B2 | 2/2007 | Himmelsbach et al. |
| 7,192,952 B2 | 3/2007 | Kanstrup et al. |
| 7,217,711 B2 | 5/2007 | Eckhardt et al. |
| 7,235,538 B2 | 6/2007 | Kanstrup et al. |
| 7,247,478 B2 | 7/2007 | Eberhardt et al. |
| 7,291,642 B2 | 11/2007 | Kauffmann-Hefner et al. |
| 7,361,687 B2 | 4/2008 | Barth et al. |
| 7,393,847 B2 | 7/2008 | Eckhardt et al. |
| 7,407,955 B2 | 8/2008 | Himmelsbach et al. |
| 7,407,995 B2 | 8/2008 | Ok et al. |
| 7,432,262 B2 | 10/2008 | Eckhardt et al. |
| 7,439,370 B2 | 10/2008 | Eckhardt |
| 7,470,716 B2 | 12/2008 | Eckhardt et al. |
| 7,476,671 B2 | 1/2009 | Eckhardt et al. |
| 7,482,337 B2 | 1/2009 | Himmelsbach et al. |
| 7,495,002 B2 | 2/2009 | Langkopf et al. |
| 7,495,003 B2 | 2/2009 | Eckhardt et al. |
| 7,495,005 B2 | 2/2009 | Himmelsbach et al. |
| 7,501,426 B2 | 3/2009 | Himmelsbach et al. |
| 7,550,455 B2 | 6/2009 | Himmelsbach et al. |
| 7,560,450 B2 | 7/2009 | Eckhardt et al. |
| 7,566,707 B2 | 7/2009 | Eckhardt et al. |
| 7,569,574 B2 | 8/2009 | Maier et al. |
| 7,579,449 B2 | 8/2009 | Eckhardt et al. |
| 7,610,153 B2 | 10/2009 | Carter, Jr. et al. |
| 7,645,763 B2 | 1/2010 | Himmelsbach et al. |
| 7,718,666 B2 | 5/2010 | Boehringer et al. |
| 7,799,782 B2 | 9/2010 | Munson et al. |
| 7,820,815 B2 | 10/2010 | Pfrengle et al. |
| 7,838,529 B2 | 11/2010 | Himmelsbach et al. |
| 8,039,477 B2 | 10/2011 | Hendrix et al. |
| 8,071,583 B2 | 12/2011 | Himmelsbach |
| 8,106,060 B2 | 1/2012 | Pfrengle et al. |
| 8,119,648 B2 | 2/2012 | Himmelsbach et al. |
| 8,158,633 B2 | 4/2012 | Hendrix et al. |
| 8,178,541 B2 | 5/2012 | Himmelsbach et al. |
| 8,232,281 B2 | 7/2012 | Dugi et al. |
| 8,679,520 B2 | 3/2014 | Horres et al. |
| 8,785,455 B2 | 7/2014 | Hotter et al. |
| 2001/0020006 A1 | 9/2001 | Demuth et al. |
| 2001/0051646 A1 | 12/2001 | Demuth et al. |
| 2002/0019411 A1 | 2/2002 | Robl et al. |
| 2002/0137903 A1 | 9/2002 | Ellsworth et al. |
| 2002/0161001 A1 | 10/2002 | Kanstrup et al. |
| 2002/0169174 A1 | 11/2002 | Chackalamannil et al. |
| 2002/0198205 A1 | 12/2002 | Himmelsbach et al. |
| 2003/0078269 A1 | 4/2003 | Pearson et al. |
| 2003/0100563 A1 | 5/2003 | Edmondson et al. |
| 2003/0105077 A1 | 6/2003 | Kanstrup et al. |
| 2003/0114390 A1 | 6/2003 | Washburn et al. |
| 2003/0130313 A1 | 7/2003 | Fujino et al. |
| 2003/0149071 A1 | 8/2003 | Gobbi et al. |
| 2003/0166578 A1 | 9/2003 | Arch et al. |
| 2003/0199528 A1 | 10/2003 | Kanstrup et al. |
| 2003/0224043 A1 | 12/2003 | Appel et al. |
| 2003/0232987 A1 | 12/2003 | Dahanukar et al. |
| 2003/0236272 A1 | 12/2003 | Carr |
| 2004/0023981 A1 | 2/2004 | Ren et al. |
| 2004/0034014 A1 | 2/2004 | Kanstrup et al. |
| 2004/0063725 A1 | 4/2004 | Barth et al. |
| 2004/0077645 A1 | 4/2004 | Himmelsbach et al. |
| 2004/0082570 A1 | 4/2004 | Yoshikawa et al. |
| 2004/0087587 A1 | 5/2004 | Himmelsbach et al. |
| 2004/0097510 A1 | 5/2004 | Himmelsbach et al. |
| 2004/0116328 A1 | 6/2004 | Yoshikawa et al. |
| 2004/0122048 A1 | 6/2004 | Benjamin et al. |
| 2004/0122228 A1 | 6/2004 | Maier et al. |
| 2004/0126358 A1 | 7/2004 | Warne et al. |
| 2004/0138214 A1 | 7/2004 | Himmelsbach et al. |
| 2004/0138215 A1 | 7/2004 | Eckhardt et al. |
| 2004/0152720 A1 | 8/2004 | Hartig et al. |
| 2004/0166125 A1 | 8/2004 | Himmelsbach et al. |
| 2004/0171836 A1 | 9/2004 | Fujino et al. |
| 2004/0180925 A1 | 9/2004 | Matsuno et al. |
| 2004/0259903 A1 | 12/2004 | Boehringer et al. |
| 2005/0020574 A1 | 1/2005 | Hauel et al. |
| 2005/0026921 A1 | 2/2005 | Eckhardt et al. |
| 2005/0032804 A1 | 2/2005 | Cypes et al. |
| 2005/0065145 A1 | 3/2005 | Cao et al. |
| 2005/0070562 A1 | 3/2005 | Jones et al. |
| 2005/0070594 A1 | 3/2005 | Kauschke et al. |
| 2005/0130985 A1 | 6/2005 | Himmelsbach et al. |
| 2005/0143377 A1 | 6/2005 | Himmelsbach et al. |
| 2005/0171093 A1 | 8/2005 | Eckhardt et al. |
| 2005/0187227 A1 | 8/2005 | Himmelsbach et al. |
| 2005/0203095 A1 | 9/2005 | Eckhardt et al. |
| 2005/0234108 A1 | 10/2005 | Himmelsbach et al. |
| 2005/0234235 A1 | 10/2005 | Eckhardt et al. |
| 2005/0239778 A1 | 10/2005 | Konetzki et al. |
| 2005/0256310 A1 | 11/2005 | Hulin et al. |
| 2005/0261271 A1 | 11/2005 | Feng et al. |
| 2005/0261352 A1 | 11/2005 | Eckhardt |
| 2005/0266080 A1 | 12/2005 | Desai et al. |
| 2005/0276794 A1 | 12/2005 | Papas et al. |
| 2006/0004074 A1 | 1/2006 | Eckhardt et al. |
| 2006/0034922 A1 | 2/2006 | Cheng et al. |
| 2006/0039974 A1 | 2/2006 | Akiyama et al. |
| 2006/0047125 A1 | 3/2006 | Leonardi et al. |
| 2006/0058323 A1 | 3/2006 | Eckhardt et al. |
| 2006/0063787 A1 | 3/2006 | Yoshikawa et al. |
| 2006/0074058 A1* | 4/2006 | Holmes et al. ................ 514/171 |
| 2006/0079541 A1 | 4/2006 | Langkopf et al. |
| 2006/0094722 A1 | 5/2006 | Yasuda et al. |

(56) References Cited

U.S. PATENT DOCUMENTS

| | | |
|---|---|---|
| 2006/0100199 A1 | 5/2006 | Yoshikawa et al. |
| 2006/0106035 A1 | 5/2006 | Hendrix et al. |
| 2006/0111372 A1 | 5/2006 | Hendrix et al. |
| 2006/0111379 A1 | 5/2006 | Guillemont et al. |
| 2006/0134206 A1 | 6/2006 | Iyer et al. |
| 2006/0142310 A1 | 6/2006 | Pfrengle et al. |
| 2006/0154866 A1 | 7/2006 | Chu et al. |
| 2006/0159746 A1 | 7/2006 | Troup et al. |
| 2006/0173056 A1 | 8/2006 | Kitajima et al. |
| 2006/0205711 A1 | 9/2006 | Himmelsbach et al. |
| 2006/0205943 A1 | 9/2006 | Dahanukar et al. |
| 2006/0247226 A1 | 11/2006 | Himmelsbach et al. |
| 2006/0270668 A1 | 11/2006 | Chew et al. |
| 2006/0270701 A1 | 11/2006 | Kroth et al. |
| 2007/0027168 A1 | 2/2007 | Pfrengle et al. |
| 2007/0060530 A1 | 3/2007 | Christopher et al. |
| 2007/0072803 A1 | 3/2007 | Chu et al. |
| 2007/0072810 A1 | 3/2007 | Asakawa |
| 2007/0088038 A1 | 4/2007 | Eckhardt et al. |
| 2007/0093659 A1 | 4/2007 | Bonfanti et al. |
| 2007/0142383 A1 | 6/2007 | Eckhardt et al. |
| 2007/0185091 A1 | 8/2007 | Himmelsbach et al. |
| 2007/0196472 A1 | 8/2007 | Kiel et al. |
| 2007/0197522 A1 | 8/2007 | Edwards et al. |
| 2007/0219178 A1 | 9/2007 | Muramoto |
| 2007/0259900 A1 | 11/2007 | Sieger et al. |
| 2007/0259925 A1 | 11/2007 | Boehringer et al. |
| 2007/0259927 A1 | 11/2007 | Suzuki et al. |
| 2007/0281940 A1 | 12/2007 | Dugi et al. |
| 2007/0299076 A1 | 12/2007 | Piotrowski et al. |
| 2008/0039427 A1 | 2/2008 | Ray et al. |
| 2008/0107731 A1 | 5/2008 | Kohlrausch et al. |
| 2008/0108816 A1 | 5/2008 | Zutter |
| 2008/0249089 A1 | 10/2008 | Himmelsbach et al. |
| 2008/0255159 A1 | 10/2008 | Himmelsbach et al. |
| 2008/0312243 A1 | 12/2008 | Eckhardt et al. |
| 2008/0318922 A1 | 12/2008 | Nakahira et al. |
| 2009/0023920 A1 | 1/2009 | Eckhardt |
| 2009/0088408 A1 | 4/2009 | Meade et al. |
| 2009/0088569 A1 | 4/2009 | Eckhardt et al. |
| 2009/0093457 A1 | 4/2009 | Himmelsbach et al. |
| 2009/0131432 A1 | 5/2009 | Himmelsbach et al. |
| 2009/0136596 A1 | 5/2009 | Munson et al. |
| 2009/0137801 A1 | 5/2009 | Himmelsbach et al. |
| 2009/0149483 A1 | 6/2009 | Nakahira et al. |
| 2009/0186086 A1 | 7/2009 | Shankar et al. |
| 2009/0192314 A1 | 7/2009 | Pfrengle et al. |
| 2009/0297470 A1 | 12/2009 | Franz |
| 2009/0301105 A1 | 12/2009 | Loerting |
| 2009/0325926 A1 | 12/2009 | Himmelsbach |
| 2010/0074950 A1 | 3/2010 | Sesha |
| 2010/0092551 A1 | 4/2010 | Nakamura et al. |
| 2010/0173916 A1 | 7/2010 | Himmelsbach et al. |
| 2010/0179191 A1 | 7/2010 | Himmelsbach et al. |
| 2010/0183531 A1 | 7/2010 | Johncock et al. |
| 2010/0204250 A1 | 8/2010 | Himmelsbach et al. |
| 2010/0209506 A1 | 8/2010 | Eisenreich |
| 2010/0310664 A1 | 12/2010 | Watson et al. |
| 2011/0009391 A1 | 1/2011 | Braun et al. |
| 2011/0046076 A1 | 2/2011 | Eickelmann et al. |
| 2011/0065731 A1 | 3/2011 | Dugi et al. |
| 2011/0092510 A1 | 4/2011 | Klein et al. |
| 2011/0098240 A1 | 4/2011 | Dugi et al. |
| 2011/0112069 A1 | 5/2011 | Himmelsbach et al. |
| 2011/0144083 A1 | 6/2011 | Himmelsbach et al. |
| 2011/0144095 A1 | 6/2011 | Himmelsbach et al. |
| 2011/0190322 A1 | 8/2011 | Klein et al. |
| 2011/0195917 A1 | 8/2011 | Dugi et al. |
| 2011/0206766 A1 | 8/2011 | Friedl et al. |
| 2011/0263493 A1 | 10/2011 | Dugi et al. |
| 2011/0263617 A1 | 10/2011 | Mark et al. |
| 2011/0275561 A1 | 11/2011 | Graefe-Mody et al. |
| 2011/0301182 A1 | 12/2011 | Dugi |
| 2012/0003313 A1 | 1/2012 | Kohlrausch et al. |
| 2012/0035158 A1 | 2/2012 | Himmelsbach et al. |
| 2012/0040982 A1 | 2/2012 | Himmelsbach et al. |
| 2012/0053173 A1 | 3/2012 | Banno et al. |
| 2012/0094894 A1 | 4/2012 | Graefe-Mody et al. |
| 2012/0107398 A1 | 5/2012 | Schneider et al. |
| 2012/0121530 A1 | 5/2012 | Klein et al. |
| 2012/0122776 A1 | 5/2012 | Graefe-Mody et al. |
| 2012/0129874 A1 | 5/2012 | Sieger et al. |
| 2012/0142712 A1 | 6/2012 | Pfrengle et al. |
| 2012/0165251 A1 | 6/2012 | Klein et al. |
| 2012/0208831 A1 | 8/2012 | Himmelsbach et al. |
| 2012/0219622 A1 | 8/2012 | Kohlrausch et al. |
| 2012/0219623 A1 | 8/2012 | Meinicke |
| 2012/0252782 A1 | 10/2012 | Himmelsbach et al. |
| 2012/0252783 A1 | 10/2012 | Himmelsbach et al. |
| 2012/0296091 A1 | 11/2012 | Sieger et al. |
| 2013/0122089 A1 | 5/2013 | Kohlrausch et al. |
| 2013/0172244 A1 | 7/2013 | Klein et al. |
| 2013/0184204 A1 | 7/2013 | Pfrengle et al. |
| 2013/0196898 A1 | 8/2013 | Dugi et al. |
| 2013/0236543 A1 | 9/2013 | Ito et al. |

FOREIGN PATENT DOCUMENTS

| | | |
|---|---|---|
| CA | 1123437 A1 | 5/1982 |
| CA | 2136288 A1 | 5/1995 |
| CA | 2418656 A1 | 2/2002 |
| CA | 2496249 A1 | 3/2004 |
| CA | 2496325 A1 | 3/2004 |
| CA | 2498423 A1 | 4/2004 |
| CA | 2505389 A1 | 5/2004 |
| CA | 2508233 A1 | 6/2004 |
| CA | 2529729 A1 | 12/2004 |
| CA | 2543074 A1 | 6/2005 |
| CA | 2555050 A1 | 9/2005 |
| CA | 2556064 A1 | 9/2005 |
| CA | 2558067 A1 | 10/2005 |
| CA | 2561210 A1 | 10/2005 |
| CA | 2562859 A1 | 11/2005 |
| CA | 2576294 A1 | 3/2006 |
| CA | 2590912 A1 | 6/2006 |
| CA | 2651019 A1 | 11/2007 |
| CA | 2651089 A1 | 11/2007 |
| CN | 101234105 A | 8/2008 |
| DE | 2205815 A1 | 8/1973 |
| DE | 2758025 A1 | 7/1979 |
| DE | 10109021 A1 | 9/2002 |
| DE | 10117803 A1 | 10/2002 |
| DE | 10238243 A1 | 3/2004 |
| DE | 102004019540 A1 | 11/2005 |
| DE | 102004024454 A1 | 12/2005 |
| DE | 102004044221 A1 | 3/2006 |
| DE | 102004054054 A1 | 5/2006 |
| EP | 0023032 A1 | 1/1981 |
| EP | 0149578 A2 | 7/1985 |
| EP | 0223403 A2 | 5/1987 |
| EP | 0237608 A1 | 9/1987 |
| EP | 0248634 A2 | 12/1987 |
| EP | 0389282 A2 | 9/1990 |
| EP | 0399285 A1 | 11/1990 |
| EP | 0400974 A2 | 12/1990 |
| EP | 409281 A1 | 1/1991 |
| EP | 0412358 A1 | 2/1991 |
| EP | 443983 A1 | 8/1991 |
| EP | 0475482 A1 | 3/1992 |
| EP | 0524482 A1 | 1/1993 |
| EP | 0657454 A1 | 6/1995 |
| EP | 0775704 A1 | 5/1997 |
| EP | 0950658 A1 | 10/1999 |
| EP | 1054012 A1 | 11/2000 |
| EP | 1066265 A1 | 1/2001 |
| EP | 1333033 | 8/2003 |
| EP | 1338595 A2 | 8/2003 |
| EP | 1406873 A2 | 4/2004 |
| EP | 1500403 A1 | 1/2005 |
| EP | 1514552 A1 | 3/2005 |
| EP | 1535906 A1 | 6/2005 |
| EP | 1537880 A1 | 6/2005 |
| EP | 1557165 A1 | 7/2005 |
| EP | 1586571 A1 | 10/2005 |

(56) References Cited

FOREIGN PATENT DOCUMENTS

| | | |
|---|---|---|
| EP | 1743655 A1 | 1/2007 |
| EP | 1760076 | 3/2007 |
| EP | 1829877 A1 | 9/2007 |
| EP | 1852108 A1 | 11/2007 |
| EP | 1897892 A2 | 3/2008 |
| EP | 2143443 A1 | 1/2010 |
| ES | 385302 A1 | 4/1973 |
| ES | 2256797 T3 | 7/2006 |
| ES | 2263057 T3 | 12/2006 |
| FR | 2707641 A1 | 1/1995 |
| GB | 2084580 A | 4/1982 |
| HU | 9003243 | 5/1990 |
| HU | 9902308 A2 | 7/2000 |
| JP | S374895 A | 6/1962 |
| JP | 770120 | 3/1995 |
| JP | 8333339 | 12/1996 |
| JP | 11193270 | 7/1999 |
| JP | 2000502684 A | 3/2000 |
| JP | 2001213770 A | 8/2001 |
| JP | 2001278812 A | 10/2001 |
| JP | 2002348279 A | 12/2002 |
| JP | 2003286287 A | 10/2003 |
| JP | 2003300977 A | 10/2003 |
| JP | 2004161749 A | 6/2004 |
| JP | 2006045156 A | 2/2006 |
| JP | 2010053576 A | 3/2010 |
| JP | 2010524580 A | 7/2010 |
| KR | 20070111099 A | 11/2007 |
| WO | 9107945 A1 | 6/1991 |
| WO | 9205175 A1 | 4/1992 |
| WO | 9219227 A2 | 11/1992 |
| WO | 9402150 A1 | 2/1994 |
| WO | 9403456 A1 | 2/1994 |
| WO | 9532178 A1 | 11/1995 |
| WO | 9609045 A1 | 3/1996 |
| WO | 9611917 A1 | 4/1996 |
| WO | 9636638 A1 | 11/1996 |
| WO | 9723447 A1 | 7/1997 |
| WO | 9723473 A1 | 7/1997 |
| WO | 9746526 A1 | 12/1997 |
| WO | 9807725 | 2/1998 |
| WO | 9811893 | 3/1998 |
| WO | 9818770 A1 | 5/1998 |
| WO | 9822464 A1 | 5/1998 |
| WO | 9828007 A1 | 7/1998 |
| WO | 9840069 A2 | 9/1998 |
| WO | 9846082 A1 | 10/1998 |
| WO | 9856406 A1 | 12/1998 |
| WO | 9929695 A1 | 6/1999 |
| WO | 9950248 A1 | 10/1999 |
| WO | 9956561 A1 | 11/1999 |
| WO | 9967279 A1 | 12/1999 |
| WO | 0073307 A2 | 12/2000 |
| WO | 0107441 A1 | 2/2001 |
| WO | 01040180 A2 | 6/2001 |
| WO | 0151919 | 7/2001 |
| WO | 0152825 | 7/2001 |
| WO | 0152825 A2 | 7/2001 |
| WO | 0152852 A1 | 7/2001 |
| WO | 0166548 A1 | 9/2001 |
| WO | 0168646 A1 | 9/2001 |
| WO | 0172290 A2 | 10/2001 |
| WO | 0177110 A1 | 10/2001 |
| WO | 0196301 A1 | 12/2001 |
| WO | 0197808 A1 | 12/2001 |
| WO | 0202560 A2 | 1/2002 |
| WO | 0214271 A1 | 2/2002 |
| WO | 0224698 A1 | 3/2002 |
| WO | 02053516 A2 | 7/2002 |
| WO | 02068420 A1 | 9/2002 |
| WO | 03000241 A2 | 1/2003 |
| WO | 03002531 A2 | 1/2003 |
| WO | 03004496 A1 | 1/2003 |
| WO | 03024965 A2 | 3/2003 |
| WO | 03033686 A2 | 4/2003 |
| WO | 03034944 A1 | 5/2003 |
| WO | 03037327 A1 | 5/2003 |
| WO | 03053929 A1 | 7/2003 |
| WO | 03055881 A1 | 7/2003 |
| WO | 03057200 A2 | 7/2003 |
| WO | 03064454 A1 | 8/2003 |
| WO | 03088900 A2 | 10/2003 |
| WO | 03094909 A2 | 11/2003 |
| WO | 03099279 A1 | 12/2003 |
| WO | 03099836 A1 | 12/2003 |
| WO | 03103629 A1 | 12/2003 |
| WO | 03104229 A1 | 12/2003 |
| WO | 03106428 A1 | 12/2003 |
| WO | 2004002924 A1 | 1/2004 |
| WO | 2004011416 A1 | 2/2004 |
| WO | 2004016587 A1 | 2/2004 |
| WO | 2004018467 A2 | 3/2004 |
| WO | 2004018468 A2 | 3/2004 |
| WO | 2004018469 A1 | 3/2004 |
| WO | 2004028524 A1 | 4/2004 |
| WO | 2004033455 A1 | 4/2004 |
| WO | 2004035575 A1 | 4/2004 |
| WO | 2004041820 A1 | 5/2004 |
| WO | 2004046148 A1 | 6/2004 |
| WO | 2004048379 A1 | 6/2004 |
| WO | 2004050658 A1 | 6/2004 |
| WO | 2004052362 A1 | 6/2004 |
| WO | 2004058233 A1 | 7/2004 |
| WO | 2004062689 A1 | 7/2004 |
| WO | 2004065380 A1 | 8/2004 |
| WO | 2004074246 A2 | 9/2004 |
| WO | 2004081006 A1 | 9/2004 |
| WO | 2004082402 A1 | 9/2004 |
| WO | 2004096806 A1 | 11/2004 |
| WO | 2004096811 A1 | 11/2004 |
| WO | 2004106279 A2 | 12/2004 |
| WO | 2004108730 A1 | 12/2004 |
| WO | 2004111051 A1 | 12/2004 |
| WO | 2005000846 A1 | 1/2005 |
| WO | 2005000848 A1 | 1/2005 |
| WO | 2005007647 A1 | 1/2005 |
| WO | 2005007658 A2 | 1/2005 |
| WO | 2005012288 A1 | 2/2005 |
| WO | 2005023179 A2 | 3/2005 |
| WO | 2005049022 A2 | 6/2005 |
| WO | 2005051950 A1 | 6/2005 |
| WO | 2005058901 A1 | 6/2005 |
| WO | 2005061489 A1 | 7/2005 |
| WO | 2005063750 A1 | 7/2005 |
| WO | 2005082906 A1 | 9/2005 |
| WO | 2005085246 A1 | 9/2005 |
| WO | 2005092870 A1 | 10/2005 |
| WO | 2005092877 A1 | 10/2005 |
| WO | 2005095343 A1 | 10/2005 |
| WO | 2005095381 A1 | 10/2005 |
| WO | 2005097798 A | 10/2005 |
| WO | 2005116000 A1 | 12/2005 |
| WO | 2005116014 A1 | 12/2005 |
| WO | 2005117861 A1 | 12/2005 |
| WO | 2005117948 A1 | 12/2005 |
| WO | 2006005613 A1 | 1/2006 |
| WO | 2006027204 A1 | 3/2006 |
| WO | 2006029577 A1 | 3/2006 |
| WO | 2006029769 A1 | 3/2006 |
| WO | 2006036664 A1 | 4/2006 |
| WO | 2006040625 A1 | 4/2006 |
| WO | 2006041976 A1 | 4/2006 |
| WO | 2006047248 A1 | 5/2006 |
| WO | 2006048209 A1 | 5/2006 |
| WO | 2006048427 A1 | 5/2006 |
| WO | 2006068163 A1 | 6/2006 |
| WO | 2006071078 A1 | 7/2006 |
| WO | 2006076231 A2 | 7/2006 |
| WO | 2006083491 A2 | 8/2006 |
| WO | 2006135693 A2 | 12/2006 |
| WO | 2006137085 A1 | 12/2006 |
| WO | 2007007173 A2 | 1/2007 |
| WO | 2007014886 A1 | 2/2007 |
| WO | 2007014895 A2 | 2/2007 |

(56) References Cited

FOREIGN PATENT DOCUMENTS

| | | | |
|---|---|---|---|
| WO | 2007017423 | A1 | 2/2007 |
| WO | 2007033350 | A1 | 3/2007 |
| WO | 2007035355 | A2 | 3/2007 |
| WO | 2007035665 | A1 | 3/2007 |
| WO | 2007041053 | A2 | 4/2007 |
| WO | 2007071738 | | 6/2007 |
| WO | 2007072083 | A1 | 6/2007 |
| WO | 2007078726 | A2 | 7/2007 |
| WO | 2007093610 | A1 | 8/2007 |
| WO | 2007099345 | A1 | 9/2007 |
| WO | 2007120702 | A2 | 10/2007 |
| WO | 2007120936 | A2 | 10/2007 |
| WO | 2007128721 | A | 11/2007 |
| WO | 2007128724 | A1 | 11/2007 |
| WO | 2007128761 | A2 | 11/2007 |
| WO | 2007135196 | A2 | 11/2007 |
| WO | 2007137107 | A2 | 11/2007 |
| WO | 2007147185 | A1 | 12/2007 |
| WO | 2007148185 | A2 | 12/2007 |
| WO | 2007149797 | A2 | 12/2007 |
| WO | 2008005569 | A2 | 1/2008 |
| WO | 2008005576 | A1 | 1/2008 |
| WO | 2008017670 | | 2/2008 |
| WO | 2008022267 | A2 | 2/2008 |
| WO | 2008055870 | A1 | 5/2008 |
| WO | 2008055940 | A2 | 5/2008 |
| WO | 2008070692 | A2 | 6/2008 |
| WO | 2008081205 | A1 | 7/2008 |
| WO | 2008083238 | A2 | 7/2008 |
| WO | 2008087198 | A1 | 7/2008 |
| WO | 2008093878 | A1 | 8/2008 |
| WO | 2008093882 | A1 | 8/2008 |
| WO | 2008113000 | A1 | 9/2008 |
| WO | 2008130998 | A2 | 10/2008 |
| WO | 2008131149 | A2 | 10/2008 |
| WO | 2008137435 | A1 | 11/2008 |
| WO | 2009011451 | A | 1/2009 |
| WO | 2009022007 | A1 | 2/2009 |
| WO | 2009022008 | A1 | 2/2009 |
| WO | 2009022010 | A1 | 2/2009 |
| WO | 2009024542 | A2 | 2/2009 |
| WO | 2009063072 | A2 | 5/2009 |
| WO | 2009064399 | A1 | 5/2009 |
| WO | 2009099734 | A1 | 8/2009 |
| WO | 2009112691 | A2 | 9/2009 |
| WO | 2009121945 | A2 | 10/2009 |
| WO | 2009123992 | A1 | 10/2009 |
| WO | 2009147125 | A1 | 12/2009 |
| WO | 2010015664 | A1 | 2/2010 |
| WO | 2010018217 | A2 | 2/2010 |
| WO | 2010029089 | A2 | 3/2010 |
| WO | 2010043688 | A1 | 4/2010 |
| WO | 2010045656 | A2 | 4/2010 |
| WO | 2010072776 | A1 | 7/2010 |
| WO | 2010079197 | A1 | 7/2010 |
| WO | 2010086411 | A1 | 8/2010 |
| WO | 2010092124 | A1 | 8/2010 |
| WO | 2010092125 | A1 | 8/2010 |
| WO | 2010092163 | A2 | 8/2010 |
| WO | 2010096384 | A2 | 8/2010 |
| WO | 2010106457 | A2 | 9/2010 |
| WO | 2010147768 | A1 | 12/2010 |
| WO | 2011011541 | A1 | 1/2011 |
| WO | 2011039337 | A1 | 4/2011 |
| WO | 2011039367 | A2 | 4/2011 |
| WO | 2011064352 | A1 | 6/2011 |
| WO | 2011113947 | A1 | 9/2011 |
| WO | 2011138380 | A1 | 11/2011 |
| WO | 2011138421 | A1 | 11/2011 |
| WO | 2011161161 | A1 | 12/2011 |
| WO | 2012031124 | A2 | 3/2012 |
| WO | 2012065993 | A1 | 5/2012 |
| WO | 2012106303 | A1 | 8/2012 |
| WO | 2012120040 | A1 | 9/2012 |
| WO | 2013098372 | A1 | 7/2013 |
| WO | 2013103629 | A1 | 7/2013 |
| WO | 2013171167 | A1 | 11/2013 |
| WO | 2013174768 | A1 | 11/2013 |

OTHER PUBLICATIONS

He, Y.L. et al., "The influence of hepatic impairment on the pharmacokinetics f the dipeptidyl peptidase IV (DPP-4) inhibitor vildagliptin" European Journal of Clinical Pharmacology, vol. 63, No. 7, May 8, 2007, p. 677-686.

Huettner Silks et al: "BI 1356, a novel and selective xanthine based DPP-IV inhibitor, demonstrates good safety and tolerability with a wide therapeutic window" Diabetes< American Diabetes Association, US, vol. 56, No. Suppl 1, Jun. 1, 2007, p. A156.

JANUVIA; Patient Information; 2010.

Jones, R.M. et al., "GPR119 agonists for the treatment of type 2 diabetes". Expert Opinion on Therapeutic Patents 2009 Informa Healthcare for GBR LNKSD—DOI: 10.1517/13543770903153878, vol. 19, No. 10, Oct. 2009, p. 1339-1359.

Kanada, S. et al., "Safety, tolerability, pharmacokinetics and pharmacodynamics of multiple doses of BI 1356 (proposed tradename ONDERO), a dipeptidyl peptidase 4 inhibitor, in Japanese patients with type 2 diabetes" Diabetes, vol. 57, No. Suppl. 1, Jun. 2008, p. A158-A159 and 68th Annual Meeting of the American Diabetes Association: San Francisco, CA , Jun. 6-10, 2008.

Kim, D. et al., "(2R)-4-Oxo-4-(3-(Trifluoremethyl)-5,6-dihydro[1,2,4]triazolo[4,3-a]pyrazin-7(8H)-yl]-1-(2,4,5-trifluorophenyl)butan-2-amine: A Potent, Orally Active Dipeptidyl Peptidase IV inhibitor for the Treatment of Type 2 Diabetes." Journal Med. Chem, 2005, 48, p. 141-151.

Korom, S. et al; Inhibition of CD26/dipeptidyl peptidase IV activity in vivo prolongs cardiac allograft survival in rat recipients1,2, Transplantation, May 27, 1997, vol. 63, No. 10, pp. 1495-1500.

Lambier, A.M. et al., Dipeptidyl-Peptidase IV from Bench to Bedside: An Update on Structural Properties, Functions, and Clinical Aspects of the Enzyme DPP IV. Critical Reviews in Clinical Laboratory Sciences, 2003, 40(3), p. 209-294.

Levien,T.L. et al, "New drugs in development for the treatment of diabetes", Diabetes Spectrum, American Diabetes Association, US, vol. 22, No. 2, Jan. 1, 2009, pp. 92-106.

March, J. "Advanced Organic Chemistry: Reactions, Mechanisms, and Structure". Fourth Edition, 1992, pp. 652-653.

Meece, J. "When Oral Agents Fail: Optimizing Insulin Therapy in the Older Adult". Consultant Pharmacist, The Society, Arlington, VA US. vol. 24, No. Suppl B, Jun. 1, 2009, p. 11-17.

Mendes, F.D, et al. "Recent advances in the treatment of non-alcoholic fatty liver disease". Expert Opinion on Investigational Drugs, vol. 14, No. 1, Jan. 1, 2005, p. 29-35.

Merck: "Initial Therapy with Janumet (sitagliptin/metformin) provided significantly greater blood sugar lowering compared to metformin alone in patients with type 2 diabetes". Webwire.com, Jun. 8, 2009, p. 1-4. http://www.webwire.com/ViewPressRel.asp?aId=96695.

O'Farrell, et al., "Pharmacokinetic and Pharmacodynamic Assessments of the Dipeptidyl Peptidase-4 Inhibitor PHX1149: Double-Blind, Placebo-controlled, Single-and Multiple-Dose Studies in Healthy Subjects". Clinical Therapeutics, Excerpta Medica, Princeton, NJ, vol. 29, No. 8, 2007, p. 1692-1705.

Patani George A. et al.: "Bioisoterism : A Rational Approach in Drug Design", Chemical Reviews, 1996, vol. 96, No. 8, pp. 3147-3176.

Pei, Z.: "From the bench to the bedside: Dipeptidyl peptidase IV inhibitors, a new class of oral antihyperglycemic agents" Current Opinion in Drug Discovery and Development, Current Drugs, London, GB vol. 11, No. 4, Jul. 1, 2008 pp. 512-532.

Pospisilik, et al; Dipeptidyl Peptidase IV Inhibitor Treatment Stimulates ?—Cell Survival and Islet Neogenesis in Streptozotocin-Induced Diabetic Rats; Diabetes, vol. 52, Mar. 2003 pp. 741-750.

Priimenko, B. A., et al; Synthesis and Pharmacological Activity of Derivates of 6,8-Dimethyl Imidazo(1,2-f) Xanthine-(Russ.); Khimiko-Farmatsevticheskii zhurnal (1984) vol. 18, No. 12 pp. 1456-1461.

Rhee et al.: "Nitrogen-15-Labeled Deoxynucleosides. 3. Synthesis of [3-15N]-2'-Deoxyadenosine" J. Am. Chem. Soc. 1990, 112, 8174-8175.

(56) References Cited

OTHER PUBLICATIONS

Rosenstock, et al., "Efficacy and tolerability of initial combination therapy with vildagliptin and pioglitazone compared with component montherapy in patients with type 2 diabetes". Diabetes, Obesity and Metabolism, Mar. 2007, vol. 9, No. 2, p. 175-185.
Rosenstock, J. et al., "Alogliptin added to insulin therapy in patients with type 2 diabetes reduces HbA1c without causing weight gain or increased hypoglycaemia". Diabetes, Obesity and Metabolishm, Dec. 2009, vol. 11. No. 12, p. 1145-1152.
Salomon, J., et al; Ultraviolet and g-Ray-Induced Reactions of Nucleic Acid Constituents. Reactions of Purines with Amines; Photochemistry and Photobiology (1974) vol. 19 pp. 21-27.
Sathananthan, A., et al., "Personalized pharmacotherapy for type 2 diabetes mellitus". Personalized Medicine 2009 Future Medicine Ltd, vol. 6, No. 4, Jul. 2009, p. 417-422.
Sauer, R, et al. "Water-soluble phosphate prodrugs of 1-Propargyl-7-styrylxanthine derivatives, A2A-selective adenosine receptor antagonists". Journal Med. Chem., vol. 43, Issue 3, Jan. 2000, p. 440-448.
Schwartz, M. S. et al., "Type 2 Diabetes Mellitus in Childhood: Obesity and Insulin Resistance". JAOA Review Article, vol. 108, No. 9, Sep. 2008, p. 518.
Scientific Discussion: "Eucreas. Scientific discussion". Online Oct. 2007, p. 1-27, URL:http://www.emea.europa.eu/humandocs/PDFs/EPAR/eucreas/H-807-en6.pdf. see point 2. quality aspects pp. 2-4. (EMEA).
Sedo, A. et al; "Dipeptidyl peptidase IV activity and/or structure homologs: Contributing factors in the pathogenesis of rheumatoid arthritis?" Arthritis Research & Therapy 2005, vol. 7, pp. 253-269.
Stahl, P.H., "Handbook of Pharmaceutical Salts". C.G. Wermuth, Wiley-VCH, 2002, p. 61.
Sune Negre, J. M. "New Galenic Contributions to Administration Forms". Continued Training for Hospital Pharmacists 3.2. [retrieved on Feb. 23, 2011]. Retrieved from the internet <http://www.ub.es/legmh/capitols/sunyenegre.pdf>.
Tamm, E, et al., "Double-blind study comparing the immunogenicity of a licensed DTwPHib-CRM197 conjugate vaccine (Quattvaxem TM) with three investigational, liquid formulations using lower doses of Hib-CRM197 conjugate". Science Direct, Vaccine, Feb. 2005, vol. 23, No. 14, p. 1715-1719.
Tanaka, S.. et al; "Suppression of Arthritis by the Inhibitors of Dipeptidyl Peptidase IV," In. J. Immunopharmac., vol. 19, No. 1, pp. 15-24, 1997.
Thomas, L, et al: "BI 1356, a novel and selective xanthine beased DPP-IV inhibitor, exhibits a superior profile when compared to sitagliptin and vildagliptin." Diabetologoa, vol. 50, No. Suppl. 1, Sep. 2007, p. S363.
Thomas, L., "Chronic treatment with the Dipeptidyl Peptidase-4 Inhibitor BI 1356[9R)-8-(3-Amino-piperidin-1-yl)-7-but-2-ynyl-3-methy1-1(4-methyl-quinazolin-2-ylmethyl)-3,7-dihydro-purine-2,6-dione] Increases Basal Glucagon-Like Peptide-1 and Improves Glycemic Control in Diabetic Rodent Models" The Journal of Pharmacology and Experimental Therapeutics, Feb. 2009, vol. 328, No. 2, pp. 556-563.
Thomas, Leo et al: "(R)-8-(3-Amino-piperidin-1-y1)-7-but-2-yny1-3-methyl-1- (4-methyl-quinazolin-2-ylmethyl)-3,7-dihydro-purine-2,6-dione (BI 1356), a Novel Xanthine-Based Dipeptidyl Peptidase 4 Inhibitor, Has a Superior Potency and Longer Duration of Action Compared with Other Dipeptidyl Peptidase-4 Inhibitors" Journal of Pharmacology and Experimental Therapeutics, American Socity for Therapeutics, US, vol. 325, No. 1, Apr. 1, 2008, pp. 175-182 abstract p. 177, col. 2, paragraph 1 table 1 page 1B1, col. 2, last paragraph—p. 182, column 1.
Villhauer, E.B., "1-[[3-Hydroxy-1-adamantyl)amino]acetyl]-1-cyano-(S)-pyrrolidine: A Potent, Selective, and Orally Bioavailable Dipeptidyl Peptidase IV Inhibitor with Antihyperglycemic Properties" Journal Med. Chem, 2003, 46, p. 2774-2789.
Villhauer, E.B., et al., "1-{2-{5-Cyanopyridin-2-yl)amino)-ethylamino}acetyl-1-1(S)-pyrrolidine-carbonitrile: A Potent, Selective, and Orally Bioavailable Dipeptidyl Peptidase IV Inhibitor with Antihyperglycemic Properties". Journal of Medical Chemistry, 2002, vol. 45, No. 12, p. 2362-2365.
Wang Y et al: "BI-1356. Dipeptidyl-peptidase IV inhibitor, antidiabetic agent" Drugs of the Future, Prous Science, ES,vol. 33, No. 6, Jun. 1, 2008, pp. 473-477.
White, J.R., "Dipeptidyl Peptidase-IV Inhibitors: Pharmacological profile and Clinical Use". Clinical Diabetes, vol. 26, 2008, p. 53-57.
Wikipedia, Annulation. Jun. 23, 2008, http://en.wikipedia.org/wiki/Annelation.
Williams-Herman, D. et al., "Efficacy and safety of initial combination therapy with sitagliptin and metformin in patients with type 2 diabetes: a 54-week study". Current Medical Research and Opinion, Informa Healthcare, GB, vol. 25, No. 3, Jan. 2009, p. 569-583.
Wolff, M.E.: "Burger's Medicinal Chemistry and Drug Discovery" Fifth Edition, vol. 1: Principles and Practice, pp. 975-977, 1994, John Wiley & Sons, Inc.
World Health Organization (WHO). "Addendum 1 to "The use of stems in the selection of International Nonproprietary names (INN) for pharmaceutical substances"" Online Jun. 19, 2007, pp. 1-3, retrieved from URL: http://www.who.int/medicindedocs/index/assoc/s1414e/s1414e.pdf.
X-Ray Diffraction. The United States Pharmacopeia, 2002, USP 25 NF20, p. 2088-2089.
Yasuda, et al. "E3024 3-but-2-yny1-5-methyl-2-piperazin-1-y1-3,5-dihydro-4H-imidazol [ 4,5-d]pyridazin-4-one tosylate, is a move, selective and competitive dipeptidyl peptidase-IV inhibitor". European Journal of Pharmacology, vol. 548, No. 1-3, Oct. 24, 2006, p. 181-187. Abstract.
Yoshikawa, Seiji et al.: Chemical Abstract of Japanese Patent No. WO 2003/104229 Preparation of purinone derivatives as dipeptidylpeptidase IV (DPP-IV) inhibitors, 2003.
Zejc, Alfred, et al; "Badania Nad Piperazynowymi Pochodnymi Dwumetyloksantyn" Acta Polon Pharm, XXXV (1976) Nr. 4 pp. 417-421.
Zhong, Qing et al; "Glucose-dependent insulinotropic peptide stimulates proliferation and TGF-? release from MG-63 cells," Peptides 24 (2003) 611-616.
Zimmer et al; Synthesis of 8-Substituted Xanthines and their Oxidative Skeleton Rearrangement to 1-Oxo-2,4,7,9-tetraazaspiro[4,5]dec-2-ene-6,8,10-triones; Euripean Journal Organic Chemistry (1999) vol. 9 pp. 2419-2428.
Abstract in English for German DE2205815, 1972.
Abstract in English for German EP0023032, 1981.
Abstract in English, for KR20070111099, Nov. 11, 2007.
Ahren B: "DPP-4 inhibitors", Best practice and research in clinical endocrinology and metabolism—New therapies for diabetes 200712 GB LNKD—DOI:10.1016/J. Beem.2007.07.005, vol. 21, No. 4, Dec. 2007, pp. 517-533.
Augeri, D.J. "Discovery and Preclinical Profile of Saxagliptin (GMB-477118): A Highly Potent, Long-Acting, Orally Active Dipeptidyl Peptidase IV Inhibitor for the Treatment of Type 2 Diabetes". Journal Med. Chem, 2005, vol. 48, No. 15, p. 5025-5037.
Augusti, D.V. et al., "Quantitative determinatio of the enantiomeric composition of thalidomide solutions by electrospray ionizatio tandem mass spectrometry". Chem Comm, 2002, p. 2242-2243.
Augustyns, K. et al., The Unique Properties of Dipeptidyl-peptidase IV (DPP IV/CD 26) and the Therapeutic Potential of DPP-IV Inhibitors, Current Medicinal Chemistry, vol. 6, No. 4, 1999, pp. 311-327.
Aulinger, B.A. et al., "Ex-4 and the DPP-IV Inhibitor Vildagliptin have Additive Effects to Suppress Food Intake in Rodents". Abstract No. 1545-P, 2008.
Balaban, Y.H.et al., "Dipeptidyl peptidase IV (DDP IV) in NASH patients" Annals of Hepatology, vol. 6, No. 4, Oct. 1, 2007, pp. 242-250, abstract.
Balkan, B. et al, "Inhibition of dipeptidyl peptidase IV with NVP-DPP728 increases plasma GLP-1 (7-36 amide) concentrations and improves oral glucose tolerance in obses Zucker rates". Diabetologia, 1999, 42, p. 1324-1331.
Bastin, R.J. et al., "Salt Selection and Optimization Procedures for Pharmaceutical New Chemical Entities". Organic Process Research and Development, 2000, vol. 4, p. 427-435.

(56) References Cited

OTHER PUBLICATIONS

Beljean-Leymarie et al., Hydrazines et hydrazones hétérocycliques. IV. Synthèses de dérivés de l'hydrazine dans la série des imidazo[4,5-d]pyridazinones-4, Can. J. Chem., vol. 61, No. 11, 1983, pp. 2563-2566.

Bollag, R.J. et al; "Osteoblast-Derived Cells Express Functional Glucose-Dependent Insulinotropic Peptide Receptors," Endocrinology, vol. 141, No. 3, 2000, pp. 1228-1235.

Brazg, R. et al: "Effect of adding sitagliptin, a dipeptidyll peptidase-4 inhibitor, to metformin on 24-h glycaemic control and beta-cell function in patients with type 2 diabetes." Diabetes, Obesity and Metabolism, Mar. 2007, vol. 9, No. 2, Mar. 2007 pp. 186-193.

Brittain, H.G., "Methods for the Characterization of Polymorphs: X-Ray Powder Diffraction," Polymorphism in Pharmaceutical Solids, 1999, p. 235-238.

Bundgaard, H. "Design of prodrugs: Bioreversible derivatives for various functional groups and chemical entities". Royal Danish School of Pharmacy, 1985, p. 1-92.

Busso et al., "Circulating CD26 is Negatively Associated with Inflammation in Human and Experimental Arthritis," Am. J. Path., vol. 166, No. 2, Feb. 2005, pp. 433-442.

Caira, M.R., "Crystalline polymorphism of organic compounds" Topics in Current Chemistry, Springer, Berlin, vol. 198, 1998, p. 163-208.

Chemical Abstract. EP412358, 1991:185517, Findeisen.

Chemical Abstract: FR2707641, 1995:543545, Dodey.

Chemical Abstracts Accession No. 106:95577 Romanenko et al., "Synthesis and Biological Activity of 3-Methyl, 7- or 8-alkyl-7,8dialkyl, heterocyclic, and cyclohexylaminoxanthines," Zaporozh. Med. Institute (1986).

Chemical Abstracts Accession No. 1987:95577: Abstract of Romanenko et al., "Synthesis and biological activity of 3-methyl, 7- or 8-alkyl, 7,8-dialkyl, heterocyclic, and cyclohexylaminoxanthines," Zapoeozh, USSR, Farmatsevtichnii Zhurnal, 1986, (Kiev), vol. 5, 1986, pp. 41-44.

Clinical Trials. "View of NCT00601250 on Jan. 25, 2008: Efficacy and Safety of BI 1356 vs Placebo added to Metformin Background Therapy in Patients with Type 2 Diabetes" Clinical Trials. Gov Archive, [Online] Jan. 25, 2008 URL:http://clinicaltrials.gov/archive/NCT0601250/2008_01_25 [retrieved on Feb. 27, 2009].

Clinical Trials. NCT00622284. "Efficacy and safety of BI 1356 in combination with metformin in patients with type 2 diabetes" ClinicalTrials.gov (Online) No. NCT00622284, Feb. 13, 2008, p. 1-5, URL:http://clinicaltrial.gov/ct2/show/.

Clinical Trials. View of NCT00730275 updated on Aug. 7, 2008. "A study to assess the pharmacokinetics, safety and tolerability of Sitagliptin in adolescents". http://clinicaltrials.gov/archive/NCT00730275/2008_08_07.

Clinical Trials: NCT00954447, View on Jun. 14, 2010. "Efficacy and Safety of Linagliptin in Combination with Insulin in Patients with Type 2 Diabetes". <http://clinicaltrials.gov/archive/NCT00954447/2010_06_14>.

Clinical Trials: NCT00309608. Efficacy and safety of BI 1356 in combination with metformin in patients with type2 diabetes. Boehringer Ingelheim Pharmaceuticals, Jan. 27, 2009. Clinical Trials.gov . http://clinicaltrials.gov/archive/NCT00309608/2009_01_27.

Clinical Trials: NCT00602472. "BI 1356 in combination withe metformin and a sulphonylurea in Type 2 Diabetes". DrugLib.com, Nov. 3, 2008. http://www.druglib.com/trial/08/NCT00309608.html.

Clinical Trials: NCT00622284. Efficacy and Safety of BI 1356 in Combination with Metformin in Patients with Type 2 Diabetes. Boehringer Ingelheim Pharmaceuticals, Aug. 2008. http://clinicaltrials.gov/archive/NCT00622284/2010_01_13.

Clinical Trials: NCT00798161. "Safety and efficacy of BI 1356 Plus Metformin in Type 2 Diabetes, Factorial Design". Clinical Trials.gov archive. A Service of the U.S> National Institutes of Health. Nov. 24, 2008, p. 1-3. http://clinicaltrials.gov/archive/NCT00798161/2008_11_24.

Combs, D. W. et al., "Phosphoryl Chloride Induced Ring Contraction of 11,4-Benzodiazepinones to Chloromethylquinazolines". J. Heterocyclic Chemistry, BD. 23, 1986, p. 1263-1264.

Conarello, S.L. et al., "Mice lacking dipeptidyl peptidase IV are protected against obesity and insulin resistance". PNAS, May 27, 2003, vol. 100, No. 11, p. 6825-6830.

Cygankiewicz, Andrzej et al., Investigations into the Piperazine Derivatives of Dimethylxanthine:, Acta Polon. Pharm. [Papers of Polish Pharmacology], XXXOV, No. 5, pp. 607-612, 1977.

Dave, K.G. et al., "Reaction of Nitriles under Acidic Conditions, Part I. A General Method of Synthesis of Condensed Pyrimidines", J. Heterocyclic Chemistry, BD, 17, 1, ISSN 0022-152X,Nov. 1980, p. 1497-1500.

Deacon, C.F. et al; "Dipeptidyl peptidase IV inhabitation as an approach to the treatment and prevention of type 2 diabetes: a historical perspective;" Biochemical and Biophysical Research Communications (BBRC) 294 (2002) 1-4.

Deacon, C.F., et al. Inhibitors of dipeptidyl peptidase IV: a novel approach for the prevention and treatment of Type 2 diabetes? Expert Opinion on Investigational Drugs, Sep. 2004, vol. 13, No. 9, p. 1091-1102.

DeMeester, I. et al.; "CD26, let it cut or cut it down", Review: Immunology Today; Aug. 1999, vol. 20, No. 8 pp. 367-375.

Dugi, K.A. et al., "BI 1356, a novel xanthine-based DPP-IV inhibitor, exhibits high potency with a wide therapeutic window and significantly reduces postprandial glucose excursions after an oGTT". Diabetologia, vol. 50, No. Suppl 1, Sep. 2007, p. S367, and 43rd Annual Meeting of the European Association for the Study of Diabetes; Amsterdam, Netherlands, Sep. 18-21, 2007.

Eckhardt Matthias et al: 8-(3-(R)-aminopiperidin-1-yl)-7-but-2-yny 1-3-methyl-1-(4-methyl-quina zolin-2-ylmethyl)-3,7-dihydropurine-2,6-dione (BI 1356), a highly potent, selective, long-acting, and orally bioavailable DPP-4 inhibitor for the treatment of type 2 diabetes: Journal of Medicinal Chemistry, American Chemical Society. Washington.; US, vol. 50, No. 26, Dec. 1, 2007, p. 6450-6453.

Eckhardt, M. et al., "3,5-dihydro-imidazo[4,5-d]pyridazin-4-ones: a class of potent DPP-4 inhibitors" Bioorganic &.Medicinal Chemistry Letters, Pergamon, Elsevier Science, GB, vol. 18, No. 11, Jun. 1, 2008, pp. 3158-3162, XP022711188.

Elrishi M A et al: "The dipeptidyl-peptidase-4 (D::-4) inhibitors: A new class of oral therapy for patients with type 2 diabetes mellitus" Practical Diabetes International Chichester, vol. 24, No. 9, Nov. 1, 2007 pp. 474-482.

Florez, Jose C., et al., "TCF7L2 Polymorphisms and progression to diabetes in the diabetes prevention program". New England Journal of Medicine, MA Medical Society, vol. 355, No. 2, Jul. 20, 2006, p. 241-250.

Gallwitz, B. et al., "Saxagliptin, a dipeptidyl peptidase IV inhibitor for the treatment of type 2 diabetes". IDrugs, vol. 11, No. 12, Dec. 2008, p. 906-917.

Garber, A.J. et al., "Update: Vildaglitin for the treatment of Type 2 diabetes" Expert Opinion on Investigational Drugs, 200801GB, vol. 17, No. 1, Jan. 2008, p. 105-113.

Garcia-Soria, et al., "The dipeptidyl peptidase-4 inhibitor PHX1149 improves blood glucose control in patents with type 2 diabetes mellitus". Diabetes, Obesity, and Metabolism, Apr. 2008, vol. 10, No. 4, p. 293-300.

Gennaro, Alfonso, R; Remington: The Science and Practice of Pharmacy: Oral Solid Dosage Forms; Mack Publishing Company, Philadelphia, PA (1995) vol. II, 19th Edition, Ch. 92 pp. 1615-1649.

Giron, D.; Thermal Analysis and Calorimetric Methods in the Characterisation of Polymorphs and Solvates; Thermochimica Acta (1995) vol. 248 pp. 1-59.

Graefe-Mody et al., "The novel DPP-4 inhibitor . . . " Diabetes, (online) 2008, XP002561421 http://professional.diabetes.org/content/posters/2008/p553-p.pdf.

Greene, T.W, et al., "Protection for the Amino Group". Protective Groups in Organic Synthesis, 3rd edition, 1999, p. 494-653.

Gwaltney, S. "Medicinal Chemistry Approaches to the Inhibition of Dipeptidyl Peptidase IV", Current Topics in Medicinal Chemistry, 2008, 8, p. 1545-1552.

(56) References Cited

OTHER PUBLICATIONS

Conarello, S.L. et al; "Mice lacking dipeptidyl peptidase IV are protected against obesity and insulin resistance," PNAS 2003; 100:6825-6830; originally published online May 14, 2003; information current as of Dec. 2006. www.pnas.org/cgi/content/full/100/11/6825.
Demuth, H-U. et al., "Type 2 diabetes—Therapy with dipeptidyl peptidase IV inhibitors". Biochimica et Biophysica Acta, vol. 1751(1), 2005, p. 33-44.
European Search Report for EP 08 15 9141 mailed Apr. 6, 2009 (European counterpart of U.S. Appl. No. 12/143,128).
Gallwitz, B. "Sitagliptin with Metformin: Profile of a Combination for the Treatment of Type 2 Diabetes". Drugs of Today, Oct. 2007, 43(10), p. 681-689.
Graefe-Mody, et al; Evaluation of the Potential for Steady-State Pharmacokinetic and Phamacodynamic Interactions Between the DPP-4 Inhibitor Linagliptin and Metformin in Healthy Subjects; Currents Medical Research and Opinion (2009) vol. 25, No. 8 pp. 1963-1972.
Hunziker, D. et al, "Inhibitors of DPP IV-recent advances and structural views", Current Topics in Medicinal Chemistry, 2005, vol. 5 issue 16, pp. 1623-1637.
International Search Report and Written Opinion for PCT/EP2011/070156 dated Jan. 17, 2012.
Kibbe, Editor. Handbook of Pharmaceuticals Excipiets, Third Edition, Copovidon-pp. 196-197, Date of Revision: Dec. 16, 2008. Mannitol-pp. 424-425, Date of Revision: Feb. 19, 2009.
Knorr, M. et al., "Comparison of Direct and Indirect Antioxidant Effects of Linagliptin (BI 1356, Ondero) with other Gliptins—Evidence for Anti-Inflammatory Properties of Linagliptin". Free Radical Biology and medicine, Elsevier Science, U.S. vol. 49, Oct. 23, 2010, p. S197.
Uhlig-Laske, B. et al., "Linagliptin, a Potent and Selective DPP-4 Inhibitior, is Safe and Efficacious in Patients with Inadequately Controlled Type 2 Diabetes Despite Metformin Therapy". 535-P Clinical Therapeutics/New Technology—Pharmacologic Treatment of Diabetes or Its Complications, Posters, vol. 58, Jun. 5, 2009, pA143.
Mayo Clinic Staff: "Nonalchoholic fatty liver disease: Prevention" [retrieved on Nov. 30, 2012]. retrieved from the Internet: ,URL: http://www.mayoclinic.com/health/nonalcoholic-fatty-liver-disease/DS00577DSECTION=prevention>.
Shanks, N. et al., Are animal models predictive for humans?, PEHM, Philosophy, Ethics, and Humanaities in Medicine, 4(2), 2009, 1-20.
Hermann, Robert, et al; Lack of Association of PAX4 Gene with Type 1 Diabetes in the Hungarian Populations; Diabetes (2005) vol. 54 pp. 2816-2819.
Ahren, Bo, et al; Improved Meal-Related b-Cell Function and Insulin Sensitivity by the Dipeptidyl Peptidase-IV Inhibitor Vildagliptin in Metformin-Treated Patients with Type 2 Diabetes Over 1 Year; Diabetes Care (2005) vol. 28, No. 8 pp. 1936-1940.
Brazg, Ronald, et al; Effect of Adding MK-0431 to On-Going Metforming Therapy in Type 2 Diabetic Patients Who Have Inadequate Glycemic Control on Metformin; Diabetes ADA (2005) vol. 54, Suppl. 1 p. A3.
Abstract in English for German DE10109021, 2002.
American Diabetes Association, "Standards of Medical Care in Diabetes-2008." Diabetes Care, Jan. 2008, vol. 31, Supplement 1, pp. S12-S54.
Anonymous, Clinicaltrials.gov, 2008, No. NCT00622284, "Efficacy and Safety of BI 1356 in combination with metformin in patients with type 2 diabetes" p. 1-5.
Anstee, Quentin M. et al. "Mouse models in non-alcholic fatty liver disease and steatohepatitis research" (2006) International Journal of Expermental Pathology, vol. 87, pp. 1-16.
Balbach, S. et al., "Pharmaceutical evaluation of early development candidates the 100 mg-approach." International Journal of Pharmaceutics, 2004, vol. 275, pp. 1-12.
Berge, S. et al., "Pharmaceutical Salts." Journal of Pharmaceutical Sciences, 1977, vol. 66, No. 1, pp. 1-19.
Bernstein, Joel "Polymorphism in Molecular Crystals." Oxford University Press, 2002, p. 9.
Bosi, E. et al., "Effects of Vildagliptin on Glucose Control Over 24 Weeks in Patients With Type 2 Diabetes Inadequately Controlled With Metformin." Diabetes Care, 2007, vol. 30, No. 4, p. 890-895.
Byrn, Stephen R. "Solid-State Chemistry of Drugs." Academic Press, 1982, pp. 1-27.
Campbell, R. Keith "Rationale for Dipeptidyl Peptidase 4 Inhibitors: A New Class of Oral Agents for the Treatment of Type 2 Diabetes Mellitus." The Annals of Pharmacotherapy, Jan. 2007, vol. 41, pp. 51-60.
Charbonnel, B. et al., "Efficacy and Safety of the Dipeptidyl Peptidase-4 Inhibitor Sitagliptin Added to Ongoing Metformin Therapy in Patients With Type 2 Diabetes Inadequately Controlled With Metformin Alone." Diabetes Care, 2006, vol. 29, No. 12, pp. 2638-2643.
Chemical Abstracts Service, Database Accession number No. RN 668270-12-01, 2004, "1H-Purine-2,6-dione, 8-[(3R)-3-amino-1-piperidinyl]-7-(2-butyn-1-y0-3,7-dihydro-3-methyl-1-[(4-methyl-2-quinazolinyl)methyl]".
Chemistry Review: Tradjenta, "NDA 201280, CMC Director Review Tradjenta (Linagliptin) Tablets." Center for Drug Evaluation and Research, Aug. 9, 2010, Retrieved from the internet on Nov. 1, 2013, http://www.accessdata.fda.gov_drugsatfda_docs/nda/2011/201280Orig1s000ChemR.pdf.
Clinical Trial NCT00622284 (published online at clinicaltrials.gov on Feb. 22, 2008).
Dave, Rutesh H. "Overview of pharmaceutical excipients used in tablets and capsules." Drug Topics, Oct. 24, 2008.
Deacon, Carolyn F., et al., "Linagliptin, a xanthine based dipeptyl peptidase-4 inhibitor with an unusual profile for the treatment of type 2 diabetes" Expert Opinion Investig. Drugs 2010, 19 (1) p. 133-140.
Deacon, Carolyn F. et al. "Linaglipitn, a xanthine-based dipeptidyl peptidase-4 inhibitor with an unusual profile for the treatment of type 2 diabetes" Expert Opin. Investig. Drugs (2010) 19(1): 133-140.
Definition of "prevent", e-dictionary, Aug. 15, 2013, http://dictionary.reference.com/browse/prevent.
Diabetes Health Center, "Diabetic Retinopathy—Prevention." Retrieved online Mar. 22, 2011. www.diabetes.webmd.com/tc/diabetic-retinopathy-prevention <http://www.diabetes.webmd.com/tc/diabetic-retinopathy-prevention?print=true>.
Diabetesincontrol.com "EASD: Eucreas, a Combination of Galvus and Metformin, Recommended for Approval." Diabetes in Control.com, Sep. 25, 2007, Retrieved from internet on Nov. 30, 2012, http://www.diabetesincontrol.com/articles/53-diabetes-news/5145.
Diabetic Neuropathy, Retrieved online Mar. 6, 2012. www.mayoclinic.com/health/diabetic-neuropathy/DS01045/METHOD=print&DSE <http://www.mayoclinic.com/health/diabetic-neuropathy/DS01045/METHOD=print&DSE>.
Drucker, et al.., The incretin system:glucagon-like peptide-1 receptor agonists and dipeptidyl peptidase-4 inhibitors in type 2 diabetes. Lancet, 2006, 368: 1696-705.
Dunitz, J. et al., "Disappearing Polymorphs." Acc. Chem. Res. 1995, vol. 28, No. 4, pp. 193-200.
Edosada, C. Y. et al. "Selective Inhibition of Fibroblast Activation Protein Protease Based on Dipeptide Substrate Specificity." The Journal of Biological Chemistry, 2006, vol. 281, No. 11, pp. 7437-7444.
eMedicine Health, "Diabetes Causes." Retrieved from internet on Aug. 22, 2013. <http://www.onhealth.com/diabetes_health/page3.htm#diabetes_causes>.
Eucreas Scientific Discussion, 2007, p. 1-27, www.emea.europa.eu/humandocs/PD/Fs/EPAR/eucreas/H-807-en6.pdf, Anonymous.
Ferry, Robert Jr., "Diabetes Causes." eMedicine Health, MedicineNet.com, 2013, Retrieved from internet on Aug. 22, 2013, http://www.onhealth.com/diabetes_health/page3.htm#diabetes_causes.
Florez, J. et al. "TCF7L2 Polymorphisms and Progression to Diabetes in the Diabetes Prevention Program." The New England Journal of Medicine, 2006, vol. 355, No. 3, pp. 241-250.
Forst, T. et al., "The Novel, Potent, and Selective DPP-4 Inhibitor BI 1356 Significantly Lowers HbA1c after only 4 weeks of Treatment in Patients with Type 2 Diabetes." Diabetes, Jun. 2007, Poster No. 0594P.

(56) References Cited

OTHER PUBLICATIONS

Fukushima et al., Drug for Treating Type II Diabetes (6), "action-mechanism of DPP-IV inhibitor and the availability thereof" Mebio, 2009, vol. 26, No. 8, p. 50-58.
Gallwitz, B. et al., DPP IV inhibitors for the Treatment of Type 2 Diabetes; Diabetes Frontier (2007) vol. 18, No. 6 pp. 636-642.
Garber, A. J. et al., "Effects of Vildagliptin on Glucose Control in Patients with Type 2 Diabetes Inadequately Controlled with a Sulphonylurea". Diabetes, Obesity and Metabolism (2008) vol. 10 pp. 1047-1055.
Gennaro, Alfonso R., Remington Farmacia, 19th Edition, Spanish copy, 1995, p. 2470.
Halimi, et al., "Combination treatment in the management of type 2 diabetes focus on vildagliptin and metformin as a single tablet", Vascualr Health and Risk Management, 2008, 4(3) p. 481-92.
Hayashi, Michio., "Recipe for Oral Hypoglycemic Agents to Pathological Condition" Pharmacy (2006) vol. 57, No. 9 pp. 2735-2739.
Heise, T. et al., "Treatment with BI 1356, a Novel and Potent DPP-IV Inhibitor, Significantly Reduces Glucose Excursions after an oGTT in Patients with Type 2 Diabetes." A Journal of the American Diabetes Association, Jun. 2007, vol. 56, Supplement 1, Poster No. 0588P.
Herman, G. A. et al., "Dipeptidyl Peptidase-4 Inhibitors for the Treatment of Type 2 Diabetes: Focus on Sitagliptin." Clinical Pharmacology and Therapeutics, 2007, vol. 81, No. 5, pp. 761-767.
Herman, Gary et al. "Co-Administration of MK-0431 and Metformin in Patients with Type 2 Diabetes Does Not Alter the Pharmacokinetics of MK-0431 or Metformin" (2005) Journal of American Diabetes Association vol. 54, Supplement 1, 3 pgs.
Hermansen, K., "Efficacy and Safety of the Dipeptidyl Peptidase-4 Inhibitor, Sitagliptin, in Patients with Type 2 Diabetes Mellitus Inadequately Controlled on Glimepiride Alone or on Glimepiride and Metformin". Diabetes, Obesity and Metabolism (2007) vol. 9, No. 5 pp. 733-745.
Hilfiker, R. et al., "Relevance of Solid-state Properties for Pharmaceutical Products." Polymorphism in the Pharmaceutical Industry, 2006, Chapter 1, pp. 1-19.
Horsford, E. N. "On the source of free hydrochloric acid in the gastric juice." Proceedings of the Royal Society of London, Published in 1868-1869, vol. 17, pp. 391-395.
Hu, Y. et al., "Synthesis and Structure-activity Relationship of N-alkyl Gly-boro-Pro Inhibitors of DPP4, FAP, and DPP7." Bioorganic & Medicinal Chemistry Letters 15, 2005, pp. 4239-4242.
Huttner, S. et al., "Safety, Tolerability, Pharmacokinetics, and Pharmacodynamics of Single Oral Doses of BI 1356, an Inhibitor of Dipeptidyl Peptidase 4, in Healthy Male Volunteers." Journal of Clinical Pharmacology, 2008, vol. 48, No. 10, pp. 1171-1178.
Inukai, T., "Treatment of Diabetes in Patients for Whom Metformin Treatment is Not Appropriate." Modern Physician, 2008, vol. 28, No. 2, pp. 163-165.
Kharkevich, D. A., "Educational Literature" Pharmacology (1987) Third Edition, Meditsina Press, Moscow pp. 47-48.
Kidney Disease (Nephropathy), Retrieved online May 13, 2013. www.diabetes.org/living-with-diabetes/complications/kidney-disease-nephropathy.html <http://www.diabetes.org/living-with-diabetes/complications/kidney-disease-nephropathy.html>.
Kim, Kwang-Rok et al., "KR-62436, 6-{2-{2-(5-cyano4,5-dihydropyrazol-1-yl)-2-oxoethylamino}ethylamino) nicotinonitrile, is a novel dipeptidyl peptidase-IV (DDP-IV inhibitor with anti-hyperglycemic activity" European Journal of Pharmacology 518, 2005, p. 63-70.
Komori, Kiyoshi., "Treatment of Diabetes in Patients for Whom Metforming Treatment is Not Appropriate." Modern Physician (2008) vol. 28, No. 2 pp. 163-165.
Lakatos, P. L. et al., "Elevated Serum Dipeptidyl IV (CD26, EC 3.4.14.5) Activity in Experimental Liver Cirrhosis." European Journal of Clinical Investigation, 2000, vol. 30, No. 9, pp. 793-797.
Matsumiya, Teruhiko, et al., "Therapeutic Drugs for Clinicians" Diagnosis and Treatment (2008) vol. 96, No. 2 pp. 389-390.
Medline Plus, "Obesity" 2013, Retrieved from Internet on Aug. 22, 2013, http://www.nlm.nih.gov/medlineplus/obesity.html.
Nathan, D. et al., "Management of Hyperglycemia in Type 2 Diabetes: A Consensus Algorithm for the Initiation and Adjustment of Therapy." Diabetes Care, Aug. 2006, vol. 29, No. 8, pp. 1963-1972.
Nauck, M. A. et al., "Efficacy and Safety of Adding the Dipeptidyl Peptidase-4 Inhibitor Alogliptin to Metformin Therapy in Patients with Type 2 Diabetes Inadequately Controlled with Metformin Monotherapy: A Multicentre, Randomised, Double-Blind, Placebo-Cotrolled Study." Clinical Practice, 2008, vol. 63, No. 1, pp. 46-55.
Nauck, M. A. et al., "Efficacy and Safety of the Dipeptidyl Peptidase-4 Inhibitor, Sitagliptin, Compared with the Sulfonylurea, Glipizide, in Patients with Type 2 Diabetes Inaduately Controlled on Metformin alone: A Randomized, Double-Blind, Non-Inferiority Trial." Diabetes Obesity and Metabolism, 2007, vol. 9, No. 2, pp. 194-205.
Nielsen, L., "Incretin mimetics and DPP-IV inhibitors for the treatment of type 2 diabetes." Drug Discovery Today, 2005, vol. 10, No. 10, pp. 703-710.
Nihon Ijinpo, Japan Medicinal Journal, 2001, No. 4032, p. 137.
Office Action for U.S. Appl. No. 10/695,597 mailed May 2, 2008.
Plummer, C.J.G. et al., "The Effect of Melting Point Distributions on DSC Melting Peaks." Polymer Bulletin, 1996, vol. 36, pp. 355-360.
Pratley, R. et al., "Inhibition of DPP-4: a new therapeutic approach for the treatment of type 2 diabetes." Current Medical Research and Opinion, 2007, vol. 23, No. 4, pp. 919-931.
Rosenstock, et al., Sitagliptin Study 019 Groups, Efficacy and safety of the dipeptidyl peptidase-4 inhibitor sitagliptin, Clinical Therapeutics, 2006, vol. 28, Issue 10, p. 1556-1568.
Russell-Jones, D. et al., "Liraglutide vs insulin glargine and placebo in combination with metformin and sulfonylurea therapy in type 2 diabetes mellitus (LEAD-5 met+SU): a randomised controlled trial." Diabetologia, 2009, vol. 52, pp. 2046-2055.
Sarafidis, P. et al., "Cardiometabolic Syndrome and Chronic Kidney Disease: What is the link?"JCMS 2006, 1: p. 58-65.
Schmidt, D. et al., "Fibromatosis of Infancy and Childhood Histology, Ultrastructure and Clinicopathologic Correlation." Zeitschrift für Kinderchirurgie, 1985, vol. 40, No. 1, pp. 40-46.
Shintani, Maki, et al., "Insulin Resistance and Genes" Circulatory Sciences (1997) vol. 17, No. 12 pp. 1186-1188.
Singhal, D. et al., "Drug polymorphism and dosage form design: a practical perspective." Advanced Drug Delivery Reviews, 2004, vol. 56, pp. 335-347.
St. John Providence Health Center, "Preventing Obesity in Children and Teens." Retrieved from internet on Aug. 22, 2013, http://www.stjohnprovidence.org/Health I nfoLib/swarticle.aspx?type=85&id=P07863.
Targher, G. et al., "Prevalence of Nonalcoholic Fatty Liver Disease and Its Association With Cardiovascular Disease Among Type 2 Diabetic Patients." Diabetes Care, 2007, vol. 30, No. 5, pp. 1212-1218.
Third Party Observation for application No. EP20070728655, May 13, 2013.
Tounyoubyou, "Symposium-19: Future Perspectives on Incretion Therapy in Diabetes." 2008, vol. 51, Suppl. 1, pS-71, S19-2.
Tradjenta, Highlights of Prescribing Information (revised Sep. 2012).
Tribulova, N. et al. "Chronic Disturbances in NO Production Results in Histochemical and Subcellular Alterations of the Rat Heart." Physiol. Res., 2000, vol. 49, No. 1, pp. 77-88.
Tsujihata, et al., "TAK-875, an orally available G protein-Coupled receptor 40/Free fatty acid receptor 1 Agonist, Enhances Glucose Dependent Insulin Secretion and improves both Postprandial and Fasting hyperglycemic in type 2 Diabetic rats", J. Pharm Exp. 2011, vol. 339, No. 1, p. 228-237.
United Healthcare, "Diabetes." Retrieved from Internet on Aug. 22, 2013, http://www.uhc.com/source4women/health_topics/diabetesirelatedinformation/
d0f0417b073bf11OVgnVCM1000002f1Ob1Oa_. htm.
Abstract in English for JP 2002/348279, Dec. 4, 2002.
Abstract in English for JP 2003/286287, Oct. 10, 2003.
Adebowale, K.O. et al., "Modification and properties of African yam bean (*Sphenostylis stenocarpa* Hochst. Ex A. Rich.) Harms starch I: Heat moisture treatments and annealing." Food Hydrocolloids, 2009, vol. 23, No. 7, pp. 1947-1957.

(56) References Cited

OTHER PUBLICATIONS

Al-Masri, Journal of Enzyme Inhibition and Medicinal Chemistry, "Inhibition of dipeptyl peptidase IV (DPP iv) is one of the mechanisms explaining hypoglycemic effect of berberine", 2009.

Alter, M. et al., "DPP-4 Inhibition on Top of Angiotensin Receptor Bockade Offers a New Therapeutic Approach for Diabetic Nephropathy." Kidney and Blood Pressue Research, 2012, vol. 36, No. 1, pp. 119-130.

Borloo, M. et al. "Dipeptidyl Peptidase IV: Development, Design, Synthesis and Biological Evaluation of Inhibitors." 1994, Universitaire Instelling Antwerpen, vol. 56, pp. 57-88.

Boulton, D.W. et al., "Safety, Tolerability, Pharmacokinetics and Pharmacodynamics of Once-Daily Oral Doses of Saxagliptin for 2 Weeks in Type 2 Diabetic and Healthy Subjects." Diabetes, 2007, Supplement 1, vol. 56, pp. A161.

Chan, J.C. et al., "Safety and efficacy of sitagliptin in patients with type 2 diabetes and chronic renal insufficiency." 2008, Diabetes, Obesity and Metabolism, vol. 10, pp. 545-555.

Chaykovska, L. et al., "Effects of DPP-4 Inhibitors on the Heart in a Rat Model of Uremic Cardiomyopathy." www.plosone.org, 2011, vol. 6, No. 11, p. e27861.

ChemGaroo, "Leaving Group." 1999, Retrieved online: http://www.chemgapedia.de/vsengine/vlu/vsc/en/ch/12/oc/vlu organik/substitution/sn _2/sn 2. vlu/Page/vsc/en/ch/12/oc/substitution/sn _2/abgangsgrupen/abgangsgruppe. vscml.html.

Chisari, A. et al. "Sulphinyl, Sulphonyl, and Sulphonium Groups as Leaving Groups in Aromatic Nucleophilic Substitutions." Journal of the Chemical Society, Perkin Transactions II, 1982, pp. 957-959.

Clinical Trials: NCT00309608, "Efficacy and Safety of BI 1356 BS (Linagliptin) in Combination With Metformin in Patients With type2 Diabetes" Boehringer Ingelheim Pharmaceuticals, last updated: Dec. 11, 2013.

Glucotrol XL (glipizide), package insert, Pfizer, Apr. 1, 2002.

Gomez-Perez, et al, "Insulin Therapy:current alternatives", Arch. Med.Res. 36: p. 258-272 (2005).

Graefe-Mody, U. et al., "Effect of Renal Impairment on the Pharmacokinetics of the Dipeptidyl Peptidase-4 Inhibitor Linagliptin." Diabetes, Obseity and Metabolism, 2011, pp. 939-946.

Groop, P.-H. et al., "Effects of the DPP-4 Inhibitor Linagliptin on Albuminuria in Patients with Type 2 Diabetes and Diabetic Nephropathy." 48th EASD Annual Meeting, Berlin, Abstract 36, Oct. 2012. <http://www.abstractsonline.com/Plan/ViewAbstract.aspx?sKey=0b0017b9-9e90-4695-b9af-b6870e96a921&cKey=421edb9c-b940-40f0-b282-8e61245561d5&mKey=2dbfcaf7-1539-42d5-8dda-0a94abb089e8>.

Haluzik, M. et al., "Renal Effects of DPP-4 Inhibitors: A Focus on Microalbuminuria." International Journal of Endocrinology, 2013, vol. 35, No. 6, pp. 1-7.

Hansen, H. et al., "Co-Administration of the DPP-4 Inhibitor Linagliptin and Native GLP-1 Induce Body Weight Loss and Appetite Suppression." 73rd Annual Meeting Science Session, ADA, Chicago, Jun. 21, 2013.

Headland, K. et al., "The Effect of Combination Linagliptin and Voglibose on Glucose Control and Body Weight." 73rd Annual Meeting Science Session, ADA, Chicago, Jun. 21, 2013.

Heihachiro, A. et al., "Synthesis of Prolyl Endopeptidase Inhibitors and Evaluation of Their Structure-Activity Relationships: In Vitro Inhibition of Prolyl Endopeptidase from Canine Brain." 1993, Chemical and Pharmaceutical Bulletin, vol. 41, pp. 1583-1588.

Hocher, B. et al., "Renal and Cardiac Effects of DPP-4 Inhibitors—from Preclinical Development to Clinical Research." Kidney & Blood Pressue Research, 2012, vol. 36, No. 1, pp. 65-84.

Holman, et al., "Addition of biphasic, prandial, or basal insulin to oral therapy in type 2 diabetes", N. England Journal Medicine, p. 1716-1730, 2007.

Johansen, O. E. et al., "Cardiovascular safety with linagliptin in patients with type 2 diabetes mellitus: a pre-specified, prospective, and adjudicated meta-analysis of a phase 3 programme." Cardiovascular Diabetology, Biomed Central, 2012, vol. 11, No. 1, pp. 1-10.

Johansen, O.E. et al., "b-cell Function in Latnet Autoimmune Diabetes in Adults (LADA) Treated with Linagliptin Versus Glimepiride: Exploratory Results from a Two Year Double-Blind, Randomized, Controlled Study." www.abstractsonline.com, Jun. 10, 2012, XP-002708003.

John Hopkins Children's Center, "Liver Disorders and Diseases." Retrieved online May 26, 2014 <http://www.hopkinschildrens.org/non-alcoholic-fatty-liver-disease.aspx>.

Kroller-Schön, S. et al., "Glucose-independent Improvement of Vascular Dysfunction in Experimental Sepsis by Dipeptidyl Peptidase-4 Inhibition." Cardiovascular Research, 2012, vol. 96, No. 1, pp. 140-149.

Lee Jones, K. et al., "Effect of Metformin in Pediatric Patients With Type 2 Diabetes." Diabetes Care, 2002, vol. 25, No. 1, pp. 89-94.

Leibovitz, Cardiovascular Diabetology, Sitagliptin Treatment in diabetes patients presenting with acute coronary syndrome: results from the Acute Coronary Syndrome Israeli Survey, 2013.

Lim, Seoul National Univ. Bundang Hospital, Effect of a Dipeptyl Peptidase-IV Inhibitor, Des-Fluoro Sitagliptin, on Neointimal Formation after Balloon Injury in Rats, 2012, vol. 7, Issue 4.

Lovshin, J.A. et al., "Incretin-based therapies for type 2 diabetes mellitus." Nature Reviews Endocrinology, 2009, vol. 5, pp. 262-269.

Matsumiya, Tokyo Medical University, Department of Pharmacology, Diagnosis and Therapy, vol. 96, No. 2, 2008.

Nielsen, L., "Incretin Mimetics and DPP-IV Inhibitors for the Treatment of Type 2 Diabetes." DDT, 2005, vol. 10, No. 10, pp. 703-710.

Nippon Rinsho, Insulin Glargine, Tokyo Women's Medical Univ. Diabetes Center, 2011.

Partial International Search Report for PCT/EP2014/060160, mailing date Jun. 30, 2014.

Rosenbloom, et al., "Type 2 Diabetes mellitus in the child and adolescent", Pediatric Diabetes, 2008, p. 512-526.

Sharkovska, Y. et al., "DPP-4 Inhibition with Linagliptin Delays the Progression of Diabetic Nephropathy in db/db Mice." 48th EASD Annual Meeting, Berlin, Abstract 35, Oct. 2012. <http://www.abstractsonline.com/Plan/ViewAbstract.aspx?sKey=0b0017b9-9e90-4695-b9af-b6870e96a921&cKey=8eff47ae-db49-4c36-a142-848ac0680405&mKey=2dbfcaf7-1539-42d5-8dda-0a94abb089e8>.

Silverman, G. et al., "Handbook of Grignard Reagents." 1996, Retrieved online:<http://books.google.com/books?id=82CaxfY-uNkC&printsec=frontcover&dq=intitle:Handbook+intitle:of+intitle:Grignard+intitle:Reagents&hl=en&sa=X&ei=g06GU5SdOKngsATphYCgCg&ved=0CDYQ6AEwAA#v=onepage&q&f=false>.

Sortino, M.A. et al., "Linagliptin: a thorough characterization beyond its clinical efficacy." Frontiers in Endocrinology, 2013, vol. 4, Article 16, pp. 1-9.

Thornber, C.W., "Isosterism and Molecular Modification in Drug Design." Chemical Society Reviews, 1979, pp. 563-580.

Tsuprykov, O. et al., Linagliptin is as Efficacious as Telmisartan in Preventing Renal Disease Progression in Rats with 5/6 Nephrectomy, 73rd Annual Meeting Science Session, ADA, Chicago, Jun. 2013. <http://www.abstractsonline.com/Plan/ViewAbstract.aspx?sKey=e68ac573-fe45-4c2f-9485-6270854fc10b&cKey=3c387569-04de-4f8c-b025-b358df91ca64&mKey=%7b89918D6D-3018-4EA9-9D4F-711F98A7AE5D%7d>.

U.S. Appl. No. 12/724,653, filed Mar. 16, 2010—Xanthine Derivatives, the Preparation Thereof and Their Use as Pharmaceutical Compositions. Inventor: Frank Himmelsbach, et al.

U.S. Appl. No. 12/767,855, filed Apr. 27, 2010—Xanthine Derivatives, the Preparation Thereof and Their use as Pharmaceutical Compositions. Inventor: Frank Himmelsbach, et al.

Wertheimer, et al., "Drug Delivery Systems improve pharmaceutical profile and faciliate medication adherence", Adv. Therapy 22: p. 559-577 (2005).

Youssef, S. et al., "Purines XIV. Reactivity of 8-Promo-3,9-dimethylxanthine Towards Some Nucleophilic Reagents." Journal of Heterocyclic Chemistry, 1998, vol. 35, pp. 949-954.

\* cited by examiner

| Reactivity towards | Linagliptin | Alogliptin | Saxagliptin | Vildagliptin | Sitagliptin |
|---|---|---|---|---|---|
| Superoxide (DHE) | no | no | no | very weak | no |
| Superoxide (Amplex) | no | no | no | | |
| Peroxynitrite (DHR) | very weak | no | no | no | no |
| Peroxynitrite (HPLC) | no | no | no | no | no |
| Sin-1 derived Peroxynitrite | very weak | no | no | no | no |
| Peroxide (Amplex) | good | weak | no | very weak | very weak |

1) Non-diabetic eNOS ko control mice, placebo (natrosol) (n=14)
2) sham treated diabetic eNOS ko mice, placebo (natrosol) (n=17)
3) Telmisartan (p.o. 1 mg/kg) treated diabetic eNOS ko mice (n=17)
4) Linagliptin inhibitor (p.o. 3 mg/kg) treated diabetic eNOS ko mice (n=14)
5) Telmisartan (1 mg/kg) + Linagliptin (3 mg/kg) treated diabetic eNOS ko mice (n=12)

*, p< 0.05, student's test and Mann-Whitney U-rest

1) Non-diabetic eNOS ko control mice, placebo (natrosol) (n=14)
2) sham treated diabetic eNOS ko mice, placebo (natrosol) (n=17)
3) Telmisartan (p.o. 1 mg/kg) treated diabetic eNOS ko mice (n=17)
4) Linagliptin inhibitor (p.o. 3 mg/kg) treated diabetic eNOS ko mice (n=14)
5) Telmisartan (1 mg/kg) + Linagliptin (3 mg/kg) treated diabetic eNOS ko mice (n=12)

*, $p < 0.05$, student`s test and Mann-Whitney U-rest

| Ratio of changes in mRNA: control vs treated | Sham | 5/6N | 5/6N + Linagliptin |
|---|---|---|---|
| TGF-β | 0.83±0.02 | 0.93±0.05 | 0.80±0.10 |
| TIMP | 0.92±0.04 | 1.39±0.17 | 0.72±0.20 |
| Col1α | 0.61±0.06 | 0.83±0.03 | 0.76±0.05 |
| Col3α | 0.58±0.04 | 1.04±0.17 | 0.52±0.11 |
| BNP | 1.00±0.13 | 2.93±0.43 | 1.35±0.16 |

VASOPROTECTIVE AND CARDIOPROTECTIVE ANTIDIABETIC THERAPY

The present invention relates to certain DPP-4 inhibitors for treating and/or preventing oxidative stress, as well as to the use of such DPP-4 inhibitors in treatment and/or prevention of diabetic or non-diabetic patients, including patient groups at risk of cardiovascular and/or renal disease.

The present invention further relates to certain DPP-4 inhibitors for treating and/or preventing endothelial dysfunction.

The present invention further relates to certain DPP-4 inhibitors for use as antioxidants and/or anti-inflammatories.

The present invention further relates to certain DPP-4 inhibitors for treating and/or preventing oxidative stress, vascular stress and/or endothelial dysfunction (e.g. in diabetes or non-diabetes patients), particularly independently from or beyond glycemic control.

The present invention further relates to certain DPP-4 inhibitors for treating and/or preventing hyperglycemia-induced or -associated oxidative stress (e.g. beyond glycemic control), as well as to the use of such DPP-4 inhibitors in antidiabetic therapy.

The present invention further relates to certain DPP-4 inhibitors for treating and/or preventing metabolic diseases, such as diabetes, especially type 2 diabetes mellitus and/or diseases related thereto (e.g. diabetic complications), particularly in patients having or being at risk of oxidative stress, vascular stress and/or endothelial dysfunction, or diseases or conditions related or associated therewith.

Further, the present invention relates to certain DPP-4 inhibitors for treating and/or preventing metabolic diseases, such as diabetes, especially type 2 diabetes mellitus and/or diseases related thereto (e.g. diabetic complications), in patients having or being at risk of cardiovascular and/or renal disease, such as e.g. myocardial infarction, stroke or peripheral arterial occlusive disease and/or diabetic nephropathy, micro- or macroalbuminuria, or acute or chronic renal impairment.

Further, the present invention relates to certain DPP-4 inhibitors for treating and/or preventing metabolic diseases, such as diabetes, especially type 2 diabetes mellitus and/or diseases related thereto, in patients having or being at risk of micro- or macrovascular diabetic complications, such as e.g. diabetic retinopathy, diabetic neuropathy, diabetic nephropathy, or cardio- or cerebrovascular diseases (such as e.g. myocardial infarction, stroke or peripheral arterial occlusive disease).

Further, the present invention relates to certain DPP-4 inhibitors for modulating, blocking or reducing deleterious metabolic memory effect of (chronic or transient episodes of) hyperglycemia, particularly on diabetic complications.

Further, the present invention relates to certain DPP-4 inhibitors for treating, preventing or reducing risk for micro- or macrovascular diseases which may be induced, memorized by or associated with exposure to oxidative stress.

Furthermore, the present invention relates to a certain DPP-4 inhibitor for treating and/or preventing metabolic diseases, such as diabetes, especially type 2 diabetes mellitus and/or diseases related thereto (e.g. diabetic complications), in patients with or at risk of cardiovascular and/or renal disease, particularly in those type 2 diabetes patients being at risk of cardio- or cerebrovascular events, such as type 2 diabetes patients with one or more risk factors selected from A), B), C) and D):

A) previous or existing vascular disease (such as e.g. myocardial infarction (e.g. silent or non-silent), coronary artery disease, percutaneous coronary intervention, coronary artery by-pass grafting, ischemic or hemorrhagic stroke, congestive heart failure (e.g. NYHA class I or II, e.g. left ventricular function <40%), or peripheral occlusive arterial disease), B) vascular related end-organ damage (such as e.g. nephropathy, retinopathy, neuropathy, impaired renal function, chronic kidney disease, and/or micro- or macroalbuminuria), C) advanced age (such as e.g. age >/=60-70 years), and D) one or more cardiovascular risk factors selected from
  advanced type 2 diabetes mellitus (such as e.g. >10 years duration),
  hypertension (such as e.g. >130/80 mm Hg, or systolic blood pressure >140 mmHg or on at least one blood pressure lowering treatment),
  current daily cigarette smoking,
  dyslipidemia (such as e.g. atherogenic dyslipidemia, postprandial lipemia, or high level of LDL cholesterol (e.g. LDL cholesterol >/=130-135 mg/dL), low level of HDL cholesterol (e.g. <35-40 mg/dL in men or <45-50 mg/dL in women) and/or high level of triglycerides (e.g. >200-400 mg/dL) in the blood, or on at least one treatment for lipid abnormality),
  obesity (such as e.g. abdominal and/or visceral obesity, or body mass index >/=45 kg/m2),
  age >/=40 and </=80 years,
  metabolic syndrome, hyperinsulinemia or insulin resistance, and
  hyperuricemia, erectile dysfunction, polycystic ovary syndrome, sleep apnea, or family history of vascular disease or cardiomyopathy in first-degree relative, said method comprising administering a therapeutically effective amount of the DPP-4 inhibitor, optionally in combination with one or more other therapeutic substances, to the patient.

Moreover, the present invention relates to a certain DPP-4 inhibitor for use in a method of preventing, reducing the risk of or delaying the occurrence of cardio- or cerebrovascular events, such as cardiovascular death, (fatal or non-fatal) myocardial infarction (e.g. silent or non-silent MI), (fatal or non-fatal) stroke, or hospitalization (e.g. for acute coronary syndrome, leg amputation, (urgent) revascularization procedures, heart failure or for unstable angina pectoris), preferably in type 2 diabetes patients, particularly in those type 2 diabetes patients being at risk of cardio- or cerebrovascular events, such as type 2 diabetes patients with one or more risk factors selected from A), B), C) and D):

A) previous or existing vascular disease (such as e.g. myocardial infarction (e.g. silent or non-silent), coronary artery disease, percutaneous coronary intervention, coronary artery by-pass grafting, ischemic or hemorrhagic stroke, congestive heart failure (e.g. NYHA class I or II, e.g. left ventricular function <40%), or peripheral occlusive arterial disease), B) vascular related end-organ damage (such as e.g. nephropathy, retinopathy, neuropathy, impaired renal function, chronic kidney disease, and/or micro- or macroalbuminuria), C) advanced age (such as e.g. age >/=60-70 years), and D) one or more cardiovascular risk factors selected from
  advanced type 2 diabetes mellitus (such as e.g. >10 years duration), hypertension (such as e.g. >130/80 mm Hg, or systolic blood pressure >140 mmHg or on at least one blood pressure lowering treatment), current daily cigarette smoking, dyslipidemia (such as e.g. atherogenic dyslipidemia, postprandial lipemia, or high level of LDL cholersterol (e.g. LDL cholesterol >/=130-135 mg/dL), low level of HDL cholesterol (e.g. <35-40 mg/dL in men or <45-50 mg/dL in women) and/or high level of triglycerides (e.g. >200-400 mg/dL) in the blood, or on at least one treatment for lipid abnormality), obesity (such as e.g. abdominal and/or visceral obesity, or body mass index >/=45 kg/m2), age >/=40 and </=80 years, metabolic syndrome, hyperinsulinemia or insulin resistance, and hyperuricemia, erectile dysfunction, polycystic ovary syndrome, sleep apnea, or family history of vascular disease or cardiomyopathy in first-degree relative, said method comprising administering a therapeutically effective amount of the DPP-4 inhibitor, optionally in combination with one or more other therapeutic substances, to the patient.

Yet moreover, the present invention relates to a certain DPP-4 inhibitor for use in a method of preventing, reducing the risk of or delaying the occurrence of cardio- or cerebrovascular events, such as cardiovascular death, (fatal or non-fatal) myocardial infarction (e.g. silent or non-silent MI), (fatal or non-fatal) stroke, or hospitalization (e.g. for acute coronary syndrome, leg amputation, (urgent) revascularization procedures, heart failure or for unstable angina pectoris) in type 2 diabetes patients with vascular related end-organ damage, particularly nephropathy, impaired renal function, chronic kidney disease, micro- or macroalbuminuria, said method comprising administering a therapeutically effective amount of the DPP-4 inhibitor, optionally in combination with one or more other therapeutic substances, to the patient.

Yet moreover, the present invention relates to a certain DPP-4 inhibitor for use in a method of improving cognitive function (e.g. attenuating, reversing or treating cognitive decline), improving β-cell function (e.g. improving insulin secretion rate derived from a 3 h meal tolerance test, improving long term β-cell function), improving diurnal glucose pattern (e.g. improving ambulatory glucose profile, glycemic variability, biomarkers of oxidation, inflammation or endothelial function), and/or improving durability of glucose control according to β-cell autoantibody status (e.g., glutamic acid decarboxylase GAD), said method comprising administering a therapeutically effective amount of the DPP-4 inhibitor, optionally in combination with one or more other therapeutic substances, to the patient.

Yet moreover, the present invention relates to a certain DPP-4 inhibitor for use in a method of preventing, reducing the risk of, slowing the progression of, delaying the onset of, attenuating, reversing or treating cognitive dysfunction or cognitive decline, said method comprising administering a therapeutically effective amount of the DPP-4 inhibitor, optionally in combination with one or more other therapeutic substances, to the patient.

Yet moreover, the present invention relates to a certain DPP-4 inhibitor for use in a method of preventing, reducing the risk of, slowing the progression of, delaying the onset of, attenuating, reversing or treating latent autoimmune diabetes in adults (LADA), said method comprising administering a therapeutically effective amount of the DPP-4 inhibitor, optionally in combination with one or more other therapeutic substances, to the patient.

Further, the present invention relates to a certain DPP-4 inhibitor for use in a method (with the joint aims) of preventing, reducing the risk of, slowing the progression of, delaying the onset of, attenuating, reversing or treating cardio- or cerebrovascular disease or events (such as e.g. those described herein), and preventing, reducing the risk of, slowing the progression of, delaying the onset of, attenuating, reversing or treating diabetic nephropathy, in a patient in need thereof (such as e.g. a patient as described herein, especially a type 2 diabetes patient), said method comprising administering a therapeutically effective amount of the DPP-4 inhibitor, optionally in combination with one or more other therapeutic substances, to the patient.

Further, the present invention relates to one or more of the following methods of treating, reducing, preventing and/or protecting against oxidative stress, such as e.g. non-diabetes- or diabetes- (hyperglycemia-) induced or -associated oxidative stress;

treating, preventing, reducing the risk of, slowing the progression of, delaying the onset of, attenuating or reversing endothelial dysfunction or improving endothelial function;

treating, preventing, reducing the risk of, slowing the progression of, delaying the onset of, attenuating or reversing diseases or conditions associated with oxidative stress, such as those described herein;

treating, preventing, reducing the risk of, slowing the progression of, delaying the onset of, attenuating or reversing (renal, cardiac, cerebral or hepatic) ischemia/reperfusion injuries and/or reducing myocardial infarct size in the heart (e.g. after myocardial ischemia/reperfusion);

treating, preventing, reducing the risk of, slowing the progression of, delaying the onset of, attenuating or reversing (adverse) vascular remodeling such as cardiac remodeling (particularly after myocardial infarction), which may be characterized by cardiomyocyte hypertrophy, interstitial fibrosis, ventricular dilation, contractile dysfunction and/or cell death/apoptosis;

treating, preventing, reducing the risk of, slowing the progression of, delaying the onset of, attenuating or reversing chronic or acute renal failure and/or peripheral arterial occlusion;

treating, preventing, reducing the risk of, slowing the progression of, delaying the onset, attenuating or reversing congestive heart failure (e.g. NYHA class I, II, III or IV) and/or cardiac hypertrophy (e.g. left ventricular hypertrophy), and/or nephropathy and/or albuminuria;

treating, preventing, reducing the risk of, slowing the progression of, delaying the onset of, attenuating or reversing uremic cardiomyopathy, interstitial expansion and/or (cardiac) fibrosis (particularly in patients with chronic kidney and heart diseases often associated with type 2 diabetes);

modulating, blocking, preventing, reducing or protecting against deleterious metabolic memory effect of (chronic, early or transient episodes of) hyperglycemia, particularly on diabetic complications;

preventing or protecting against oxidation of atherogenic or pro-atherogenic low density lipoprotein (particularly, small dense LDL particles) and/or atherosclerotic plaque formation;

preventing or protecting against oxidative-stress induced impairment of function or viability of pancreatic beta cells;

treating, preventing, ameliorating or improving pancreatic islet inflammation or lipotoxicity and glucotoxicity in islets, or increasing beta cell/alpha cell ratio, protecting beta cell or normalizing/improving pancreatic islet morphology or function; and/or preventing, reducing the risk of, slowing the progression of, delaying the onset of, attenuating, reversing or treating complications of diabetes mellitus, such as micro- and macrovascular diseases, such as e.g. nephropathy, micro- or macroalbuminuria, proteinuria, retinopathy, cataracts, neuropathy, learning or memory impairment, neurodegenerative or cognitive disorders, cardio- or cerebrovascular diseases, endothelial dysfunction, tissue ischaemia, diabetic foot or ulcus, atherosclerosis, hypertension, myocardial infarction, acute coronary syndrome, unstable angina pectoris, stable angina pectoris, peripheral arterial occlusive disease, cardiomyopathy (including e.g. uremic cardiomyopathy), heart failure, heart rhythm disorders, vascular restenosis, and/ or stroke;

particularly independently from or beyond glycemic control;

in a patient in need thereof (e.g. type 1 diabetes, LADA or, especially, type 2 diabetes patient);

said methods comprising administering an effective amount of a certain DPP-4 inhibitor, optionally in combination with an effective amount of one or more other active substances to the patient.

Further, the present invention relates to a certain DPP-4 inhibitor for use in a method of preventing, reducing the risk of, slowing the progression of, delaying the onset of, attenuating, reversing or treating diabetic nephropathy, in a patient (such as e.g. a patient as described herein, especially a type 2 diabetes patient), who does not adequately respond to therapy with an angiotensin receptor blocker (ARB such as e.g. telmisartan), said method comprising administering a therapeutically effective amount of the DPP-4 inhibitor, optionally in combination with one or more other therapeutic substances (e.g. an ARB such as e.g. telmisartan), to the patient.

Features of diabetic nephropathy may include hyperfiltration (in early stage), micro- or macroalbuminuria, nephrotic syndrome, proteinuria, hypertension, fluid retention, edema, and/or progressively impaired or decreased kidney and renal filter function (e.g. glomerular filtration rate GFR) leading finally to renal failure or end-stage renal disease. Further features may include diffuse or nodular glomerulosclerosis, afferent and efferent hyaline arteriolosclerosis, and/or tubulointerstitial fibrosis and atrophy. Further features may include abnormal albumin/creatinine or protein/creatinine ratio and/or abnormal glomerular filtration rate.

The present invention further relates to a certain DPP-4 for use in a method of preventing or treating diabetic nephropathy in a patient with inadequate response to therapy with an angiotensin receptor blocker (ARB such as e.g. telmisartan). The method may comprise administering a therapeutically effective amount of the DPP-4 inhibitor and telmisartan to the patient.

Accordingly, in a particular embodiment, a preferred DPP-4 inhibitor within the meaning of this invention is linagliptin.

Pharmaceutical compositions or combinations for use in these therapies comprising the DPP-4 inhibitor as defined herein optionally together with one or more other active substances are also contemplated.

Further, the present invention relates to the DPP-4 inhibitors, optionally in combination with one, two or more further active agents, each as defined herein, for use in the therapies as described herein.

Further, the present invention relates to the use of the DPP-4 inhibitors, optionally in combination with one, two or more further active agents, each as defined herein, for preparing pharmaceutical compositions which are suitable for the treatment and/or prevention purposes of this invention.

Further, the present invention relates to a therapeutic (treatment or prevention) method as described herein, said method comprising administering an effective amount of a DPP-4 inhibitor as described herein and, optionally, one or more other active or therapeutic agents as described herein to the patient in need thereof.

BRIEF DESCRIPTION OF THE DRAWINGS

In FIG. 4, within each setting of inhibition of oxidative burst, the first bar from left refers to activation by LPS and the second bar refers to activation by Zymosan A.

In FIG. 6, within each setting of LPS stimulation, the first bar from left refers to w/o gliptin, the second bar refers to 1 µM BI 1356, the third bar refers to 10 µM BI 1356 and the fourth bar refers to 100 µM BI 1356.

FIG. 8A shows the effect of GTN induced endothelial dysfunction and linagliptin treatment on endothelium dependent relaxation (EtOH Ctr=ethanol control, GTN s.c.=glyceryl trinitrate—subcutaneous, BI1356=linagliptin).

FIG. 8B shows the effect of LPS (10 mg/kg/d i.p.) in vivo treatment and linagliptin treatment on endothelium-dependent relaxation (LPS=lipopolysaccharide, EtOH Ctr=control).

In FIG. 12, between time point 3 and time point 6, the first line from the top refers to placebo 2K1C (highest RR systolic), the second line from the top refers to linagliptin, the line in the middle refers to telmisartan, the second line from bottom refers to placebo sham, and the first line from bottom refers to telmisartan+linagliptin (lowest RR systolic).

DETAILED DESCRIPTION OF THE INVENTION

Figure 1:
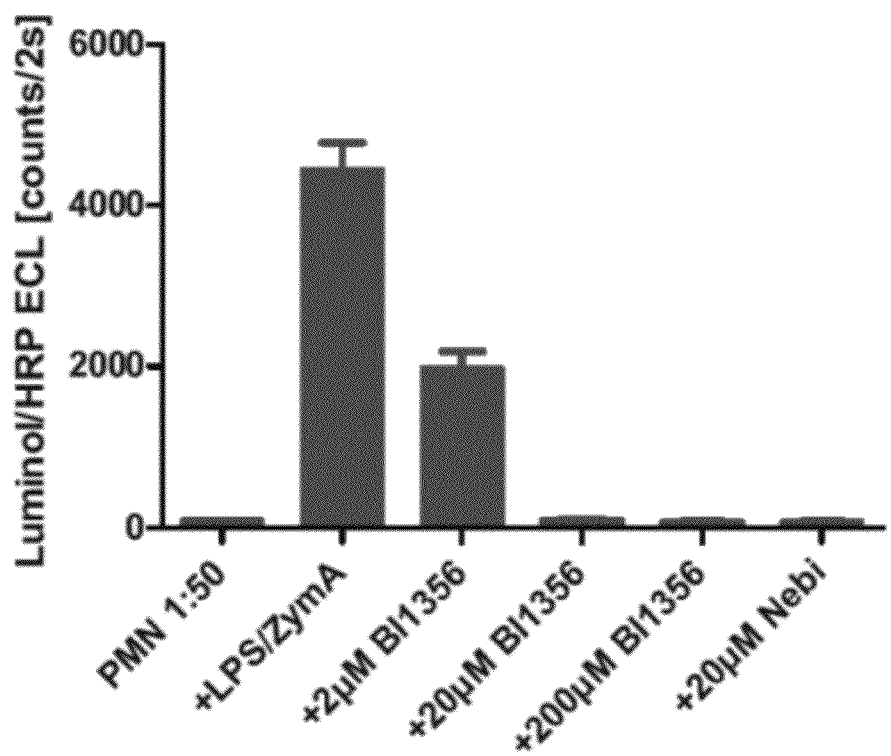
FIG. 1 shows the effect of linagliptin on zymosan A (ZymA) triggered ROS in human PMN (LPS=lipopolysaccharide, PMN=polymorphonuclear neutrophils, BI1356=linagliptin, Nebi=nebivolol).
Figure 2:
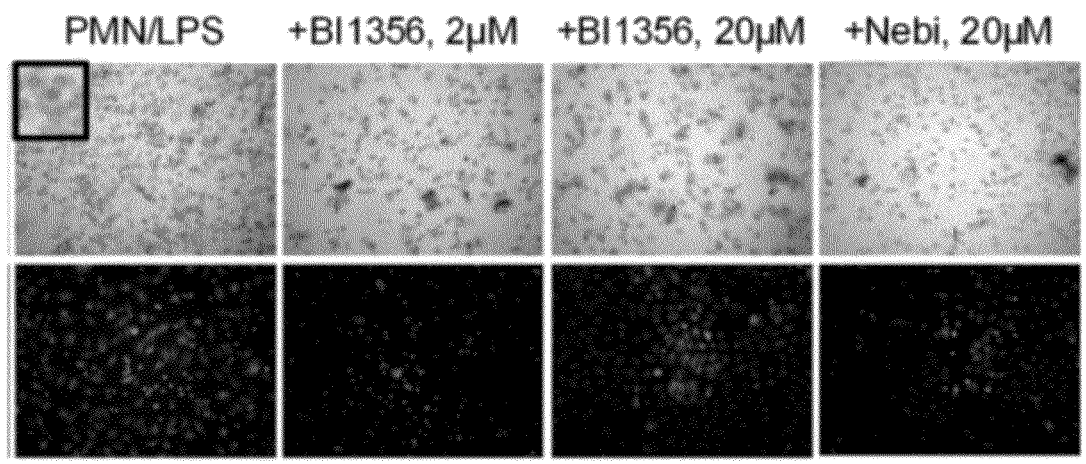
FIG. 2 shows the effect of linagliptin on adhesion of human leukocytes (PMN) on human endothelial cells following LPS stimulation (Turks and CF-DA staining, BI1356=linaglitptin).
Figure 3:
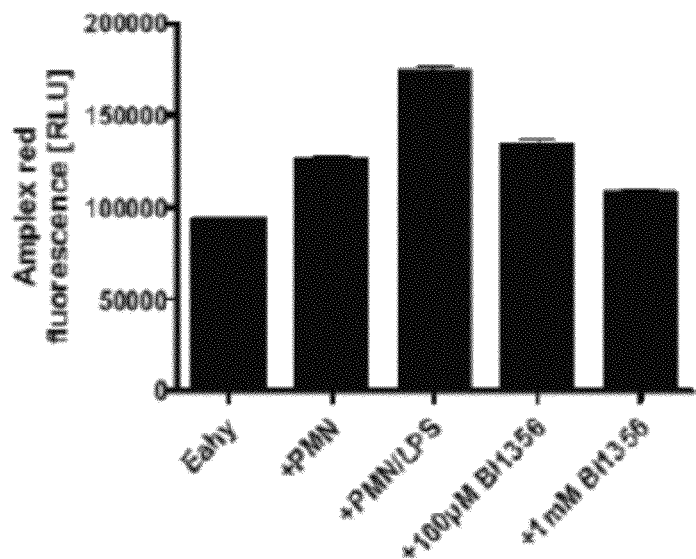
FIG. 3 shows the effect of linagliptin on LPS (50 µg/ml)-induced adhesion of neutrophils to EA.hy cells—measured by the oxidation of amplex red.
Figure 4:
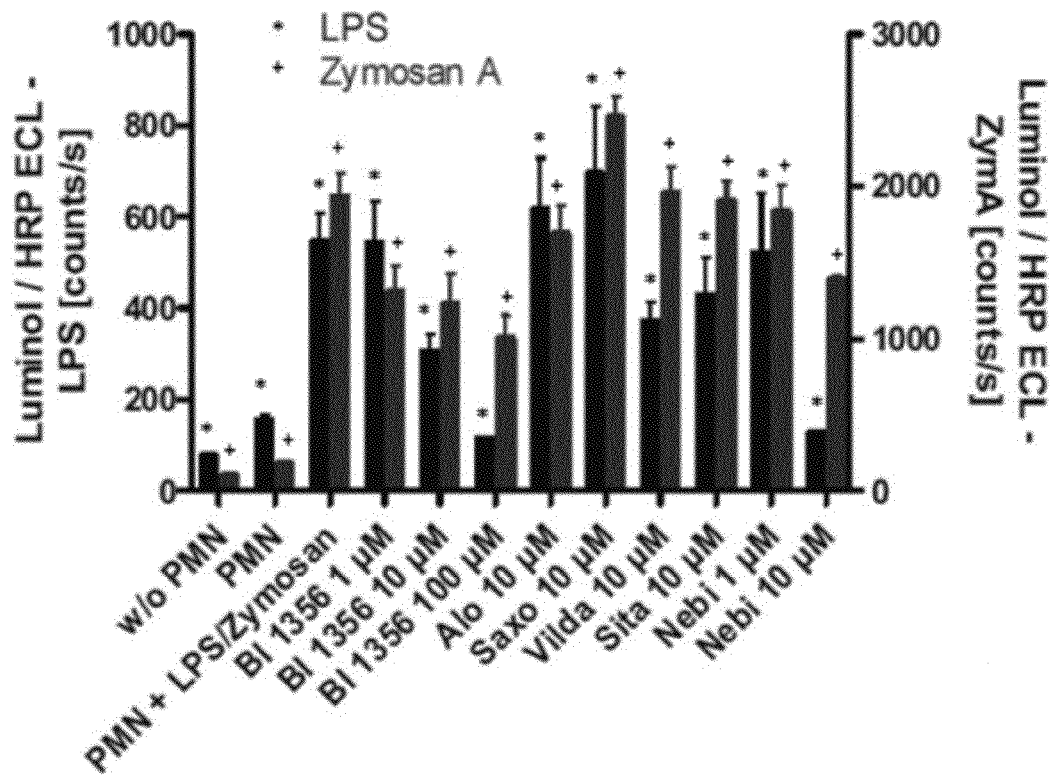
FIG. 4 shows the effect of gliptins on LPS/zymosan A-activated neutrophil driven oxidation of luminol/HRP-scavenging of peroxidase-derived ROS and inhibition of NADPH oxidase activity (LPS=lipopolysaccharide, PMN=polymorphonuclear neutrophils, BI1356=linagliptin, Alo=alogliptin, Vilda=vildagliptin, Saxo=saxagliptin, Sita=sitagliptin, Nebi=nebivolol).
Figures 5, 6:
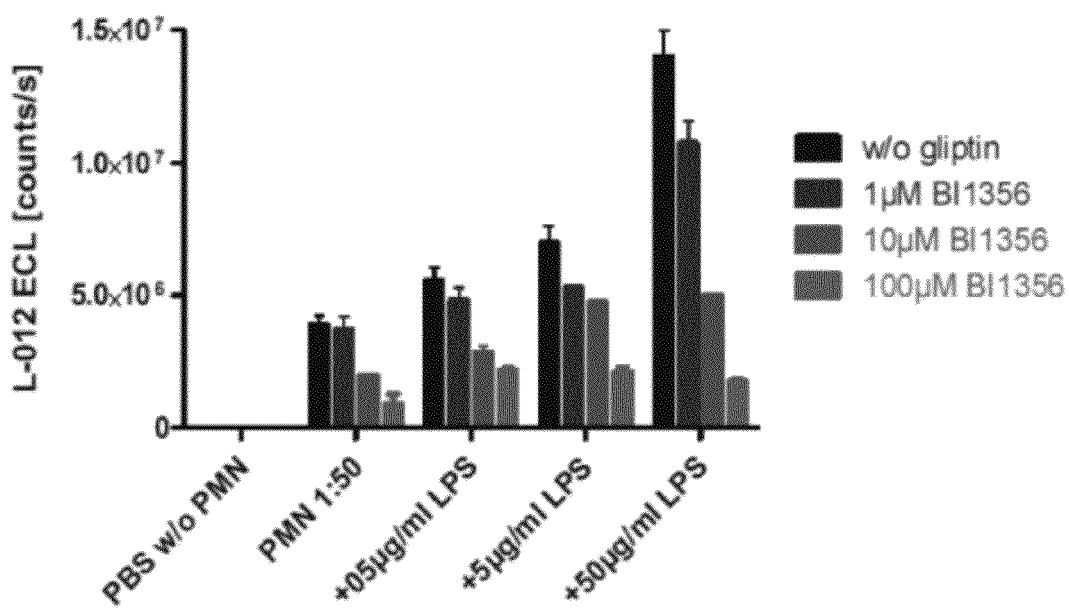
FIG. 5 is a table comparing gliptins on direct anti-oxidative effects in vitro.
FIG. 6 shows the effect of linagliptin on LPS-activated neutrophil driven oxidation of L-012-scavenging of peroxidase-derived ROS and inhibition of NADPH oxidase activity. Quantification of oxidative burst in isolated human PMN ($5 \times 10^5$ cells/ml) with increasing LPS and linagliptin concentrations by ECL using the luminol analogue L-012 (100 µM). (PBS=phosphate-buffered saline, LPS=lipopolysaccharide, PMN=polymorphonuclear neutrophils BI1356=linagliptin).

Oxidative stress represents an imbalance between the production of reactive oxygen species (which include free radicals, which typically have an oxygen- or nitrogen based unpaired electron in their outer orbitals and peroxides) and a biological system's ability to readily detoxify the reactive intermediates or to repair the resulting damage. Disturbances in the normal redox state of tissues can cause toxic effects through the production of peroxides and free radicals that damage all components of the cell, including proteins, lipides and nucleic acid/DNA. Oxidative stress can target many organs (such as blood vessels, eyes, heart, skin, kidney, joints, lung, brain, immune system, liver, or multi-organs) and can be involved in many diseases and conditions. Examples of such diseases or conditions associated with oxidative stress include atherosclerosis (e.g. platelet activation and atheromatous plaque formation), endothelial dysfunction, restenosis, hypertension, peripheral occlusive vascular disease, ischemia-reperfusion injuries (e.g. renal, hepatic, cardiac or cerebral ischemia-reperfusion injuries), fibrosis (e.g. renal, hepatic, cardiac or pulmonary fibrosis); macular degeneration, retinal degeneration, caterocts, retinopathy; coronary heart disease, ischemia, myocardial infarction; psoriasis, dermatitis; chronic kidney disease, nephritis, acute renal failure, glomerulonephritis, nephropathy; rheumatoid arthritis, osteoarthritis; asthma, COPD, respiratory distress syndrome; stroke, neurodegenerative diseases (e.g. Alzheimer's disease, Parkinson's disease, Huntington's disease), schizophrenia, bipolar disorder, obsessive compulsive disorder; chronic systemic inflammations, perivascular inflammation, autoimmune disorders, multiple sclerosis, lupus erythematosus, inflammatory bowel disease, ulcerative colitis; NAFLD/NASH; chronic fatigue syndrome, polycystic ovary syndrome, sepsis, diabetes, metabolic syndrome, insulin resistance, hyperglycemia, hyperinsulinemia, dyslipidemia, hypercholesterolemia, hyperlipidemia, etc. In addition to their original pharmacological properties, certain drugs used clinically, including, without being limited, anti-hypertension agents, angiotensin receptor blockers and antihyperlipidemic agents such as statins, protect various organs via antioxidative stress mechanisms.

Patients with or at risk of oxidative and/or vascular stress can be diagnosed by determining patient's oxidative stress markers, such as e.g. oxidized LDL, markers of inflammatory status (e.g. pro-inflammatory interleukins), 8-OHdG, isoprostanes (e.g. F2-isoprostanes, 8-iso-prostaflandin F2alpha), nitrotyrosine, or N-carboxymethyl lysine (CML).

Endothelial dysfunction, commonly assessed clinically as impaired endothelium-dependent vasomotion (e.g. imbalance between vasodilating and vasoconstricting), is a physiological disability of endothelial cells, the cells that line the inner surface of blood vessels, arteries and veins, that prevents them from carrying out their normal biochemical functions. Normal endothelial cells are involved in mediating the processes of coagulation, platelet adhesion, immune function, control of volume and electrolyte content of the intravascular and extravascular spaces. Endothelial dysfunction is associated with proinflammatory, pro-oxidative and pro-thrombotic changes within the arterial wall. Endothelial dysfunction is thought to be a key event in the development and progression of atherosclerosis and arterial stiffness, and predates clinically obvious vascular complications. Endothelial dysfunction is of prognostic significance in detecting vascular disease and predicting adverse vascular events.

Risk factors for atherosclerosis and vascular disease/events are associated with endothelial dysfunction. Endothelial damage also contributes to the development of renal injury and/or chronic or progressive kidney damages, such as e.g. tubulointerstitial fibrosis, glomerulonephritis, micro- or macroalbuminuria, nephropathy and/or chronic kidney disease or renal failure. There is supporting evidence that oxidative stress does not only contribute to endothelial dysfunction or damage but also to vascular disease.

Type 2 diabetes mellitus is a common chronic and progressive disease arising from a complex pathophysiology involving the dual endocrine effects of insulin resistance and impaired insulin secretion with the consequence not meeting the required demands to maintain plasma glucose levels in the normal range. This leads to hyperglycaemia and its associated micro- and macrovascular complications or chronic damages, such as e.g. diabetic nephropathy, retinopathy or neuropathy, or macrovascular (e.g. cardio- or cerebro-vascular) complications. The vascular disease component plays a significant role, but is not the only factor in the spectrum of diabetes associated disorders. The high frequency of complications leads to a significant reduction of life expectancy. Diabetes is currently the most frequent cause of adult-onset loss of vision, renal failure, and amputation in the Industrialized World because of diabetes induced complications and is associated with a two to five fold increase in cardiovascular disease risk.

Large randomized studies have established that intensive and tight glycemic control during early (newly diagnoses to 5 years) stage diabetes has enduring beneficial effects and reduces the risk of diabetic complications, both micro- and macrovascular. However, many patients with diabetes still develop diabetic complications despite receiving intensified glycemic control.

Epidemiological and prospective data support a long-term influence of early (newly diagnosed to 5 years) metabolic control on clinical outcomes. It has been found that hyperglycemia has long-lasting deleterious effects both in type 1 and type 2 diabetes and that glycemic control, if not started at a very early stage of the disease or not intensively or not tightly provided, may not be enough to completely reduce complications.

It has been further found that transient episodes of hyperglycemia (e.g. hyperglycemic events), can induce molecular changes, and that these changes can persist or are irreversible after return to normoglycemia.

Collectively, these data suggest that metabolic memories are stored early in the course of diabetes and that, in certain diabetic conditions, oxidative and/or vascular stresses can persist after glucose normalization. This phenomenon that early glycemic environment, and/or even transient hyperglycemia, is remembered with clinical consequences in the target end organs (e.g. blood vessels, retina, kidney, heart, extremities) has recently been termed as 'metabolic memory.'

Potential mechanisms for propagating this 'memory' are certain epigenetic changes, the non-enzymatic glycation of cellular proteins and lipids (e.g. formation of advanced glycation end-products), oxidatively modified atherogenic lipoproteins, and/or an excess of cellular reactive oxygen and nitrogen species (RONS), in particular originated at the level of glycated-mitochondrial proteins, perhaps acting in concert with one another to maintain stress signalling.

Mitochondria are one of major sources of reactive oxygen species (ROS) in cells. Mitochondrial dysfunction increases electron leak and the generation of ROS from the mitochondrial respiratory chain (MRC). High levels of glucose and lipids impair the activities of MRC complex enzymes. For example, the MRC enzyme NADPH oxidase generates superoxide from NADPH in cells. Increased NADPH oxidase activity can be detected in diabetic patients.

Further, there is evidence that overproduction of free radicals, such as e.g. reactive oxygen species (ROS), contributes to oxidative and vascular stress after glucose normalization and to developing and/or maintaining the metabolic memory, and thus to the unifying link between hyperglycemia and cellular memory effects, such as e.g. in endothelial dysfunction or other complications of diabetes.

Thus, mainly related to persisting (long-term) oxidative stress induced by or associated with (chronic, early or transient episodes of) hyperglycemia, there are certain metabolic conditions in that, even normalizing glycemia, a long-term persistent activation of many pathways involved in the pathogenesis of diabetic complications can still be present. One of the major findings in the course of diabetes has thereby been the demonstration that even in normoglycemia and independent of the actual glycemic levels an overproduction of free radicals can still be evident. For example, endothelial dysfunction (a causative marker of diabetic vascular complications) can persist even after normalizing glycemia. However, there is evidence that combining antioxidant therapy with normalization of glycemia can be used to almost interrupt endothelial dysfunction.

Therefore, treating oxidative and/or vascular stress particularly beyond glycemic control, such as by the reduction of cellular reactive species and/or of glycation (e.g. by inhibition of the production of free oxygen and nitrogen radicals), preferably independently of glycemic status, may beneficially modulate, reduce, block or protect against the memory effect of hyperglycemia and reduce the risk, prevent, treat or delay the onset of long-term diabetic complications, particularly such ones which are associated with or induced by oxidative stress, in patients in need thereof.

The treatment of type 2 diabetes typically begins with diet and exercise, followed by oral antidiabetic monotherapy, and although conventional monotherapy may initially control blood glucose in some patients, it is however associated with a high secondary failure rate. The limitations of single-agent therapy for maintaining glycemic control may be overcome, at least in some patients, and for a limited period of time by combining multiple drugs to achieve reductions in blood glucose that cannot be sustained during long-term therapy with single agents. Available data support the conclusion that in most patients with type 2 diabetes current monotherapy will fail and treatment with multiple drugs will be required. But, because type 2 diabetes is a progressive disease, even patients with good initial responses to conventional combination therapy will eventually require an increase of the dosage or further treatment with insulin because the blood glucose level is very difficult to maintain stable for a long period of time. Although existing combination therapy has the potential to enhance glycemic control, it is not without limitations (especially with regard to long term efficacy). Further, traditional therapies may show an increased risk for side effects, such as hypoglycemia or weight gain, which may compromise their efficacy and acceptability.

Thus, for many patients, these existing drug therapies result in progressive deterioration in metabolic control despite treatment and do not sufficiently control metabolic status especially over long-term and thus fail to achieve and to maintain glycemic control in advanced or late stage type 2 diabetes, including diabetes with inadequate glycemic control despite conventional oral or non-oral antidiabetic medication.

Therefore, although intensive treatment of hyperglycemia can reduce the incidence of chronic damages, many patients with type 2 diabetes remain inadequately treated, partly because of limitations in long term efficacy, tolerability and dosing inconvenience of conventional antihyperglycemic therapies.

This high incidence of therapeutic failure is a major contributor to the high rate of long-term hyperglycemia-associated complications or chronic damages (including micro- and macrovascular complications such as e.g. diabetic nephropathy, retinopathy or neuropathy, or cerebro- or cardiovascular complications such as e.g. myocardial infarction, stroke or vascular mortality or morbidity) in patients with type 2 diabetes.

Oral antidiabetic drugs conventionally used in therapy (such as e.g. first- or second-line, and/or mono- or (initial or add-on) combination therapy) include, without being restricted thereto, metformin, sulphonylureas, thiazolidinediones, glinides and α-glucosidase inhibitors.

Non-oral (typically injected) antidiabetic drugs conventionally used in therapy (such as e.g. first- or second-line, and/or mono- or (initial or add-on) combination therapy) include, without being restricted thereto, GLP-1 or GLP-1 analogues, and insulin or insulin analogues.

However, the use of these conventional antidiabetic or antihyperglycemic agents can be associated with various adverse effects. For example, metformin can be associated with lactic acidosis or gastrointestinal side effects; sulfonylureas, glinides and insulin or insulin analogues can be associated with hypoglycemia and weight gain; thiazolidinediones can be associated with edema, bone fracture, weight gain and heart failure/cardiac effects; and alpha-glucosidase blockers and GLP-1 or GLP-1 analogues can be associated with gastrointestinal adverse effects (e.g. dyspepsia, flatulence or diarrhea, or nausea or vomiting) and, most seriously (but rare), pancreatitis.

Therefore, it remains a need in the art to provide efficacious, safe and tolerable antidiabetic therapies.

Further, within the therapy of type 2 diabetes, it is a need for treating the condition effectively, avoiding the complications inherent to the condition, and delaying disease progression, e.g. in order to achieve a long-lasting therapeutic benefit.

Furthermore, it remains a need that antidiabetic treatments not only prevent the long-term complications often found in advanced stages of diabetes disease, but also are a therapeutic option in those diabetes patients who have developed or are at risk of developing complications, such as renal impairment.

Moreover, it remains a need to provide prevention or reduction of risk for adverse effects associated with conventional antidiabetic therapies.

The enzyme DPP-4 (dipeptidyl peptidase IV) also known as CD26 is a serine protease known to lead to the cleavage of a dipeptide from the N-terminal end of a number of proteins having at their N-terminal end a prolin or alanin residue. Due to this property DPP-4 inhibitors interfere with the plasma level of bioactive peptides including the peptide GLP-1 and are considered to be promising drugs for the treatment of diabetes mellitus.

For example, DPP-4 inhibitors and their uses are disclosed in WO 2002/068420, WO 2004/018467, WO 2004/018468, WO 2004/018469, WO 2004/041820, WO 2004/046148, WO 2005/051950, WO 2005/082906, WO 2005/063750, WO 2005/085246, WO 2006/027204, WO 2006/029769, WO2007/014886; WO 2004/050658, WO 2004/111051, WO 2005/058901, WO 2005/097798; WO 2006/068163, WO 2007/071738, WO 2008/017670; WO 2007/128721, WO 2007/128724, WO 2007/128761, or WO 2009/121945.

In the monitoring of the treatment of diabetes mellitus the HbA1c value, the product of a non-enzymatic glycation of the haemoglobin B chain, is of exceptional importance. As its formation depends essentially on the blood sugar level and the life time of the erythrocytes the HbA1c in the sense of a "blood sugar memory" reflects the average blood sugar level of the preceding 4-12 weeks. Diabetic patients whose HbA1c level has been well controlled over a long time by more intensive diabetes treatment (i.e. <6.5% of the total haemoglobin in the sample) are significantly better protected from diabetic microangiopathy. The available treatments for diabetes can give the diabetic an average improvement in their HbA1c level of the order of 1.0-1.5%. This reduction in the HbA1C level is not sufficient in all diabetics to bring them into the desired target range of <7.0%, preferably <6.5% and more preferably <6% HbA1c.

Within the meaning of this invention, inadequate or insufficient glycemic control means in particular a condition wherein patients show HbA1c values above 6.5%, in particular above 7.0%, even more preferably above 7.5%, especially above 8%. An embodiment of patients with inadequate or insufficient glycemic control include, without being limited to, patients having a HbA1c value from 7.5 to 10% (or, in another embodiment, from 7.5 to 11%). A special sub-embodiment of inadequately controlled patients refers to patients with poor glycemic control including, without being limited, patients having a HbA1c value 9%.

Within glycemic control, in addition to improvement of the HbA1c level, other recommended therapeutic goals for type 2 diabetes mellitus patients are improvement of fasting plasma glucose (FPG) and of postprandial plasma glucose (PPG) levels to normal or as near normal as possible. Recommended desired target ranges of preprandial (fasting) plasma glucose are 70-130 mg/dL (or 90-130 mg/dL) or <110 mg/dL, and of two-hour postprandial plasma glucose are <180 mg/dL or <140 mg/dL.

In one embodiment, diabetes patients within the meaning of this invention may include patients who have not previously been treated with an antidiabetic drug (drug-naïve patients). Thus, in an embodiment, the therapies described herein may be used in naïve patients. In another embodiment, diabetes patients within the meaning of this invention may include patients with advanced or late stage type 2 diabetes mellitus (including patients with failure to conventional antidiabetic therapy), such as e.g. patients with inadequate glycemic control on one, two or more conventional oral and/or non-oral antidiabetic drugs as defined herein, such as e.g. patients with insufficient glycemic control despite (mono-) therapy with metformin, a thiazolidinedione (particularly pioglitazone), a sulphonylurea, a glinide, GLP-1 or GLP-1 analogue, insulin or insulin analogue, or an α-glucosidase inhibitor, or despite dual combination therapy with metformin/sulphonylurea, metformin/thiazolidinedione (particularly pioglitazone), sulphonylurea/α-glucosidase inhibitor, pioglitazone/sulphonylurea, metformin/insulin, pioglitazone/insulin or sulphonylurea/insulin. Thus, in an embodiment, the therapies described herein may be used in patients experienced with therapy, e.g. with conventional oral and/or non-oral antidiabetic mono- or dual or triple combination medication as mentioned herein.

A further embodiment of diabetic patients within the meaning of this invention refers to patients ineligible for metformin therapy including
  patients for whom metformin therapy is contraindicated, e.g. patients having one or more contraindications against metformin therapy according to label, such as for example patients with at least one contraindication selected from:
    renal disease, renal impairment or renal dysfunction (e.g., as specified by product information of locally approved metformin), dehydration,
unstable or acute congestive heart failure,
acute or chronic metabolic acidosis, and
hereditary galactose intolerance; and
patients who suffer from one or more intolerable side effects attributed to metformin, particularly gastrointestinal side effects associated with metformin, such as for example patients suffering from at least one gastrointestinal side effect selected from:
nausea,
vomiting,
diarrhea,
intestinal gas, and
severe abdominal discomfort.

A further embodiment of the diabetes patients which may be amenable to the therapies of this invention may include, without being limited, those diabetes patients for whom normal metformin therapy is not appropriate, such as e.g. those diabetes patients who need reduced dose metformin therapy due to reduced tolerability, intolerability or contraindication against metformin or due to (mildly) impaired/reduced renal function (including elderly patients, such as e.g. ≥60-65 years).

A further embodiment of diabetic patients within the meaning of this invention refers to patients having renal disease, renal dysfunction, or insufficiency or impairment of renal function (including mild, moderate and severe renal impairment), e.g. as suggested by elevated serum creatinine levels (e.g. serum creatinine levels above the upper limit of normal for their age, e.g. ≥130-150 µmol/l, or ≥1.5 mg/dl (≥136 µmol/l) in men and ≥1.4 mg/dl (≥124 µmol/l) in women) or abnormal creatinine clearance (e.g. glomerular filtration rate (GFR) ≤30-60 ml/min).

In this context, for more detailed example, mild renal impairment may be e.g. suggested by a creatinine clearance of 50-80 ml/min (approximately corresponding to serum creatine levels of ≤1.7 mg/dL in men and ≤1.5 mg/dL in women); moderate renal impairment may be e.g. suggested by a creatinine clearance of 30-50 ml/min (approximately corresponding to serum creatinine levels of >1.7 to ≤3.0 mg/dL in men and >1.5 to ≤2.5 mg/dL in women); and severe renal impairment may be e.g. suggested by a creatinine clearance of <30 ml/min (approximately corresponding to serum creatinine levels of >3.0 mg/dL in men and >2.5 mg/dL in women). Patients with end-stage renal disease require dialysis (e.g. hemodialysis or peritoneal dialysis).

For other more detailed example, patients with renal disease, renal dysfunction or renal impairment include patients with chronic renal insufficiency or impairment, which can be stratified according to glomerular filtration rate (GFR, ml/min/1.73 m$^2$) into 5 disease stages: stage 1 characterized by normal GFR ≥90 plus either persistent albuminuria or known structural or hereditary renal disease; stage 2 characterized by mild reduction of GFR (GFR 60-89) describing mild renal impairment; stage 3 characterized by moderate reduction of GFR (GFR 30-59) describing moderate renal impairment; stage 4 characterized by severe reduction of GFR (GFR 15-29) describing severe renal impairment; and terminal stage 5 characterized by requiring dialysis or GFR <15 describing established kidney failure (end-stage renal disease, ESRD).

A further embodiment of diabetic patients within the meaning of this invention refers to type 2 diabetes patients with or at risk of developing micro- or macrovascular diabetic complications, such as e.g. described herein (e.g. such at-risk patients as described as follows).

A further embodiment of diabetic patients within the meaning of this invention refers to type 2 diabetes patients with or at risk of developing renal complications, such as diabetic nephropathy (including chronic and progressive renal insufficiency, albuminuria, proteinuria, fluid retention in the body (edema) and/or hypertension).

A further embodiment of the diabetes patients which may be amenable to the therapies of this invention may include, without being limited, those type 2 diabetes patients with or at risk of developing retinal complications, such as diabetic retinopathy.

A further embodiment of the diabetes patients which may be amenable to the therapies of this invention may include, without being limited, those type 2 diabetes patients with or at risk of developing macrovascular complications, such as myocardial infarction, coronary artery disease, ischemic or hemorrhagic stroke, and/or peripheral occlusive arterial disease.

A further embodiment of the diabetes patients which may be amenable to the therapies of this invention may include, without being limited, those type 2 diabetes patients with or at risk of cardio- or cerebrovascular diseases or events (such as e.g. those cardiovascular risk patients described herein).

A further embodiment of the diabetes patients which may be amenable to the therapies of this invention may include, without being limited, those diabetes patients (especially type 2 diabetes) with advanced age and/or with advanced diabetes disease, such as e.g. patients on insulin treatment, patients on triple antidiabetic oral therapy, patients with pre-existing cardio- and/or cerebrovascular events and/or patients with advanced disease duration (e.g. >/=5 to 10 years).

A further embodiment of the diabetes patients which may be amenable to the therapies of this invention may include, without being limited, those diabetes patients (especially type 2 diabetes patients) with one or more cardiovascular risk factors selected from A), B), C) and D):

A) previous or existing vascular disease (such as e.g. myocardial infarction (e.g. silent or non-silent), coronary artery disease, percutaneous coronary intervention, coronary artery by-pass grafting, ischemic or hemorrhagic stroke, congestive heart failure (e.g. NYHA class I or II, e.g. left ventricular function <40%), or peripheral occlusive arterial disease), B) vascular related end-organ damage (such as e.g. nephropathy, retinopathy, neuropathy, impaired renal function, chronic kidney disease, and/or micro- or macroalbuminuria), C) advanced age (such as e.g. age >/=60-70 years), and D) one or more cardiovascular risk factors selected from
advanced type 2 diabetes mellitus (such as e.g. >10 years duration),
hypertension (such as e.g. >130/80 mm Hg, or systolic blood pressure >140 mmHg or on at least one blood pressure lowering treatment),
current daily cigarette smoking,
dyslipidemia (such as e.g. atherogenic dyslipidemia, postprandial lipemia, or high level of LDL cholesterol (e.g. LDL cholesterol >/=130-135 mg/dL), low level of HDL cholesterol (e.g. <35-40 mg/dL in men or <45-50 mg/dL in women) and/or high level of triglycerides (e.g. >200-400 mg/dL) in the blood, or on at least one treatment for lipid abnormality),
obesity (such as e.g. abdominal and/or visceral obesity, or body mass index >/=45 kg/m2),
age >/=40 and </=80 years,
metabolic syndrome, hyperinsulinemia or insulin resistance, and hyperuricemia, erectile dysfunction, polycystic ovary syndrome, sleep apnea, or family history of vascular disease or cardiomyopathy in first-degree relative.

In certain embodiments, the patients which may be amenable to to the therapies of this invention may have or are at-risk of one or more of the following diseases, disorders or conditions: type 1 diabetes, type 2 diabetes, impaired glucose tolerance (IGT), impaired fasting blood glucose (IFG), hyperglycemia, postprandial hyperglycemia, postabsorptive hyperglycemia, latent autoimmune diabetes in adults (LADA), overweight, obesity, dyslipidemia, hyperlipidemia, hypercholesterolemia, hypertriglyceridemia, hyperNEFA-emia, postprandial lipemia, hypertension, atherosclerosis, endothelial dysfunction, osteoporosis, chronic systemic inflammation, non alcoholic fatty liver disease (NAFLD), polycystic ovarian syndrome, metabolic syndrome, nephropathy, micro- or macroalbuminuria, proteinuria, retinopathy, cataracts, neuropathy, learning or memory impairment, neurodegenerative or cognitive disorders, cardio- or cerebrovascular diseases, tissue ischaemia, diabetic foot or ulcus, atherosclerosis, hypertension, endothelial dysfunction, myocardial infarction, acute coronary syndrome, unstable angina pectoris, stable angina pectoris, peripheral arterial occlusive disease, cardiomyopathy (including e.g. uremic cardiomyopathy), heart failure, cardiac hypertrophy, heart rhythm disorders, vascular restenosis, stroke, (renal, cardiac, cerebral or hepatic) ischemia/reperfusion injuries, (renal, cardiac, cerebral or hepatic) fibrosis, (renal, cardiac, cerebral or hepatic) vascular remodeling; a diabetic disease, especially type 2 diabetes, mellitus may be preferred (e.g. as underlying disease).

In a further embodiment, the patients which may be amenable to to the therapies of this invention have a diabetic disease, especially type 2 diabetes mellitus, and may have or are at-risk of one or more other diseases, disorders or conditions, such as e.g. selected from those mentioned immediately above.

Within the scope of the present invention it has now been found that certain DPP-4 inhibitors as defined herein, optionally in combination with one or more other therapeutic substances (e.g. selected from those described herein), as well as pharmaceutical combinations, compositions or combined uses according to this invention of such DPP-4 inhibitors as defined herein have properties, which make them suitable for the purpose of this invention and/or for fulfilling one or more of above needs.

The present invention thus relates to a certain DPP-4 inhibitor as defined herein, preferably linagliptin (BI 1356), for use in the therapies described herein.

The present invention further relates to a certain DPP-4 inhibitor as defined herein, preferably linagliptin (BI 1356), in combination with metformin, for use in the therapies described herein.

The present invention further relates to a certain DPP-4 inhibitor as defined herein, preferably linagliptin (BI 1356), in combination with pioglitazone, for use in the therapies described herein.

The present invention further relates to a certain DPP-4 inhibitor as defined herein, preferably linagliptin (BI 1356), in combination with telmisartan, for use in the therapies described herein.

The present invention further relates to a pharmaceutical composition comprising a certain DPP-4 inhibitor as defined herein, preferably linagliptin (BI 1356), for use in the therapies described herein.

The present invention further relates to a pharmaceutical composition comprising a certain DPP-4 inhibitor as defined herein, preferably linagliptin (BI 1356), and metformin, for use in the therapies described herein.

The present invention further relates to a pharmaceutical composition comprising a certain DPP-4 inhibitor as defined herein, preferably linagliptin (BI 1356), and pioglitazone, for use in the therapies described herein.

The present invention further relates to a combination comprising a certain DPP-4 inhibitor (particularly BI 1356) and one or more other active substances selected from those mentioned herein, e.g. selected from other antidiabetic substances, active substances that lower the blood sugar level, active substances that lower the lipid level in the blood, active substances that raise the HDL level in the blood, active substances that lower blood pressure, active substances that are indicated in the treatment of atherosclerosis or obesity, anti-platelet agents, anticoagulant agents, and vascular endothelial protective agents, e.g. each as described herein; particularly for simultaneous, separate or sequential use in the therapies described herein.

The present invention further relates to a combination comprising a certain DPP-4 inhibitor (particularly BI 1356) and one or more other antidiabetics selected from the group consisting of metformin, a sulphonylurea, nateglinide, repaglinide, a thiazolidinedione, a PPAR-gamma-agonist, an alpha-glucosidase inhibitor, insulin or an insulin analogue, and GLP-1 or a GLP-1 analogue, particularly for simultaneous, separate or sequential use in the therapies described herein, optionally in combination with telmisartan.

The present invention further relates to a method for treating and/or preventing metabolic diseases, especially type 2 diabetes mellitus and/or conditions related thereto (e.g. diabetic complications) comprising the combined (e.g. simultaneous, separate or sequential) administration of an effective amount of one or more other antidiabetics selected from the group consisting of metformin, a sulphonylurea, nateglinide, repaglinide, a thiazolidinedione, a PPAR-gamma-agonist, an alpha-glucosidase inhibitor, insulin or an insulin analogue, and GLP-1 or a GLP-1 analogue, and of an effective amount of a DPP-4 inhibitor (particularly BI 1356) as defined herein, and, optionally, of an effective amount of telmisartan, to the patient (particularly human patient) in need thereof, such as e.g. a patient as described herein, including at-risk patient groups.

The present invention further relates to therapies or therapeutic methods described herein, such as e.g. a method for treating and/or preventing metabolic diseases, especially type 2 diabetes mellitus and/or conditions related thereto (e.g. diabetic complications), comprising administering a therapeutically effective amount of linagliptin (BI 1356) and, optionally, one or more other therapeutic agents, such as e.g. antidiabetics selected from the group consisting of metformin, a sulphonylurea, nateglinide, repaglinide, a thiazolidinedione, a PPAR-gamma-agonist, an alpha-glucosidase inhibitor, insulin or an insulin analogue, and GLP-1 or a GLP-1 analogue, and/or telmisartan, to the patient (particularly human patient) in need thereof, such as e.g. a patient as described herein (e.g. at-risk patient as described herein).

The present invention further relates to therapies or therapeutic methods described herein, such as e.g. a method for treating and/or preventing metabolic diseases, especially type 2 diabetes mellitus and/or conditions related thereto (e.g. diabetic complications), comprising administering a therapeutically effective amount of linagliptin (BI 1356) to the patient (particularly human patient) in need thereof, such as e.g. a patient as described herein, including at-risk patient (particularly such a patient with or at-risk of cardio- or cerebrovascular diseases or events and/or with or at-risk of renal diseases) as described herein.

The present invention further relates to therapies or therapeutic methods described herein, such as e.g. a method for treating and/or preventing metabolic diseases, especially type 2 diabetes mellitus and/or conditions related thereto (e.g. diabetic complications), comprising administering a therapeutically effective amount of linagliptin (BI 1356) and metformin to the patient (particularly human patient) in need thereof, such as e.g. a patient as described herein, including at-risk patient (particularly such a patient with or at-risk of cardio- or cerebrovascular diseases or events) as described herein.

The present invention further relates to therapies or therapeutic methods described herein, such as e.g. a method for treating and/or preventing metabolic diseases, especially type 2 diabetes mellitus and/or conditions related thereto (e.g. diabetic complications), comprising administering a therapeutically effective amount of linagliptin (BI 1356) and telmisartan to the patient (particularly human patient) in need thereof, such as e.g. a patient as described herein, including at-risk patient (particularly such a patient with or at-risk of cardio- or cerebrovascular diseases or events and/or at-risk of renal diseases) as described herein.

Examples of such metabolic disorders or diseases amenable by the therapy of this invention, particularly in the patients having or being at risk of cardiovascular and/or renal disease, may include, without being limited to, type 1 diabetes, type 2 diabetes, impaired glucose tolerance (IGT), impaired fasting blood glucose (IFG), hyperglycemia, postprandial hyperglycemia, postabsorptive hyperglycemia, latent autoimmune diabetes in adults (LADA), overweight, obesity, dyslipidemia, hyperlipidemia, hypercholesterolemia, hypertriglyceridemia, hyperNEFA-emia, postprandial lipemia, hypertension, atherosclerosis, endothelial dysfunction, osteoporosis, chronic systemic inflammation, non alcoholic fatty liver disease (NAFLD), retinopathy, neuropathy, nephropathy, polycystic ovarian syndrome, and/or metabolic syndrome.

The present invention further relates to at least one of the following methods:
- preventing, slowing the progression of, delaying or treating a metabolic disorder or disease, such as e.g. type 1 diabetes mellitus, type 2 diabetes mellitus, impaired glucose tolerance (IGT), impaired fasting blood glucose (IFG), hyperglycemia, postprandial hyperglycemia, postabsorptive hyperglycemia, latent autoimmune diabetes in adults (LADA), overweight, obesity, dyslipidemia, hyperlipidemia, hypercholesterolemia, hypertriglyceridemia, hyperNEFA-emia, postprandial lipemia, hypertension, atherosclerosis, endothelial dysfunction, osteoporosis, chronic systemic inflammation, non alcoholic fatty liver disease (NAFLD), retinopathy, neuropathy, nephropathy, polycystic ovarian syndrome, and/or metabolic syndrome;
- improving and/or maintaining glycemic control and/or for reducing of fasting plasma glucose, of postprandial plasma glucose, of postabsorptive plasma glucose and/or of glycosylated hemoglobin HbA1c;
- preventing, slowing, delaying or reversing progression from pre-diabetes, impaired glucose tolerance (IGT), impaired fasting blood glucose (IFG), insulin resistance and/or from metabolic syndrome to type 2 diabetes mellitus;
- preventing, reducing the risk of, slowing the progression of, delaying or treating of complications of diabetes mellitus such as micro- and macrovascular diseases, such as nephropathy, micro- or macroalbuminuria, proteinuria, retinopathy, cataracts, neuropathy, learning or memory impairment, neurodegenerative or cognitive disorders, cardio- or cerebrovascular diseases, tissue ischaemia, diabetic foot or ulcus, atherosclerosis, hypertension, endothelial dysfunction, myocardial infarction, acute coronary syndrome, unstable angina pectoris, stable angina pectoris, peripheral arterial occlusive disease, cardiomyopathy (including e.g. uremic cardiomyopathy), heart failure, heart rhythm disorders, vascular restenosis, and/or stroke;
- reducing body weight and/or body fat or preventing an increase in body weight and/or body fat or facilitating a reduction in body weight and/or body fat;
- preventing, slowing, delaying or treating the degeneration of pancreatic beta cells and/or the decline of the functionality of pancreatic beta cells and/or for improving, preserving and/or restoring the functionality of pancreatic beta cells and/or stimulating and/or restoring or protecting the functionality of pancreatic insulin secretion;
- preventing, slowing, delaying or treating non alcoholic fatty liver disease (NAFLD) including hepatic steatosis, non-alcoholic steatohepatitis (NASH) and/or liver fibrosis (such as e.g. preventing, slowing the progression, delaying, attenuating, treating or reversing hepatic steatosis, (hepatic) inflammation and/or an abnormal accumulation of liver fat);
- preventing, slowing the progression of, delaying or treating type 2 diabetes with failure to conventional antidiabetic mono- or combination therapy;
- achieving a reduction in the dose of conventional antidiabetic medication required for adequate therapeutic effect;
- reducing the risk for adverse effects associated with conventional antidiabetic medication (e.g. hypoglycemia and/or weight gain); and/or
- maintaining and/or improving the insulin sensitivity and/or for treating or preventing hyperinsulinemia and/or insulin resistance;

in a patient in need thereof (such as e.g. a patient as described herein, especially a type 2 diabetes patient),
particularly
in a patient with or at risk of oxidative stress, vascular stress and/or endothelial dysfunction, or diseases or conditions related or associated therewith, or
in a patient with or at risk of cardiovascular and/or renal disease (such as e.g. myocardial infarction, stroke or peripheral arterial occlusive disease and/or diabetic nephropathy, micro- or macroalbuminuria, or acute or chronic renal impairment), or
in a patient with one or more cardiovascular risk factors selected from A), B), C) and D):
A) previous or existing vascular disease (such as e.g. myocardial infarction (e.g. silent or non-silent), coronary artery disease, percutaneous coronary intervention, coronary artery by-pass grafting, ischemic or hemorrhagic stroke, congestive heart failure (e.g. NYHA class I or II, e.g. left ventricular function <40%), or peripheral occlusive arterial disease),
B) vascular related end-organ damage (such as e.g. nephropathy, retinopathy, neuropathy, impaired renal function, chronic kidney disease, and/or micro- or macroalbuminuria),
C) advanced age (such as e.g. age >/=60-70 years), and
D) one or more cardiovascular risk factors selected from advanced type 2 diabetes mellitus (such as e.g. >10 years duration), hypertension (such as e.g. >130/80 mm Hg, or systolic blood pressure >140 mmHg or on at least one blood pressure lowering treatment), current daily cigarette smoking, dyslipidemia (such as e.g. atherogenic dyslipidemia, postprandial lipemia, or high level of LDL cholersterol (e.g. LDL cholesterol >/=130-135 mg/dL), low level of HDL cholesterol (e.g. <35-40 mg/dL in men or <45-50 mg/dL in women) and/or high level of triglycerides (e.g. >200-400 mg/dL) in the blood, or on at least one treatment for lipid abnormality), obesity (such as e.g. abdominal and/or visceral obesity, or body mass index >/=45 kg/m2), age >/=40 and </=80 years, metabolic syndrome, hyperinsulinemia or insulin resistance, and hyperuricemia, erectile dysfunction, polycystic ovary syndrome, sleep apnea, or family history of vascular disease or cardiomyopathy in first-degree relative;

said method comprising administering a therapeutically effective amount of a certain DPP-4 inhibitor, optionally in combination with one or more other therapeutic substances as described herein.

Other aspects of the present invention become apparent to the skilled person from the foregoing and following remarks (including the examples and claims).

The aspects of the present invention, in particular the pharmaceutical compounds, compositions, combinations, methods and uses, refer to DPP-4 inhibitors as defined hereinbefore and hereinafter.

A DPP-4 inhibitor within the meaning of the present invention includes, without being limited to, any of those DPP-4 inhibitors mentioned hereinabove and hereinbelow, preferably orally active DPP-4 inhibitors.

An embodiment of this invention refers to a DPP-4 inhibitor for use in the treatment and/or prevention of metabolic diseases (particularly type 2 diabetes mellitus) in type 2 diabetes patients, wherein said patients further suffering from renal disease, renal dysfunction or renal impairment, particularly characterized in that said DPP-4 inhibitor is administered to said patients in the same dose levels as to patients with normal renal function, thus e.g. said DPP-4 inhibitor does not require downward dosing adjustment for impaired renal function.

For example, a DPP-4 inhibitor according to this invention (especially one which may be suited for patients with impaired renal function) may be such an oral DPP-4 inhibitor, which and whose active metabolites have preferably a relatively wide (e.g. about >100 fold) therapeutic window and/or, especially, that are primarily eliminated via hepatic metabolism or biliary excretion (preferably without adding additional burden to the kidney).

In more detailed example, a DPP-4 inhibitor according to this invention (especially one which may be suited for patients with impaired renal function) may be such an orally administered DPP-4 inhibitor, which has a relatively wide (e.g. >100 fold) therapeutic window (preferably a safety profile comparable to placebo) and/or which fulfils one or more of the following pharmacokinetic properties (preferably at its therapeutic oral dose levels):

The DPP-4 inhibitor is substantially or mainly excreted via the liver (e.g. >80% or even >90% of the administered oral dose), and/or for which renal excretion represents no substantial or only a minor elimination pathway (e.g. <10%, preferably <7%, of the administered oral dose measured, for example, by following elimination of a radiolabelled carbon ($^{14}$C) substance oral dose);

The DPP-4 inhibitor is excreted mainly unchanged as parent drug (e.g. with a mean of >70%, or >80%, or, preferably, 90% of excreted radioactivity in urine and feces after oral dosing of radiolabelled carbon ($^{14}$C) substance), and/or which is eliminated to a non-substantial or only to a minor extent via metabolism (e.g. <30%, or <20%, or, preferably, 10%);

The (main) metabolite(s) of the DPP-4 inhibitor is/are pharmacologically inactive. Such as e.g. the main metabolite does not bind to the target enzyme DPP-4 and, optionally, it is rapidly eliminated compared to the parent compound (e.g. with a terminal half-life of the metabolite of ≤20 h, or, preferably, ≤about 16 h, such as e.g. 15.9 h).

In one embodiment, the (main) metabolite in plasma (which may be pharmacologically inactive) of a DPP-4 inhibitor having a 3-amino-piperidin-1-yl substituent is such a derivative where the amino group of the 3-amino-piperidin-1-yl moiety is replaced by a hydroxyl group to form the 3-hydroxy-piperidin-1-yl moiety (e.g. the 3-(S)-hydroxy-piperidin-1-yl moiety, which is formed by inversion of the configuration of the chiral center).

Further properties of a DPP-4 inhibitor according to this invention may be one or more of the following: Rapid attainment of steady state (e.g. reaching steady state plasma levels (>90% of the steady state plasma concentration) between second and fifth day of treatment with therapeutic oral dose levels), little accumulation (e.g. with a mean accumulation ratio $R_{A,AUC}$≤1.4 with therapeutic oral dose levels), and/or preserving a long-lasting effect on DPP-4 inhibition, preferably when used once-daily (e.g. with almost complete (>90%) DPP-4 inhibition at therapeutic oral dose levels, >80% inhibition over a 24 h interval after once-daily intake of therapeutic oral drug dose), significant decrease in 2 h postprandial blood glucose excursions by 80% (already on first day of therapy) at therapeutic dose levels, and cumulative amount of unchanged parent compound excreted in urine on first day being below 1% of the administered dose and increasing to not more than about 3-6% in steady state.

Thus, for example, a DPP-4 inhibitor according to this invention may be characterized in that said DPP-4 inhibitor has a primarily non-renal route of excretion, i.e. said DPP-4 inhibitor is excreted to a non-substantial or only to a minor extent (e.g. <10%, preferably <7%, e.g. about 5%, of administered oral dose, preferably of oral therapeutic dose) via the kidney (measured, for example, by following elimination of a radiolabelled carbon ($^{14}$C) substance oral dose).

Further, a DPP-4 inhibitor according to this invention may be characterized in that said DPP-4 inhibitor is excreted substantially or mainly via the liver or feces (measured, for example, by following elimination of a radiolabelled carbon ($^{14}$C) substance oral dose).

Further, a DPP-4 inhibitor according to this invention may be characterized in that said DPP-4 inhibitor is excreted mainly unchanged as parent drug (e.g. with a mean of >70%, or >80%, or, preferably, 90% of excreted radioactivity in urine and feces after oral dosing of radiolabelled carbon ($^{14}$C) substance), said DPP-4 inhibitor is eliminated to a non-substantial or only to a minor extent via metabolism, and/or the main metabolite of said DPP-4 inhibitor is pharmacologically inactive or has a relatively wide therapeutic window.

Further, a DPP-4 inhibitor according to this invention may be characterized in that said DPP-4 inhibitor does not significantly impair glomerular and/or tubular function of a type 2 diabetes patient with chronic renal insufficiency (e.g. mild, moderate or severe renal impairment or end stage renal disease), and/or said DPP-4 inhibitor trough levels in the blood plasma of type 2 diabetes patients with mild or moderate renal impairment are comparable to the levels in patients with normal renal function, and/or said DPP-4 inhibitor does not require to be dose-adjusted in a type 2 diabetes patient with impaired renal function (e.g. mild, moderate or severe renal impairment or end stage renal disease, preferably regardless of the stage of renal impairment).

Further, a DPP-4 inhibitor according to this invention may be characterized in that said DPP-4 inhibitor provides its minimally effective dose at that dose that results in >50% inhibition of DPP-4 activity at trough (24 h after last dose) in >80% of patients, and/or said DPP-4 inhibitor provides its fully therapeutic dose at that dose that results in >80% inhibition of DPP-4 activity at trough (24 h after last dose) in >80% of patients.

Further, a DPP-4 inhibitor according to this invention may be characterized in that being suitable for use in type 2 diabetes patients who are with diagnosed renal impairment and/or who are at risk of developing renal complications, e.g. patients with or at risk of diabetic nephropathy (including chronic and progressive renal insufficiency, albuminuria, proteinuria, fluid retention in the body (edema) and/or hypertension).

In a first embodiment (embodiment A), a DPP-4 inhibitor in the context of the present invention is any DPP-4 inhibitor of formula (I)

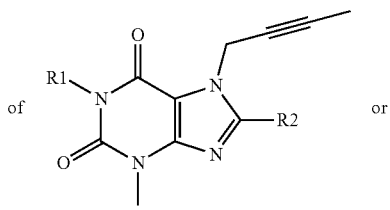

(I)

of or formula (II)

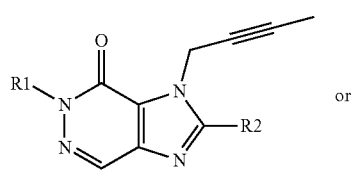

(II)

or formula (III)

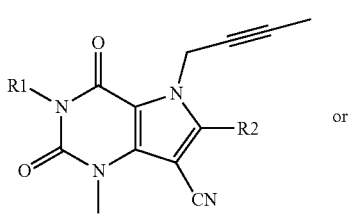

(III)

or formula (IV)

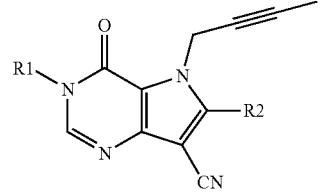

(IV)

wherein R1 denotes ([1,5]naphthyridin-2-yl)methyl, (quinazolin-2-yl)methyl, (quinoxalin-6-yl)methyl, (4-methyl-quinazolin-2-yl)methyl, 2-cyano-benzyl, (3-cyano-quinolin-2-yl)methyl, (3-cyano-pyridin-2-yl)methyl, (4-methyl-pyrimidin-2-yl)methyl, or (4,6-dimethyl-pyrimidin-2-yl)methyl and R2 denotes 3-(R)-amino-piperidin-1-yl, (2-amino-2-methyl-propyl)-methylamino or (2-(S)-aminopropyl)-methylamino, or its pharmaceutically acceptable salt.

Regarding the first embodiment (embodiment A), preferred DPP-4 inhibitors are any or all of the following compounds and their pharmaceutically acceptable salts:

1-[(4-methyl-quinazolin-2-yl)methyl]-3-methyl-7-(2-butyn-1-yl)-8-(3-(R)-amino-piperidin-1-yl)-xanthine (compare WO 2004/018468, example 2(142))

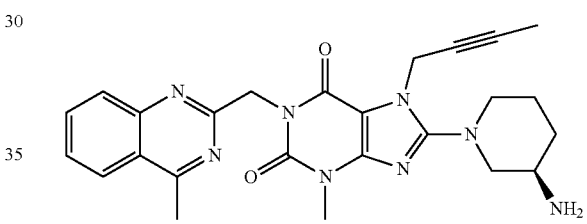

1-[([1,5]naphthyridin-2-yl)methyl]-3-methyl-7-(2-butyn-1-yl)-8-((R)-3-amino-piperidin-1-yl)-xanthine (compare WO 2004/018468, example 2(252))

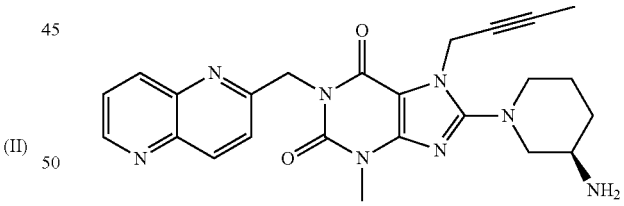

1-[(Quinazolin-2-yl)methyl]-3-methyl-7-(2-butyn-1-yl)-8-((R)-3-amino-piperidin-1-yl)-xanthine (compare WO 2004/018468, example 2(80))

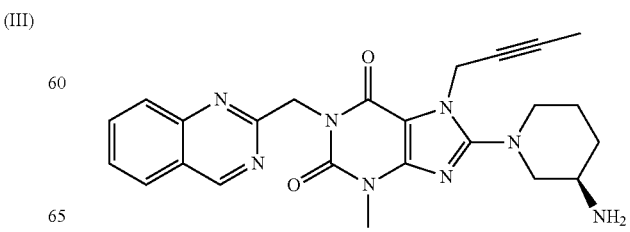

2-((R)-3-Amino-piperidin-1-yl)-3-(but-2-yinyl)-5-(4-methyl-quinazolin-2-ylmethyl)-3,5-dihydro-imidazo[4,5-d]pyridazin-4-one (compare WO 2004/050658, example 136)

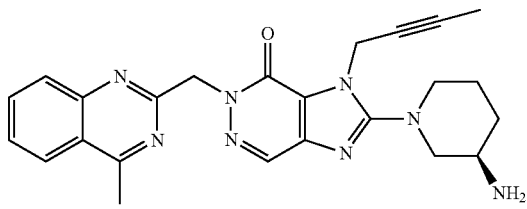 [SMILES: CC#CCn1c(N2CCC[C@@H](N)C2)nc2cnn(Cc3nc(C)c4ccccc4n3)c(=O)c21]

1-[(4-Methyl-quinazolin-2-ylmethyl]-3-methyl-7-(2-butyln-1-yl)-8-[(2-amino-2-methyl-propyl)-methylamino]-xanthine (compare WO 2006/029769, example 2(1))

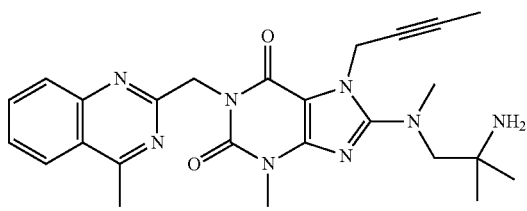 [SMILES: CC#CCn1c(N(C)CC(C)(C)N)nc2c1c(=O)n(Cc1nc(C)c3ccccc3n1)c(=O)n2C]

1-[(3-Cyano-quinolin-2-ylmethyl]-3-methyl-7-(2-butyn-1-yl)-8-((R)-3-amino-piperidin-1-yl)-xanthine (compare WO 2005/085246, example 1(30))

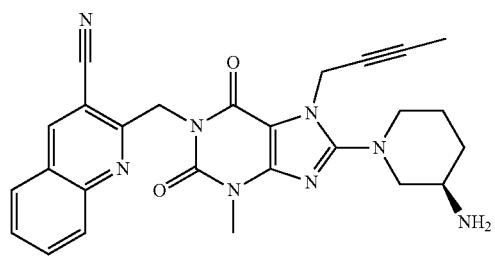 [SMILES: CC#CCn1c(N2CCC[C@@H](N)C2)nc2c1c(=O)n(Cc1nc3ccccc3cc1C#N)c(=O)n2C]

1-(2-Cyano-benzyl)-3-methyl-7-(2-butyn-1-yl)-8-((R)-3-amino-piperidin-1-yl)-xanthine (compare WO 2005/085246, example 1(39))

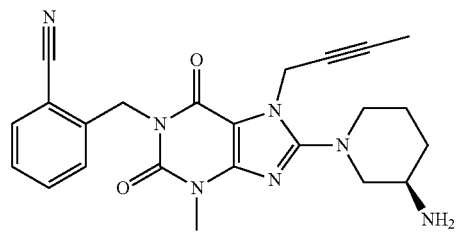 [SMILES: CC#CCn1c(N2CCC[C@@H](N)C2)nc2c1c(=O)n(Cc1ccccc1C#N)c(=O)n2C]

1-[(4-Methyl-quinazolin-2-ylmethyl]-3-methyl-7-(2-butyn-1-yl)-8-[(S)-(2-amino-propyl)-methylamino]-xanthine (compare WO 2006/029769, example 2(4))

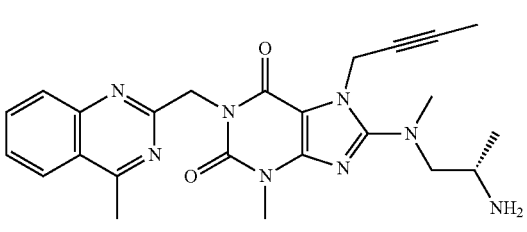 [SMILES: CC#CCn1c(N(C)C[C@H](C)N)nc2c1c(=O)n(Cc1nc(C)c3ccccc3n1)c(=O)n2C]

1-[(3-Cyano-pyridin-2-yl)methyl]-3-methyl-7-(2-butyn-1-yl)-8-((R)-3-amino-piperidin-1-yl)-xanthine (compare WO 2005/085246, example 1(52))

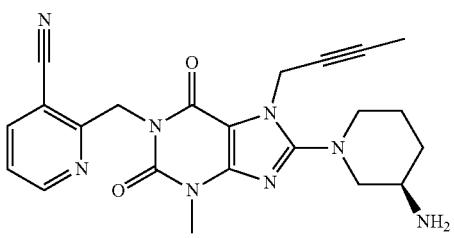 [SMILES: CC#CCn1c(N2CCC[C@@H](N)C2)nc2c1c(=O)n(Cc1ncccc1C#N)c(=O)n2C]

1-[(4-Methyl-pyrimidin-2-yl)methyl]-3-methyl-7-(2-butyn-1-yl)-8-((R)-3-amino-piperidin-1-yl)-xanthine (compare WO 2005/085246, example 1(81))

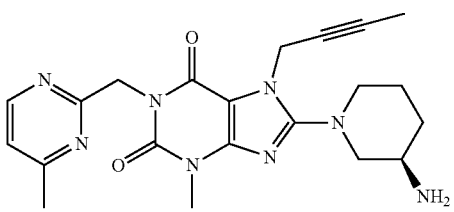 [SMILES: CC#CCn1c(N2CCC[C@@H](N)C2)nc2c1c(=O)n(Cc1nccc(C)n1)c(=O)n2C]

1-[(4,6-Dimethyl-pyrimidin-2-yl)methyl]-3-methyl-7-(2-butyn-1-yl)-8-((R)-3-amino-piperidin-1-yl)-xanthine (compare WO 2005/085246, example 1(82))

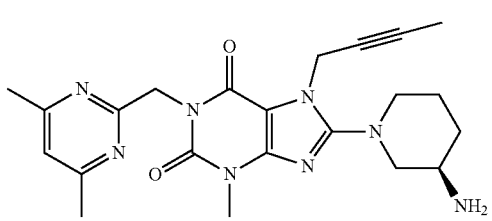 [SMILES: CC#CCn1c(N2CCC[C@@H](N)C2)nc2c1c(=O)n(Cc1nc(C)cc(C)n1)c(=O)n2C]

1-[(Quinoxalin-6-yl)methyl]-3-methyl-7-(2-butyn-1-yl)-8-((R)-3-amino-piperidin-1-yl)-xanthine (compare WO 2005/085246, example 1(83))

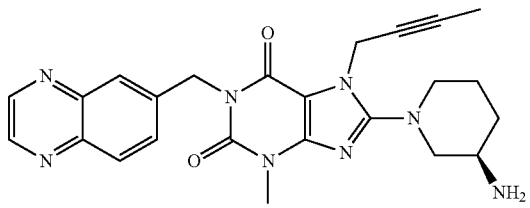 [SMILES: CC#CCn1c(N2CCC[C@@H](N)C2)nc2c1c(=O)n(Cc1ccc3nccnc3c1)c(=O)n2C]

These DPP-4 inhibitors are distinguished from structurally comparable DPP-4 inhibitors, as they combine exceptional potency and a long-lasting effect with favourable pharmacological properties, receptor selectivity and a favourable side-effect profile or bring about unexpected therapeutic advantages or improvements when combined with other pharmaceutical active substances. Their preparation is disclosed in the publications mentioned.

A more preferred DPP-4 inhibitor among the abovementioned DPP-4 inhibitors of embodiment A of this invention is 1-[(4-methyl-quinazolin-2-ylmethyl]-3-methyl-7-(2-butyn-1-yl)-8-(3-(R)-amino-piperidin-1-yl)-xanthine, particularly the free base thereof (which is also known as linagliptin or BI 1356).

A particularly preferred DPP-4 inhibitor within the present invention is linagliptin. The term "linagliptin" as employed herein refers to linagliptin or a pharmaceutically acceptable salt thereof, including hydrates and solvates thereof, and crystalline forms thereof, preferably linagliptin refers to 1-[(4-methyl-quinazolin-2-ylmethyl]-3-methyl-7-(2-butyn-1-yl)-8-(3-(R)-amino-piperidin-1-yl)-xanthine. Crystalline forms are described in WO 2007/128721. Methods for the manufacture of linagliptin are described in the patent applications WO 2004/018468 and WO 2006/048427 for example. Linagliptin is distinguished from structurally comparable DPP-4 inhibitors, as it combines exceptional potency and a long-lasting effect with favourable pharmacological properties, receptor selectivity and a favourable side-effect profile or bring about unexpected therapeutic advantages or improvements in mono- or dual or triple combination therapy.

For avoidance of any doubt, the disclosure of each of the foregoing and following documents cited above in connection with the specified DPP-4 inhibitors is specifically incorporated herein by reference in its entirety.

Within this invention it is to be understood that the combinations, compositions or combined uses according to this invention may envisage the simultaneous, sequential or separate administration of the active components or ingredients.

In this context, "combination" or "combined" within the meaning of this invention may include, without being limited, fixed and non-fixed (e.g. free) forms (including kits) and uses, such as e.g. the simultaneous, sequential or separate use of the components or ingredients.

The combined administration of this invention may take place by administering the active components or ingredients together, such as e.g. by administering them simultaneously in one single or in two separate formulations or dosage forms. Alternatively, the administration may take place by administering the active components or ingredients sequentially, such as e.g. successively in two separate formulations or dosage forms.

For the combination therapy of this invention the active components or ingredients may be administered separately (which implies that they are formulated separately) or formulated altogether (which implies that they are formulated in the same preparation or in the same dosage form). Hence, the administration of one element of the combination of the present invention may be prior to, concurrent to, or subsequent to the administration of the other element of the combination.

Unless otherwise noted, combination therapy may refer to first line, second line or third line therapy, or initial or add-on combination therapy or replacement therapy.

With respect to embodiment A, the methods of synthesis for the DPP-4 inhibitors according to embodiment A of this invention are known to the skilled person. Advantageously, the DPP-4 inhibitors according to embodiment A of this invention can be prepared using synthetic methods as described in the literature. Thus, for example, purine derivatives of formula (I) can be obtained as described in WO 2002/068420, WO 2004/018468, WO 2005/085246, WO 2006/029769 or WO 2006/048427, the disclosures of which are incorporated herein. Purine derivatives of formula (II) can be obtained as described, for example, in WO 2004/050658 or WO 2005/110999, the disclosures of which are incorporated herein. Purine derivatives of formula (III) and (IV) can be obtained as described, for example, in WO 2006/068163, WO 2007/071738 or WO 2008/017670, the disclosures of which are incorporated herein. The preparation of those DPP-4 inhibitors, which are specifically mentioned hereinabove, is disclosed in the publications mentioned in connection therewith. Polymorphous crystal modifications and formulations of particular DPP-4 inhibitors are disclosed in WO 2007/128721 and WO 2007/128724, respectively, the disclosures of which are incorporated herein in their entireties. Formulations of particular DPP-4 inhibitors with metformin or other combination partners are described in WO 2009/121945, the disclosure of which is incorporated herein in its entirety.

Typical dosage strengths of the dual fixed combination (tablet) of linagliptin/metformin IR (immediate release) are 2.5/500 mg, 2.5/850 mg and 2.5/1000 mg, which may be administered 1-3 times a day, particularly twice a day.

Typical dosage strengths of the dual fixed combination (tablet) of linagliptin/metformin XR (extended release) are 5/500 mg, 5/1000 mg and 5/1500 mg (each one tablet), or 2.5/500 mg, 2.5/750 mg and 2.5/1000 mg (each two tablets), which may be administered 1-2 times a day, particularly once a day, preferably to be taken in the evening with meal.

The present invention further provides a DPP-4 inhibitor as defined herein for use in (add-on or initial) combination therapy with metformin (e.g. in a total daily amount from 500 to 2000 mg metformin hydrochloride, such as e.g. 500 mg, 850 mg or 1000 mg once or twice daily).

For pharmaceutical application in warm-blooded vertebrates, particularly humans, the compounds of this invention are usually used in dosages from 0.001 to 100 mg/kg body weight, preferably at 0.01-15 mg/kg or 0.1-15 mg/kg, in each case 1 to 4 times a day. For this purpose, the compounds, optionally combined with other active substances, may be incorporated together with one or more inert conventional carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethylene glycol, propylene glycol, cetylstearyl alcohol, carboxymethylcellulose or fatty substances such as hard fat or suitable mixtures thereof into conventional galenic preparations such as plain or coated tablets, capsules, powders, suspensions or suppositories.

The pharmaceutical compositions according to this invention comprising the DPP-4 inhibitors as defined herein are thus prepared by the skilled person using pharmaceutically acceptable formulation excipients as described in the art and appropriate for the desired route of administration. Examples of such excipients include, without being restricted to diluents, binders, carriers, fillers, lubricants, flow promoters, crystallisation retardants, disintegrants, solubilizers, colorants, pH regulators, surfactants and emulsifiers.

Oral preparations or dosage forms of the DPP-4 inhibitor of this invention may be prepared according to known techniques.

Examples of suitable diluents for compounds according to embodiment A include cellulose powder, calcium hydrogen phosphate, erythritol, low substituted hydroxypropyl cellulose, mannitol, pregelatinized starch or xylitol.

Examples of suitable lubricants for compounds according to embodiment A include talc, polyethyleneglycol, calcium behenate, calcium stearate, hydrogenated castor oil or magnesium stearate.

Examples of suitable binders for compounds according to embodiment A include copovidone (copolymerisates of vinylpyrrolidon with other vinylderivates), hydroxypropyl methylcellulose (HPMC), hydroxypropylcellulose (HPC), polyvinylpyrrolidon (povidone), pregelatinized starch, or low-substituted hydroxypropylcellulose (L-HPC).

Examples of suitable disintegrants for compounds according to embodiment A include corn starch or crospovidone.

Suitable methods of preparing pharmaceutical formulations of the DPP-4 inhibitors according to embodiment A of the invention are
   direct tabletting of the active substance in powder mixtures with suitable tabletting excipients;
   granulation with suitable excipients and subsequent mixing with suitable excipients and subsequent tabletting as well as film coating; or
   packing of powder mixtures or granules into capsules.
Suitable granulation methods are
   wet granulation in the intensive mixer followed by fluidised bed drying;
   one-pot granulation;
   fluidised bed granulation; or
   dry granulation (e.g. by roller compaction) with suitable excipients and subsequent tabletting or packing into capsules.

An exemplary composition (e.g. tablet core) of a DPP-4 inhibitor according to embodiment A of the invention comprises the first diluent mannitol, pregelatinized starch as a second diluent with additional binder properties, the binder copovidone, the disintegrant corn starch, and magnesium stearate as lubricant; wherein copovidone and/or corn starch may be optional.

A tablet of a DPP-4 inhibitor according to embodiment A of the invention may be film coated, preferably the film coat comprises hydroxypropylmethylcellulose (HPMC), polyethylene glycol (PEG), talc, titanium dioxide and iron oxide (e.g. red and/or yellow).

The pharmaceutical compositions (or formulations) may be packaged in a variety of ways. Generally, an article for distribution includes one or more containers that contain the one or more pharmaceutical compositions in an appropriate form. Tablets are typically packed in an appropriate primary package for easy handling, distribution and storage and for assurance of proper stability of the composition at prolonged contact with the environment during storage. Primary containers for tablets may be bottles or blister packs.

A suitable bottle, e.g. for a pharmaceutical composition or combination (tablet) comprising a DPP-4 inhibitor according to embodiment A of the invention, may be made from glass or polymer (preferably polypropylene (PP) or high density polyethylene (HD-PE)) and sealed with a screw cap. The screw cap may be provided with a child resistant safety closure (e.g. press-and-twist closure) for preventing or hampering access to the contents by children. If required (e.g. in regions with high humidity), by the additional use of a desiccant (such as e.g. bentonite clay, molecular sieves, or, preferably, silica gel) the shelf life of the packaged composition can be prolonged.

A suitable blister pack, e.g. for a pharmaceutical composition or combination (tablet) comprising a DPP-4 inhibitor according to embodiment A of the invention, comprises or is formed of a top foil (which is breachable by the tablets) and a bottom part (which contains pockets for the tablets). The top foil may contain a metalic foil, particularly an aluminium or aluminium alloy foil (e.g. having a thickness of 20 µm to 45 µm, preferably 20 µm to 25 µm) that is coated with a heat-sealing polymer layer on its inner side (sealing side). The bottom part may contain a multi-layer polymer foil (such as e.g. poly(vinyl chloride) (PVC) coated with poly(vinylidene chloride) (PVDC); or a PVC foil laminated with poly(chlorotrifluoroethylene) (PCTFE)) or a multi-layer polymer-metal-polymer foil (such as e.g. a cold-formable laminated PVC/aluminium/polyamide composition).

To ensure a long storage period especially under hot and wet climate conditions an additional overwrap or pouch made of a multi-layer polymer-metal-polymer foil (e.g. a laminated polyethylen/aluminium/polyester composition) may be used for the blister packs. Supplementary desiccant (such as e.g. bentonite clay, molecular sieves, or, preferably, silica gel) in this pouch package may prolong the shelf life even more under such harsh conditions.

The article may further comprise a label or package insert, which refer to instructions customarily included in commercial packages of therapeutic products, that may contain information about the indications, usage, dosage, administration, contraindications and/or warnings concerning the use of such therapeutic products. In one embodiment, the label or package inserts indicates that the composition can be used for any of the purposes described herein.

With respect to the first embodiment (embodiment A), the dosage typically required of the DPP-4 inhibitors mentioned herein in embodiment A when administered intravenously is 0.1 mg to 10 mg, preferably 0.25 mg to 5 mg, and when administered orally is 0.5 mg to 100 mg, preferably 2.5 mg to 50 mg or 0.5 mg to 10 mg, more preferably 2.5 mg to 10 mg or 1 mg to 5 mg, in each case 1 to 4 times a day. Thus, e.g. the dosage of 1-[(4-methyl-quinazolin-2-yl)methyl]-3-methyl-7-(2-butyn-1-yl)-8-(3-(R)-amino-piperidin-1-yl)-xanthine when administered orally is 0.5 mg to 10 mg per patient per day, preferably 2.5 mg to 10 mg or 1 mg to 5 mg per patient per day.

A dosage form prepared with a pharmaceutical composition comprising a DPP-4 inhibitor mentioned herein in embodiment A contain the active ingredient in a dosage range of 0.1-100 mg. Thus, e.g. particular oral dosage strengths of 1-[(4-methyl-quinazolin-2-yl)methyl]-3-methyl-7-(2-butyn-1-yl)-8-(3-(R)-amino-piperidin-1-yl)-xanthine are 0.5 mg, 1 mg, 2.5 mg, 5 mg and 10 mg.

A special embodiment of the DPP-4 inhibitors of this invention refers to those orally administered DPP-4 inhibitors which are therapeutically efficacious at low dose levels, e.g. at oral dose levels <100 mg or <70 mg per patient per day, preferably <50 mg, more preferably <30 mg or <20 mg, even more preferably from 1 mg to 10 mg, particularly from 1 mg to 5 mg (more particularly 5 mg), per patient per day (if required, divided into 1 to 4 single doses, particularly 1 or 2 single doses, which may be of the same size, preferentially, administered orally once- or twice daily (more preferentially once-daily), advantageously, administered at any time of day, with or without food. Thus, for example, the daily oral amount 5 mg BI 1356 can be given in an once daily dosing regimen (i.e. 5 mg BI 1356 once daily) or in a twice daily dosing regimen (i.e. 2.5 mg BI 1356 twice daily), at any time of day, with or without food.

The dosage of the active ingredients in the combinations and compositions in accordance with the present invention may be varied, although the amount of the active ingredients shall be such that a suitable dosage form is obtained. Hence, the selected dosage and the selected dosage form shall depend on the desired therapeutic effect, the route of administration and the duration of the treatment. Suitable dosage ranges for the combination are from the maximal tolerated dose for the single agent to lower doses, e.g. to one tenth of the maximal tolerated dose.

A particularly preferred DPP-4 inhibitor to be emphasized within the meaning of this invention is 1-[(4-methyl-quinazolin-2-yl)methyl]-3-methyl-7-(2-butyn-1-yl)-8-(3-(R)-amino-piperidin-1-yl)-xanthine (also known as BI 1356 or linagliptin). BI 1356 exhibits high potency, 24 h duration of action, and a wide therapeutic window. In patients with type 2 diabetes receiving multiple oral doses of 1, 2.5, 5 or 10 mg of BI 1356 once daily for 12 days, BI 1356 shows favourable pharmacodynamic and pharmacokinetic profile (see e.g. Table 1 below) with rapid attainment of steady state (e.g. reaching steady state plasma levels (>90% of the pre-dose plasma concentration on Day 13) between second and fifth day of treatment in all dose groups), little accumulation (e.g. with a mean accumulation ratio $R_{A,AUC} \leq 1.4$ with doses above 1 mg) and preserving a long-lasting effect on DPP-4 inhibition (e.g. with almost complete (>90%) DPP-4 inhibition at the 5 mg and 10 mg dose levels, i.e. 92.3 and 97.3% inhibition at steady state, respectively, and >80% inhibition over a 24 h interval after drug intake), as well as significant decrease in 2 h postprandial blood glucose excursions by ≥80 (already on Day 1) in doses ≥2.5 mg, and with the cumulative amount of unchanged parent compound excreted in urine on Day 1 being below 1% of the administered dose and increasing to not more than about 3-6% on Day 12 (renal clearance $CL_{R,ss}$ is from about 14 to about 70 mL/min for the administered oral doses, e.g. for the 5 mg dose renal clearance is about 70 ml/min). In people with type 2 diabetes BI 1356 shows a placebo-like safety and tolerability. With low doses of about ≥5 mg, BI 1356 acts as a true once-daily oral drug with a full 24 h duration of DPP-4 inhibition. At therapeutic oral dose levels, BI 1356 is mainly excreted via the liver and only to a minor extent (about <7% of the administered oral dose) via the kidney. BI 1356 is primarily excreted unchanged via the bile. The fraction of BI 1356 eliminated via the kidneys increases only very slightly over time and with increasing dose, so that there will likely be no need to modify the dose of BI 1356 based on the patients' renal function. The non-renal elimination of BI 1356 in combination with its low accumulation potential and broad safety margin may be of significant benefit in a patient population that has a high prevalence of renal insufficiency and diabetic nephropathy.

TABLE 1

Geometric mean (gMean) and geometric coefficient of variation (gCV) of pharmacokinetic parameters of BI 1356 at steady state (Day 12)

| Parameter | 1 mg gMean (gCV) | 2.5 mg gMean (gCV) | 5 mg gMean (gCV) | 10 mg gMean (gCV) |
|---|---|---|---|---|
| $AUC_{0-24}$ [nmol·h/L] | 40.2 (39.7) | 85.3 (22.7) | 118 (16.0) | 161 (15.7) |
| $AUC_{T,ss}$ [nmol·h/L] | 81.7 (28.3) | 117 (16.3) | 158 (10.1) | 190 (17.4) |
| $C_{max}$ [nmol/L] | 3.13 (43.2) | 5.25 (24.5) | 8.32 (42.4) | 9.69 (29.8) |
| $C_{max,ss}$ [nmol/L] | 4.53 (29.0) | 6.58 (23.0) | 11.1 (21.7) | 13.6 (29.6) |
| $t_{max}$* [h] | 1.50 [1.00 – 3.00] | 2.00 [1.00 – 3.00] | 1.75 [0.92 – 6.02] | 2.00 [1.50 – 6.00] |
| $t_{max,ss}$* [h] | 1.48 [1.00 – 3.00] | 1.42 [1.00 – 3.00] | 1.53 [1.00 – 3.00] | 1.34 [0.50 – 3.00] |
| $T_{1/2,ss}$ [h] | 121 (21.3) | 113 (10.2) | 131 (17.4) | 130 (11.7) |
| Accumulation | 23.9 (44.0) | 12.5 (18.2) | 11.4 (37.4) | 8.59 (81.2) |
| $t_{1/2}$ [h] | 1.44 (25.6) | 1.25 (10.6) | 1.33 (30.0) | 1.40 (47.7) |
| $R_{A,Cmax}$ | 2.03 (30.7) | 1.37 (8.2) | 1.33 (15.0) | 1.18 (23.4) |
| $R_{A,AUC}$ | | | | |
| $fe_{0-24}$ [%] | NC | 0.139 (51.2) | 0.453 (125) | 0.919 (115) |
| $fe_{T,ss}$ [%] | 3.34 (38.3) | 3.06 (45.1) | 6.27 (42.2) | 3.22 (34.2) |
| $CL_{R,ss}$ [mL/min] | 14.0 (24.2) | 23.1 (39.3) | 70 (35.0) | 59.5 (22.5) |

*median and range [min-max]
NC not calculated as most values below lower limit of quantification As different metabolic functional disorders often occur simultaneously, it is quite often indicated to combine a number of different active principles with one another. Thus, depending on the functional disorders diagnosed, improved treatment outcomes may be obtained if a DPP-4 inhibitor is combined with active substances customary for the respective disorders, such as e.g. one or more active substances selected from among the other antidiabetic substances, especially active substances that lower the blood sugar level or the lipid level in the blood, raise the HDL level in the blood, lower blood pressure or are indicated in the treatment of atherosclerosis or obesity.

The DPP-4 inhibitors mentioned above—besides their use in mono-therapy—may also be used in conjunction with other active substances, by means of which improved treatment results can be obtained. Such a combined treatment may be given as a free combination of the substances or in the form of a fixed combination, for example in a tablet or capsule. Pharmaceutical formulations of the combination partner needed for this may either be obtained commercially as pharmaceutical compositions or may be formulated by the skilled man using conventional methods. The active substances which may be obtained commercially as pharmaceutical compositions are described in numerous places in the prior art, for example in the list of drugs that appears annually, the "Rote Liste®" of the federal association of the pharmaceutical industry, or in the annually updated compilation of manufacturers' information on prescription drugs known as the "Physicians' Desk Reference".

Examples of antidiabetic combination partners are metformin; sulphonylureas such as glibenclamide, tolbutamide, glimepiride, glipizide, gliquidon, glibornuride and gliclazide; nateglinide; repaglinide; mitiglinide; thiazolidinediones such as rosiglitazone and pioglitazone; PPAR gamma modulators such as metaglidases; PPAR-gamma agonists such as e.g. rivoglitazone, mitoglitazone, INT-131 and balaglitazone; PPAR-gamma antagonists; PPAR-gamma/alpha modulators such as tesaglitazar, muraglitazar, aleglitazar, indeglitazar and KRP297; PPAR-gamma/alpha/delta modulators such as e.g. lobeglitazone; AMPK-activators such as AICAR; acetyl-CoA carboxylase (ACC1 and ACC2) inhibitors; diacylglycerol-acetyltransferase (DGAT) inhibitors; pancreatic beta cell GCRP agonists such as SMT3-receptor-agonists and GPR119, such as the GPR119 agonists 5-ethyl-2-{4-[4-(4-tetrazol-1-yl-phenoxymethyl)-thiazol-2-yl]-piperidin-1-yl}-pyrimidine or 5-[1-(3-isopropyl-[1,2,4]oxadiazol-5-yl)-piperidin-4-ylmethoxy]-2-(4-methanesulfonyl-phenyl)-pyridine; 11β-HSD-inhibitors; FGF19 agonists or analogues; alpha-glucosidase blockers such as acarbose, voglibose and miglitol; alpha2-antagonists; insulin and insulin analogues such as human insulin, insulin lispro, insulin glusilin, r-DNA-insulinaspart, NPH insulin, insulin detemir, insulin degludec, insulin tregopil, insulin zinc suspension and insulin glargin; Gastric inhibitory Peptide (GIP); amylin and amylin analogues (e.g. pramlintide or davalintide); GLP-1 and GLP-1 analogues such as Exendin-4, e.g. exenatide, exenatide LAR, liraglutide, taspoglutide, lixisenatide (AVE-0010), LY-2428757 (a PEGylated version of GLP-1), dulaglutide (LY-2189265), semaglutide or albiglutide; SGLT2-inhibitors such as e.g. dapagliflozin, sergliflozin (KGT-1251), atigliflozin, canagliflozin, ipragliflozin or tofogliflozin; inhibitors of protein tyrosine-phosphatase (e.g. trodusquemine); inhibitors of glucose-6-phosphatase; fructose-1,6-bisphosphatase modulators; glycogen phosphorylase modulators; glucagon receptor antagonists; phosphoenolpyruvatecarboxykinase (PEPCK) inhibitors; pyruvate dehydrogenasekinase (PDK) inhibitors; inhibitors of tyrosine-kinases (50 mg to 600 mg) such as PDGF-receptor-kinase (cf. EP-A-564409, WO 98/35958, U.S. Pat. No. 5,093,330, WO 2004/005281, and WO 2006/041976) or of serine/threonine kinases; glucokinase/regulatory protein modulators incl. glucokinase activators; glycogen synthase kinase inhibitors; inhibitors of the SH2-domain-containing inositol 5-phosphatase type 2 (SHIP2); IKK inhibitors such as high-dose salicylate; JNK1 inhibitors; protein kinase C-theta inhibitors; beta 3 agonists such as ritobegron, YM 178, solabegron, talibegron, N-5984, GRC-1087, rafabegron, FMP825; aldosereductase inhibitors such as AS 3201, zenarestat, fidarestat, epalrestat, ranirestat, NZ-314, CP-744809, and CT-112; SGLT-1 or SGLT-2 inhibitors; KV 1.3 channel inhibitors; GPR40 modulators such as e.g. [(3S)-6-({2',6'-dimethyl-4'-[3-(methylsulfonyl)propoxy]biphenyl-3-yl}methoxy)-2,3-dihydro-1-benzofuran-3-yl]acetic acid; SCD-1 inhibitors; CCR-2 antagonists; dopamine receptor agonists (bromocriptine mesylate [Cycloset]); 4-(3-(2,6-dimethylbenzyloxy)phenyl)-4-oxobutanoic acid; sirtuin stimulants; and other DPP IV inhibitors.

Metformin is usually given in doses varying from about 500 mg to 2000 mg up to 2500 mg per day using various dosing regimens from about 100 mg to 500 mg or 200 mg to 850 mg (1-3 times a day), or about 300 mg to 1000 mg once or twice a day, or delayed-release metformin in doses of about 100 mg to 1000 mg or preferably 500 mg to 1000 mg once or twice a day or about 500 mg to 2000 mg once a day. Particular dosage strengths may be 250, 500, 625, 750, 850 and 1000 mg of metformin hydrochloride.

For children 10 to 16 years of age, the recommended starting dose of metformin is 500 mg given once daily. If this dose fails to produce adequate results, the dose may be increased to 500 mg twice daily. Further increases may be made in increments of 500 mg weekly to a maximum daily dose of 2000 mg, given in divided doses (e.g. 2 or 3 divided doses). Metformin may be administered with food to decrease nausea.

A dosage of pioglitazone is usually of about 1-10 mg, 15 mg, 30 mg, or 45 mg once a day.

Rosiglitazone is usually given in doses from 4 to 8 mg once (or divided twice) a day (typical dosage strengths are 2, 4 and 8 mg).

Glibenclamide (glyburide) is usually given in doses from 2.5-5 to 20 mg once (or divided twice) a day (typical dosage strengths are 1.25, 2.5 and 5 mg), or micronized glibenclamide in doses from 0.75-3 to 12 mg once (or divided twice) a day (typical dosage strengths are 1.5, 3, 4.5 and 6 mg).

Glipizide is usually given in doses from 2.5 to 10-20 mg once (or up to 40 mg divided twice) a day (typical dosage strengths are 5 and 10 mg), or extended-release glibenclamide in doses from 5 to 10 mg (up to 20 mg) once a day (typical dosage strengths are 2.5, 5 and 10 mg).

Glimepiride is usually given in doses from 1-2 to 4 mg (up to 8 mg) once a day (typical dosage strengths are 1, 2 and 4 mg).

A dual combination of glibenclamide/metformin is usually given in doses from 1.25/250 once daily to 10/1000 mg twice daily. (typical dosage strengths are 1.25/250, 2.5/500 and 5/500 mg).

A dual combination of glipizide/metformin is usually given in doses from 2.5/250 to 10/1000 mg twice daily (typical dosage strengths are 2.5/250, 2.5/500 and 5/500 mg).

A dual combination of glimepiride/metformin is usually given in doses from 1/250 to 4/1000 mg twice daily.

A dual combination of rosiglitazone/glimepiride is usually given in doses from 4/1 once or twice daily to 4/2 mg twice daily (typical dosage strengths are 4/1, 4/2, 4/4, 8/2 and 8/4 mg).

A dual combination of pioglitazone/glimepiride is usually given in doses from 30/2 to 30/4 mg once daily (typical dosage strengths are 30/4 and 45/4 mg).

A dual combination of rosiglitazone/metformin is usually given in doses from 1/500 to 4/1000 mg twice daily (typical dosage strengths are 1/500, 2/500, 4/500, 2/1000 and 4/1000 mg).

A dual combination of pioglitazone/metformin is usually given in doses from 15/500 once or twice daily to 15/850 mg thrice daily (typical dosage strengths are 15/500 and 15/850 mg).

The non-sulphonylurea insulin secretagogue nateglinide is usually given in doses from 60 to 120 mg with meals (up to 360 mg/day, typical dosage strengths are 60 and 120 mg); repaglinide is usually given in doses from 0.5 to 4 mg with meals (up to 16 mg/day, typical dosage strengths are 0.5, 1 and 2 mg). A dual combination of repaglinide/metformin is available in dosage strengths of 1/500 and 2/850 mg.

Acarbose is usually given in doses from 25 to 100 mg with meals. Miglitol is usually given in doses from 25 to 100 mg with meals.

Examples of combination partners that lower the lipid level in the blood are HMG-CoA-reductase inhibitors such as simvastatin, atorvastatin, lovastatin, fluvastatin, pravastatin, pitavastatin and rosuvastatin; fibrates such as bezafibrate, fenofibrate, clofibrate, gemfibrozil, etofibrate and etofyllinclofibrate; nicotinic acid and the derivatives thereof such as acipimox; PPAR-alpha agonists; PPAR-delta agonists such as e.g. {4-[(R)-2-ethoxy-3-(4-trifluoromethyl-phenoxy)-propylsulfanyl]-2-methyl-phenoxy}-acetic acid; inhibitors of acyl-coenzyme A:cholesterolacyltransferase (ACAT; EC 2.3.1.26) such as avasimibe; cholesterol resorption inhibitors such as ezetimib; substances that bind to bile acid, such as cholestyramine, colestipol and colesevelam; inhibitors of bile acid transport; HDL modulating active substances such as D4F, reverse D4F, LXR modulating active substances and FXR modulating active substances; CETP inhibitors such as torcetrapib, JTT-705 (dalcetrapib) or compound 12 from WO 2007/005572 (anacetrapib) or evacetrapib; LDL receptor modulators; MTP inhibitors (e.g. lomitapide); and ApoB100 antisense RNA.

A dosage of atorvastatin is usually from 1 mg to 40 mg or 10 mg to 80 mg once a day.

Examples of combination partners that lower blood pressure are beta-blockers such as atenolol, bisoprolol, celiprolol, metoprolol, nebivolol and carvedilol; diuretics such as hydrochlorothiazide, chlortalidon, xipamide, furosemide, piretanide, torasemide, spironolactone, eplerenone, amiloride and triamterene; calcium channel blockers such as amlodipine, nifedipine, nitrendipine, nisoldipine, nicardipine, felodipine, lacidipine, lercanipidine, manidipine, isradipine, nilvadipine, verapamil, gallopamil and diltiazem; ACE inhibitors such as ramipril, lisinopril, cilazapril, quinapril, captopril, enalapril, benazepril, perindopril, fosinopril and trandolapril; as well as angiotensin II receptor blockers (ARBs) such as telmisartan, candesartan, valsartan, losartan, irbesartan, olmesartan, azilsartan and eprosartan.

A dosage of telmisartan is usually from 20 mg to 320 mg or 40 mg to 160 mg per day.

Examples of combination partners which increase the HDL level in the blood are Cholesteryl Ester Transfer Protein (CETP) inhibitors; inhibitors of endothelial lipase; regulators of ABC1; LXRalpha antagonists; LXRbeta agonists; PPAR-delta agonists; LXRalpha/beta regulators, and substances that increase the expression and/or plasma concentration of apolipoprotein A-I.

Examples of combination partners for the treatment of obesity are sibutramine; tetrahydrolipstatin (orlistat); alizyme (cetilistat); dexfenfluramine; axokine; cannabinoid receptor 1 antagonists such as the CB1 antagonist rimonobant; MCH-1 receptor antagonists; MC4 receptor agonists; NPY5 as well as NPY2 antagonists (e.g. velneperit); beta3-AR agonists such as SB-418790 and AD-9677; 5HT2c receptor agonists such as APD 356 (lorcaserin); myostatin inhibitors; Acrp30 and adiponectin; steroyl CoA desaturase (SCD1) inhibitors; fatty acid synthase (FAS) inhibitors; CCK receptor agonists; Ghrelin receptor modulators; Pyy 3-36; orexin receptor antagonists; and tesofensine; as well as the dual combinations bupropion/naltrexone, bupropion/zonisamide, topiramate/phentermine and pramlintide/metreleptin.

Examples of combination partners for the treatment of atherosclerosis are phospholipase A2 inhibitors; inhibitors of tyrosine-kinases (50 mg to 600 mg) such as PDGF-receptor-kinase (cf. EP-A-564409, WO 98/35958, U.S. Pat. No. 5,093, 330, WO 2004/005281, and WO 2006/041976); oxLDL antibodies and oxLDL vaccines; apoA-1 Milano; ASA; and VCAM-1 inhibitors.

Further, within the meaning of this invention, optionally in addition, the DPP-4 inhibitor may be combined with one or more other antioxidants, anti-inflammatories and/or vascular endothelial protective agents.

Examples of antioxidant combination partners are selenium, betaine, vitamin C, vitamin E and beta carotene.

An example of an anti-inflammatory combination partner is pentoxifylline; another example of an anti-inflammatory combination partner is a PDE-4 inhibitor, such as e.g. tetomilast, roflumilast, or 3-[7-ethyl-2-(methoxymethyl)-4-(5-methyl-3-pyridinyl)pyrrolo[1,2-b]pyridazin-3-yl]propanoic acid (or other species disclosed in U.S. Pat. No. 7,153,854, WO 2004/063197, U.S. Pat. No. 7,459,451 and/or WO 2006/004188).

A further example of an anti-inflammatory partner drug is a caspase inhibitor, such as e.g. (3S)-5-fluoro-3-({[(5R)-5-isopropyl-3-(1-isoquinolinyl)-4,5-dihydro-5-isoxazolyl] carbonyl}amino-4-oxopentanoic acid (or other species disclosed in WO 2005/021516 and/or WO 2006/090997).

An example of a vascular endothelial protective agent is a PDE-5 inhibitor, such as e.g. sildenafil, vardenafil or tadalafil; another example of a vascular endothelial protective agent is a nitric oxide donor or stimulator (such as e.g. L-arginine or tetrahydrobiopterin).

Further, within the meaning of this invention, optionally in addition, the DPP-4 inhibitor may be combined with one or more antiplatelet agents, such as e.g. (low-dose) aspirin (acetylsalicylic acid), a selective COX-2 or nonselective COX-1/COX-2 inhibitor, or a ADP receptor inhibitor, such as a thienopyridine (e.g. clopidogrel or prasugrel), elinogrel or ticagrelor, or a thrombin receptor antagonist such as vorapaxar.

Yet further, within the meaning of this invention, optionally in addition, the DPP-4 inhibitor may be combined with one or more anticoagulant agents, such as e.g. heparin, warfarin, or a direct thrombin inhibitor (such as e.g. dabigatran), or a Faktor Xa inhibitor (such as e.g. rivaroxaban or apixaban or edoxaban or otamixaban).

Still yet further, within the meaning of this invention, optionally in addition, the DPP-4 inhibitor may be combined with one or more agents for the treatment of heart failure.

Examples of combination partners for the treatment of heart failure are beta-blockers such as atenolol, bisoprolol, celiprolol, metoprolol and nebivolol; diuretics such as hydrochlorothiazide, chlortalidone, xipamide, furosemide, piretanide, torasemide, spironolactone, eplerenone, amiloride and triamterene; ACE inhibitors such as ramipril, lisinopril, cilazapril, quinapril, captopril, enalapril, benazepril, perindopril, fosinopril and trandolapril; angiotensin II receptor blockers (ARBs) such as telmisartan, candesartan, valsartan, losartan, irbesartan, olmesartan and eprosartan; heart glycosides such as digoxin and digitoxin; combined alpha/beta-blockers such as carvedilol; vasodilators; antiarrhythmic drugs; or B-type natriuretic peptide (BNP) and BNP-derived peptides and BNP-fusion products.

Moreover, within the meaning of this invention, optionally in addition, a DPP-4 inhibitor may be combined with one or more CCK-2 or gastrin agonists, such as e.g. proton pump inhibitors (including reversible as well as irreversible inhibitors of the gastric H+/K+-ATPase), for example omeprazole, esomeprazole, pantoprazole, rabeprazole or lansoprazole.

The present invention is not to be limited in scope by the specific embodiments described herein. Various modifications of the invention in addition to those described herein may become apparent to those skilled in the art from the present disclosure. Such modifications are intended to fall within the scope of the appended claims.

All patent applications cited herein are hereby incorporated by reference in their entireties.

Further embodiments, features and advantages of the present invention may become apparent from the following examples. The following examples serve to illustrate, by way of example, the principles of the invention without restricting it.

EXAMPLES

Antioxidant Effects
Anti-Inflammatory and Vasodilatory Potential of Linagliptin

Direct antioxidant effects of gliptins (linagliptin, alogliptin, vildagliptin, saxagliptin, sitagliptin) are assessed by interfering with superoxide formation from xanthine oxidase, peroxynitrite (authentic and Sin-1 derived) or hydrogen peroxide/peroxidase mediated 1-electron-oxidation. These oxidations are detected by fluorescence, chemiluminescence and nitration of phenols (traced by HPLC). Indirect antioxidant effects of gliptins are measured in isolated human leukocytes (PMN) by interfering with oxidative burst (NADPH oxidase activation) induced by the phorbol ester PDBu, the endotoxines LPS and zymosan A and the chemotactic peptide fMLP.

Direct vasodilatory effects of gliptins are measured by the isometric tension technique in isolated aortic ring segments. Indirect antioxidant effects of linagliptin are also tested in a rat model of nitroglycerin-induced nitrate tolerance and linagliptin treatment (3-10 mg/kg/d by special diet for 7 d) by determination of endothelial function (acetylcholine-dependent relaxation of phenylephrine preconstricted aortic vessel segments), smooth muscle function (nitroglycerin-dependent relaxation) by isometric tension recordings. In addition reactive oxygen and nitrogen species (RONS) formation is determined in isolated cardiac mitochondria and LPS or PDBu-triggered oxidative burst in whole blood. Also, the anti-inflammatory potential of linagliptin is tested in an experimental model of LPS (10 mg/kg i.p. for 24 h)-induced septic shock in Wistar rats. The effects of sepsis and linagliptin cotherapy (3-10 mg/kg/d by special diet for 7 d) are assessed by isometric tension recordings, vascular, cardiac, and blood RONS formation and protein expression by Western blotting.

Results:
(See FIGS. 1-6)
Direct Antioxidant Properties:

All gliptins only show marginal direct antioxidant capacity. Minor (but significant) suppression of superoxide formation is observed for vildagliptin and for linagliptin in response to peroxynitrite formation/-mediated nitration. All gliptins except saxagliptin show significant interference with 1-electron-oxidations by the hydrogen peroxide/peroxidase system with linagliptin being the most potent compound.

Indirect Antioxidant Properties in Isolated Human Neutrophils:

Linagliptin shows the best inhibition of oxidative burst in isolated human leukocytes in response to NADPH oxidase activation by LPS and zymosan A. Using L-012 enhanced chemiluminescence, LPS (0.5, 5 and 50 µg/ml) increases the PMN derived RONS signal in a concentration-dependent fashion and linagliptin suppresses the signal concentration-dependently.

In experiments with luminol/peroxidase enhances chemiluminescence, linagliptin is much more efficient in suppressing LPS or zymosan A-triggered oxidative burst in isolated PMN than other gliptins. In this assay, linagliptin is as efficient as nebivolol. The efficiency to inhibit LPS-dependent RONS formation is somewhat more pronounced than the suppressing effect on zymosan A-triggered RONS. All of these measurements support a superior antioxidant effect of linagliptin in isolated neutrophils as compared to other gliptins.

Inhibition of Adhesion of Activated Neutrophils to Endothelial Cells:

By studying the adhesion of LPS-stimulated human neutrophils to cultured endothelial cells (the number of adherent PMN correlates with the PDBu-triggered oxidative burst which can be measured amplex red/peroxidase fluorescence), linagliptin suppresses leukocyte adhesion to endothelial cells in the presence of LPS.

Figure 7A:
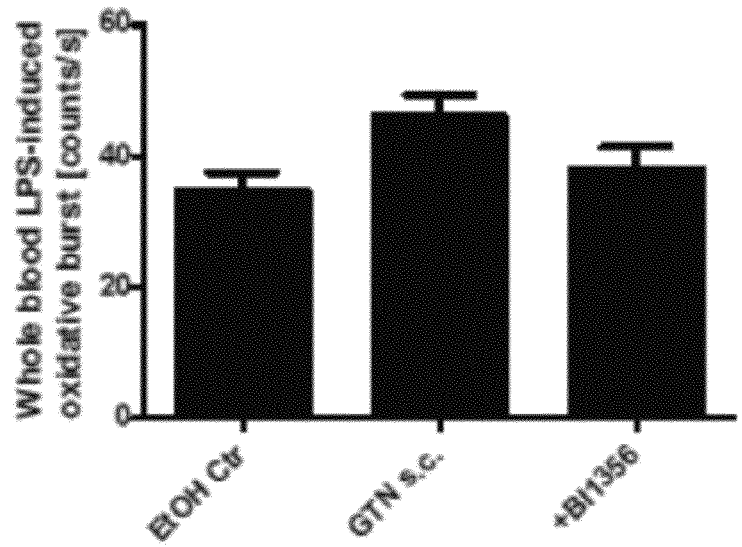
FIGS. 7A and 7B show the effect of linagliptin on whole blood oxidative burst/oxidative stress in nitroglycerin-induced nitrate tolerance (LPS=lipopolysaccharide, EtOH Ctr=ethanol control, GTN s.c.=glyceryl trinitrate—subcutaneous, BI1356=linagliptin).
Figure 7B:
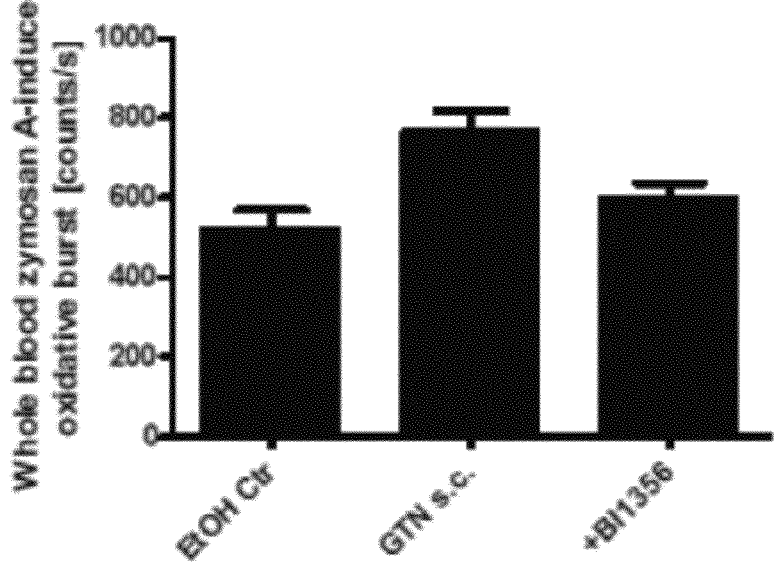
Figure 8A:
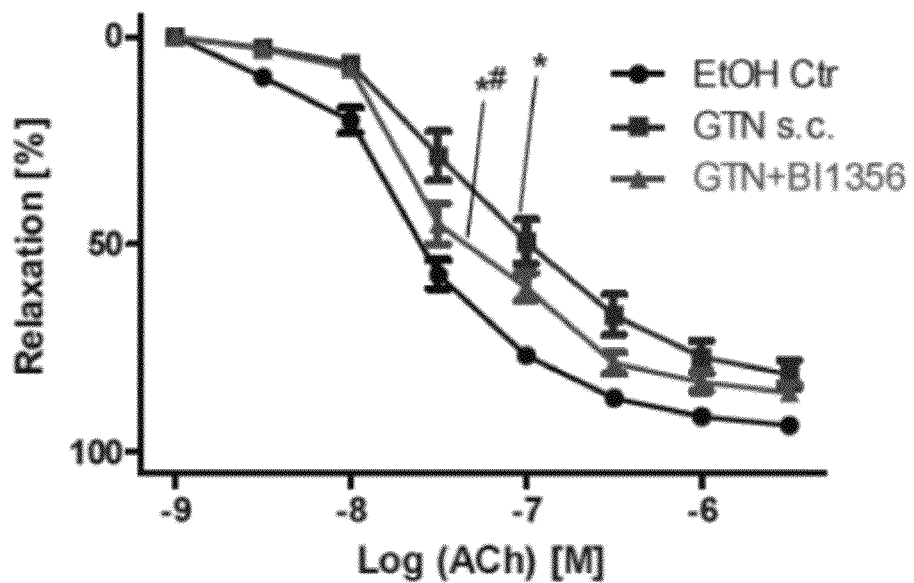
FIG. 8A and FIG. 8B show the improvement of endothelial dysfunction by linagliptin in GTN or LPS treated rats (pre-treatment with linagliptin (3-10 mg/kg, induction of endothelial dysfunction by nitrates or LPS (3 days)
Figure 8B:
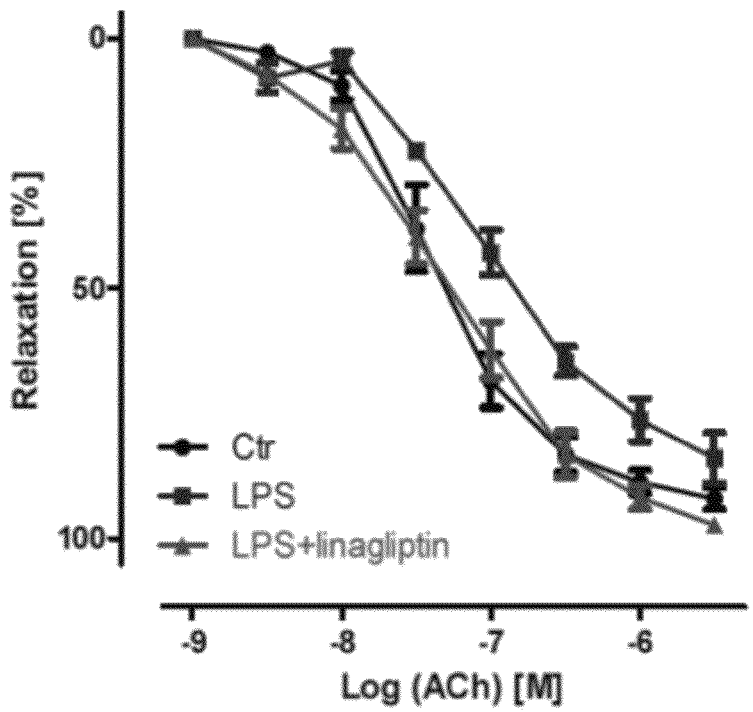

Treatment of Vascular Dysfunction and/or Oxidative Stress:
Effects of Oral Linagliptin Treatment on Vascular Dysfunction and Oxidative Stress in Nitrate Tolerant Rats:

Isometric tension studies in organ baths reveal that nitroglycerin and LPS treatment induces remarkable endothelial dysfunction and nitrate tolerance. Endothelial dysfunction caused by both factors is significantly improved by linagliptin therapy (FIGS. 8A and 8B) whereas nitrate tolerance is not altered. Nitroglycerin treatment evokes an increase in cardiac mitochondrial ROS formation and whole blood LPS/zymosan A-triggered oxidative burst. All of these adverse effects are improved by linagliptin treatment (FIG. 7). Neither nitroglycerin nor linagliptin treatment has effects on body weight of the animals whereas blood glucose levels are slightly increased in the nitroglycerin group which is normalized by linagliptin treatment.

Summarized, linagliptin in vivo treatment ameliorates nitroglycerin-induced endothelial dysfunction and shows minor improvement of ROS formation in isolated cardiac mitochondria and oxidative burst in whole blood from nitrate-tolerant rats.

Effects of Linagliptin Treatment on Vascular Dysfunction and Oxidative Stress in Septic Rats:

Very similar protective effects for linagliptin are observed in an experimental model of septic shock. Vascular function (Ach-, GTN-, and diethylamine NONOate-dependent relaxation) are largely impaired by LPS and almost normalized by linagliptin therapy. Mitochondrial and whole blood (LPS, PDBu-stimulated) RONS production is dramatically increased by LPS and improved by linagliptin treatment. Vascular oxidative stress (measured by DHE-dependent fluorescent microtopography) and markers of vascular inflammation (VCAM-1, Cox-2, and NOS-2) are dramatically increased by LPS treatment and significantly improved by linagliptin therapy. Similar effects are observed for aortic protein tyrosine nitration and malondialdehyde content (both markers for oxidative stress) as well as aortic NADPH oxidase subunit expression (Nox1 and Nox2). As proof of concept DPP-4 activity and GLP-1 levels are detected from the respective animals and demonstrate potent inhibition of DPP-4 and an approximate 10-fold increase of plasma GLP-1 levels.

Figure 9A:
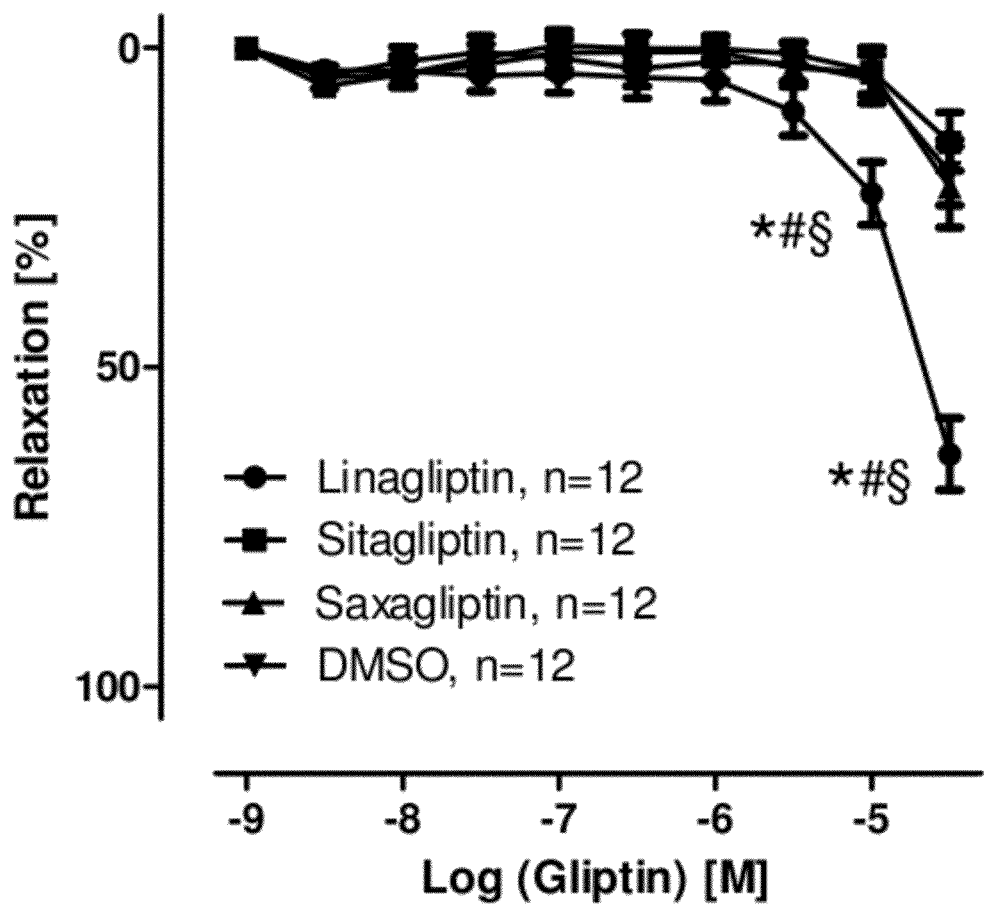
FIGS. 9A and 9B show direct vasodilatory effects of gliptins. Gliptin-induced vasodilation is determined by isometric tension recording in isolated aortic ring segments and relaxation in response to increasing cumulative concentrations (1 nM to 32 μM) of linagliptin, sitagliptin, or saxagliptin (FIG. 9A). In another set of experiments the aortic relaxation in response to increasing cumulative concentrations (1 nM to 32 or 100 μM) of linagliptin, alogliptin, or vildagliptin is tested (FIG. 9B). The data are mean±SEM of 12 (FIG. 9A) or 4 (FIG. 9B) aortic rings from 10 rats in total. *, $p<0.05$ vs. DMSO (solvent control); #, $p<0.05$ vs. sita-/vildagliptin and §, $p<0.05$ vs. saxa-/alogliptin.
Figure 9B:
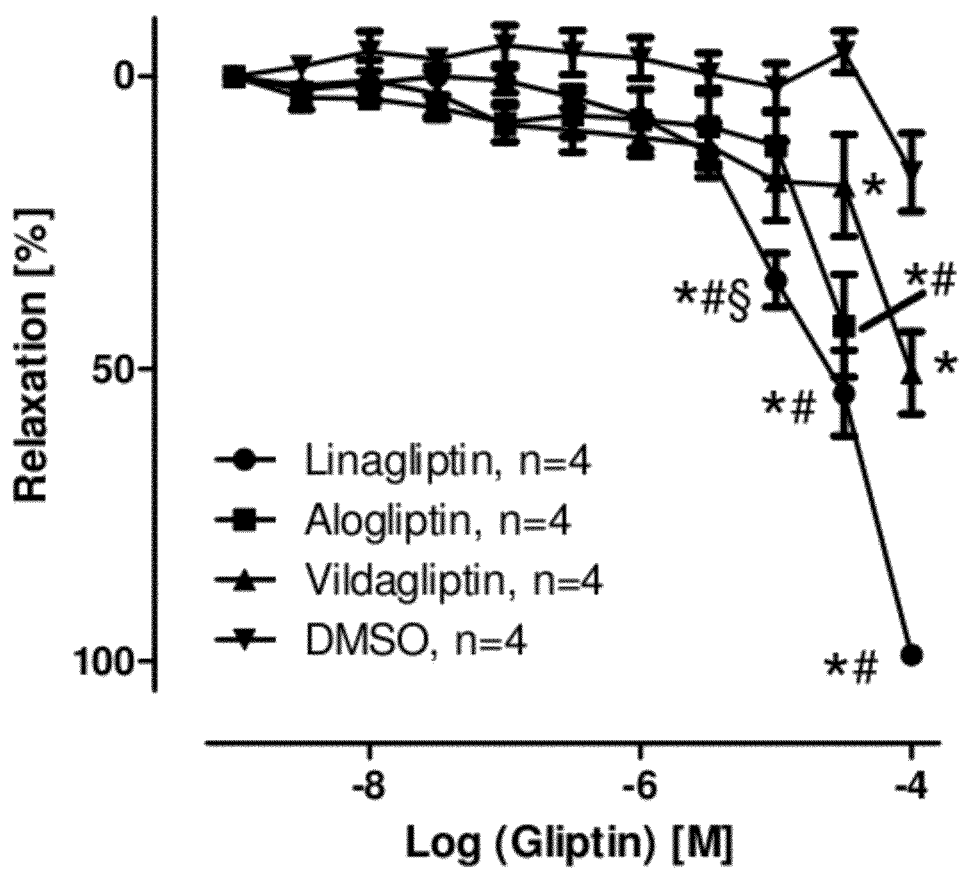

Direct Vasodilatory Effects of Gliptins:

Isometric tension recording reveals that several gliptins display direct vasodilatory effects in the concentration range of 10-100 µM. Linagliptin is the most potent compound directly followed by alogliptin and vildagliptin, whereas sitagliptin and saxagliptin are not more efficient in the induction of vasodilation than the solvent alone control (DMSO) (see FIGS. 9A and 9B).

These observations support pleiotropic antioxidant and anti-inflammatory properties of linagliptin, which are not (or to a minor extent) shared by other gliptins. Furthermore, linagliptin reduces leukocyte adhesion to endothelial cells due to the presence of LPS and improves nitroglycerin- and inflammation-induced endothelial dysfunction and oxidative stress. This may contribute to improved endothelial function and support of cardioprotective action of linagliptin. Thus, there is evidence that linagliptin confers antioxidant effects that beneficially influence cardiovascular diseases, which are secondary to diabetic complications with high levels of morbidity and mortality.

Treatment of Diabetic Nephropathy and Albuminuria:

Endothelial damage is characteristic for type 2 diabetes and contributes to the development of end stage kidney disease. Further, vascular endothelial NO synthase (eNOS) activity is altered in T2D and genetic abnormalities in the respected gene (NOS3) are associated with the development of advanced diabetic nephropathy (DN) in patients with type 1 and type 2 diabetes. The use of low dose STZ to induce T2D in this genetic phenotype (eNOS–/–) has been recently reported (Brosius et al, JASN 2009) to be a valid experimental model for DN.

Eight week old eNOS –/– mice are rendered diabetic with intraperitoneal injections of streptozotocin (100 mg/kg per day for two consecutive days). Development of diabetes (defined by blood glucose >250 mg/dl) is verified one week after streptozotocin injection. No insulin is given because that could prevent the development of diabetic nephropathy. Mice are treated for 4 weeks with:

1) Non-diabetic eNOS ko control mice, placebo (natrosol) (n=14)
2) sham treated diabetic eNOS ko mice, placebo (natrosol) (n=17)
3) Telmisartan (p.o. 1 mg/kg) treated diabetic eNOS ko mice (n=17)
4) Linagliptin inhibitor (p.o. 3 mg/kg) treated diabetic eNOS ko mice (n=14)
5) Telmisartan (1 mg/kg)+Linagliptin (3 mg/kg) treated diabetic eNOS ko mice (n=12)

Figure 10:
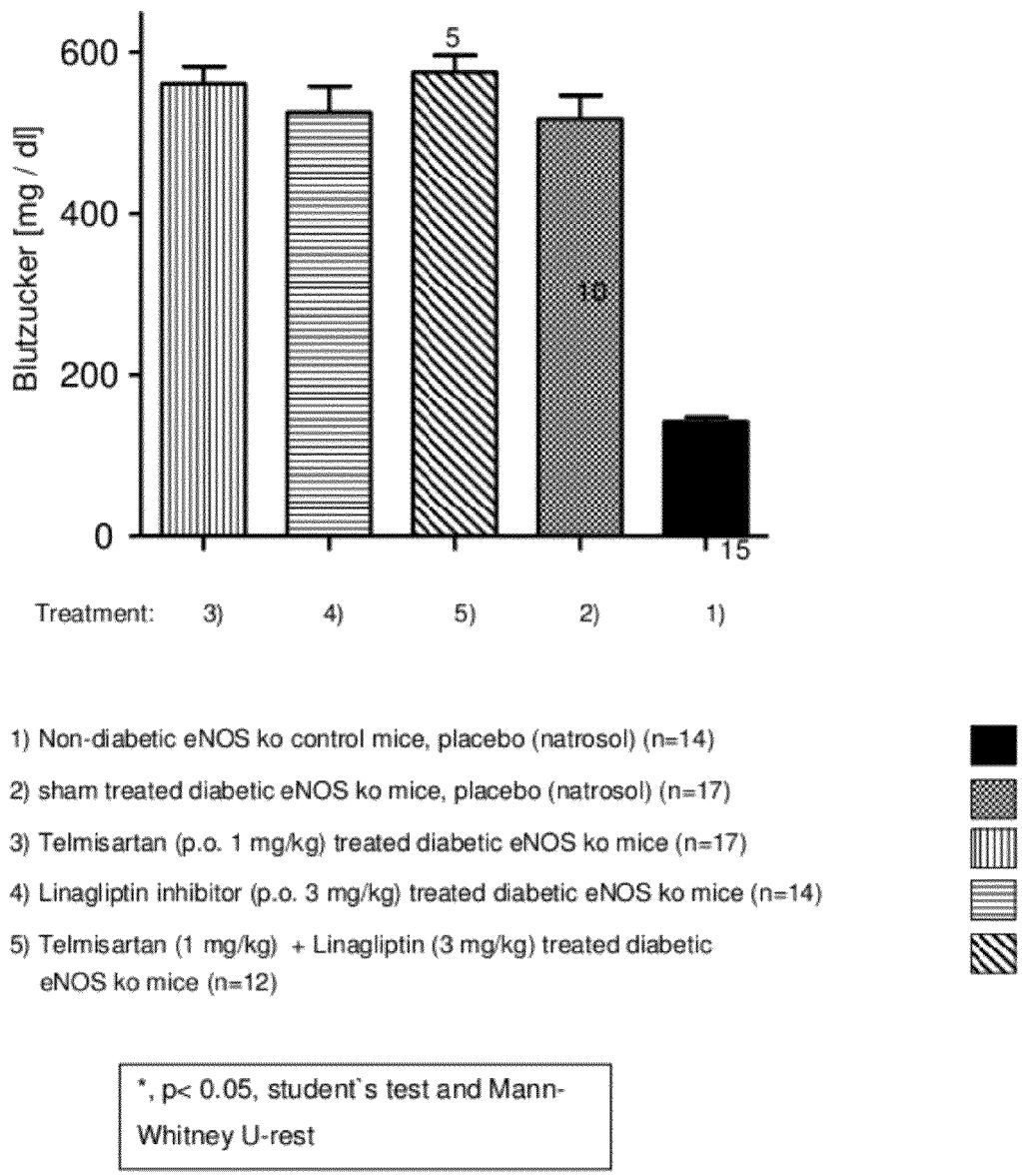
FIG. 10 shows the renal function based on detected blood sugar after treatment with linagliptin, telmisartan or the combination versus placebo in STZ treated animals:
1) Non-diabetic eNOS ko control mice, placebo (natrosol) (n=14)
2) sham treated diabetic eNOS ko mice, placebo (natrosol) (n=17)
3) Telmisartan (p.o. 1 mg/kg) treated diabetic eNOS ko mice (n=17)
4) Linagliptin (p.o. 3 mg/kg) treated diabetic eNOS ko mice (n=14)
5) Telmisartan (1 mg/kg)+Linagliptin (3 mg/kg) treated diabetic eNOS ko mice (n=12).

Renal function (s-creatinine, albuminuria) and blood glucose level are detected. No significant differences on blood sugar are detected after treatment with linagliptin, telmisartan or the combination versus placebo in STZ treated animals (see FIG. 10).

Figure 11:
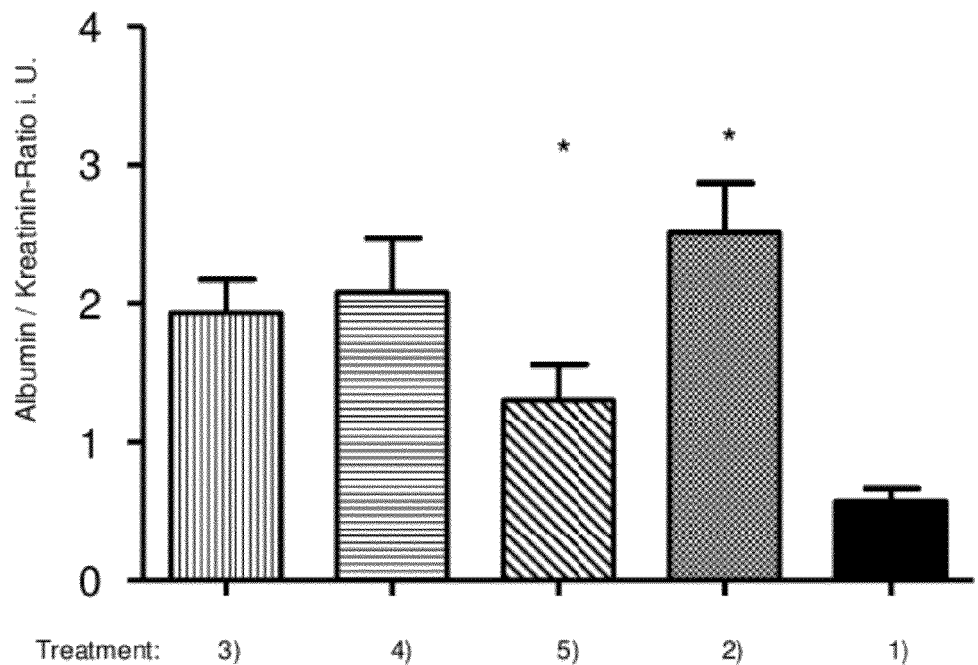
FIG. 11 shows the Albumin/creatinin ratio of non-diabetic versus diabetic animals:
1) Non-diabetic eNOS ko control mice, placebo (natrosol) (n=14)
2) sham treated diabetic eNOS ko mice, placebo (natrosol) (n=17)
3) Telmisartan (p.o. 1 mg/kg) treated diabetic eNOS ko mice (n=17)
4) Linagliptin (p.o. 3 mg/kg) treated diabetic eNOS ko mice (n=14)
5) Telmisartan (1 mg/kg)+Linagliptin (3 mg/kg) treated diabetic eNOS ko mice (n=12).
Figure 11:
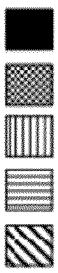

Despite no effect on the blood glucose is detected, the albumin/creatinin ratio is significantly reduced in the group receiving linagliptin+telmisartan (mid bar, No. 5 in FIG. 11). The respective mono treatment lowers also the albumin/creatinin ratio, however not reaching significance. Also the albumin/creatinin ratio of non-diabetic versus diabetic animals are reduced significantly (see FIG. 11). These effects support the use of linagliptin and telmisartan in renoprotection and in treating and/or preventing diabetic nephropathy and albuminuria. The combination of linagliptin and telmisartan offers a new therapeutic approach for patients with or at risk of diabetic nephropathy and albuminuria.

Treatment of Congestive Heart Failure and Cardiac Hypertrophy:

We hypothesize that glucose/energy supply is particularly important in the failing heart that is characterized by cardiac hypertrophy. Inadequate energy supply is considered as one of the most important steps from compensated to decompensated left ventricular hypertrophy resulting in heart failure. A classical model of hypertension induced left ventricular hypertrophy that results on the long run in left ventricular failure and pathological remodeling is the two-kidney-one clip reno-vascular hypertension (Goldblatt) model (2K1C model).

Animals are treated 3 months with the following regimen:
1. 2K1C-rats, Telmisartan in drinking water (10 mg/kg KG) (n=14)
2. 2K1C-rats, Linagliptin (BI1356) in chow (89 ppm, corresponding to 3-10 mg/kg oral gavage) (n=15)
3. 2K1C-rats, Telmisartan (10 mg/kg)+Linagliptin (BI1356) in chow (89 ppm) (n=15)
4. 2K1C-rats, placebo (n=17)
5. SHAM-rats, placebo (n=11)

Non-invasive, systolic blood pressure is measured in all groups to the time points (1. before treatment; 2. after 1 weeks 3. after 4 weeks; 4. after 6 weeks 5. after 12 weeks; and 6. after 6 weeks of treatment with the respective compounds.

Figure 12:
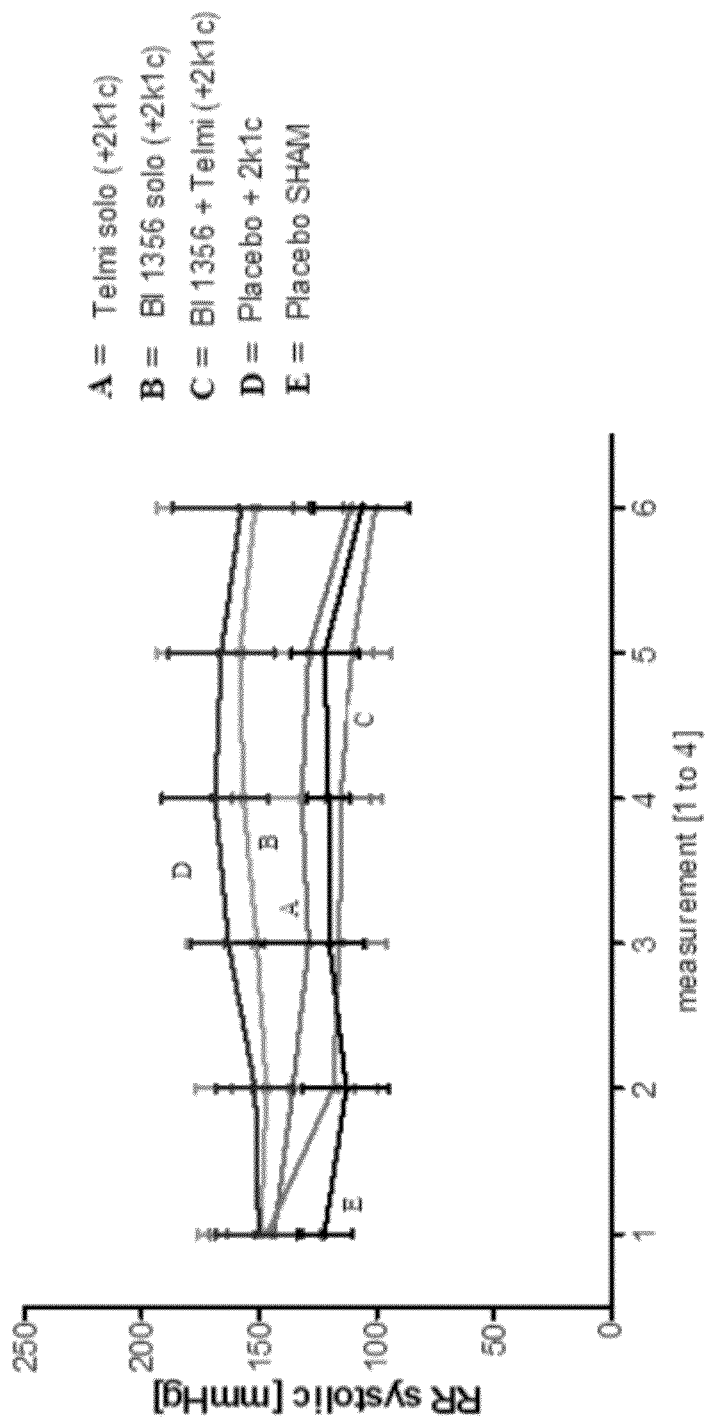
FIG. 12 shows the results of a rat study showing effects of combination of telmisartan (Telmi) with linagliptin (BI 1356), and mono treatment of temisartan (Telmi solo) or of linagliptin (BI 1356 solo) on blood pressure in a model of hypertension induced cardiac hypertrophy resulting in heart failure.

Before treatment only the sham treated animals are significant different to all other groups. From week 1 of treatment until the end of the study telmisartan and the combination of telmisartan with linagliptin are always significant versus vehicle treated animals. The combination of telmisartan with linagliptin reaches the level of placebo treated sham animals and shows additional effects to the mono treatment of temisartan (see FIG. 12). These effects support the use of linagliptin and telmisartan in treating and/or preventing cardiac hypertrophy and/or congestive heart failure. The combination of linagliptin and telmisartan offers a new therapeutic approach for patients with or at risk of cardiac hypertrophy and/or congestive heart failure.

Treatment of Uremic Cardiomyopathy:

Uremic cardiomyopathy contributes substantially to morbidity and mortality of patients with chronic kidney disease, which is in turn also a frequent complication of type 2 diabetes. Glucagon-like peptide-1 (GLP-1) may improve cardiac function and GLP-1 is mainly degraded by dipeptidyl peptidase-4 (DPP-4). Linagliptin is the only DPP-4 inhibitor that can be used clinically (e.g. in patients with type 2 diabetes and diabetic nephropathy) at all stages of renal insufficiency without dose adjustment.

It is investigated linagliptin in a rat model of chronic renal insufficiency (5/6 nephrectomy [5/6N])

Eight weeks after 5/6N or sham surgery, rats are treated orally with 3.3 mg/kg linagliptin or vehicle for 4 days, and, subsequently, plasma is sampled for 72 h for quantification of DPP-4 activity and GLP-1 levels. At the end of the study, heart tissue is harvested for mRNA analyses.

Figures 13, 14:
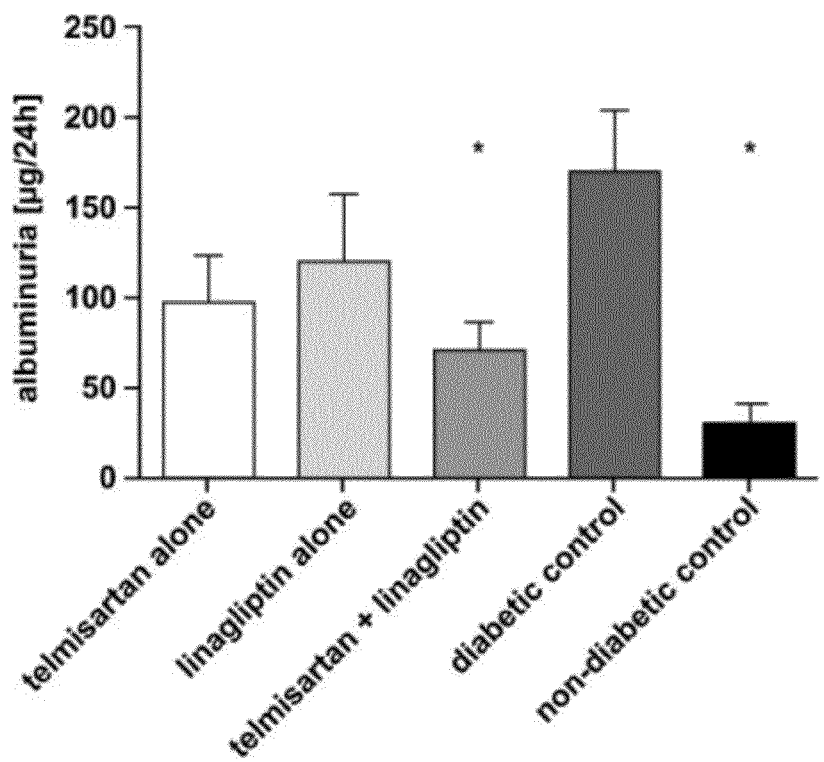
FIG. 13 is a table showing the results of a study in rat model of chronic renal insufficiency showing effects of linagliptin on markers of cardiac fibrosis and markers of left ventricular dysfunction in heart tissue (TGF-β=transforming growth factor beta, TIMP=tissue inhibitor of metalloproteinase, Col1β=collagen type 1 alpha, Col3α=collagen type 3 alpha, BNP=B-type natriuretic peptide).
FIG. 14 shows the results of a study in diabetic eNOS knockout C57BL/6J mice as model of diabetic nephropathy that is refractory to ARB treatment showing effects of linagliptin and telmisartan on albuminuria.

5/6N causes a significant (p<0.001) decrease in GFR measured by creatinine clearance (sham: 2510±210 mU24 h; 5/6N: 1665±104.3 mU24 h) and increased cystatin C levels (sham: 700±35.7 ng/mL; 5/6N: 1434±77.6 ng/mL). DPP-4 activity is significantly reduced at all time points with no difference between sham or 5/6N animals. In contrast, active GLP-1 levels are significantly increased in 5/6N animals, as measured by the maximum plasma concentration ($C_{max}$; 5/6N, 6.36±2.58 µg/mL vs sham: 3.91±1.86 µg/mL; p<0.001) and $AUC_{(0-72h)}$ (5/6N: 201 µg·h/mL vs sham: 114 µg·h/mL; p<0.001). The mRNA levels of cardiac fibrosis markers (profibrotic factors) such as TGF-β, tissue inhibitor of matrix metalloproteinase 1 (TIMP-1) and collagens 1α1 and 3α1 as well as markers of left ventricular dysfunction such as brain natriuretic peptide (BNP) are all significantly increased in 5/6N versus sham animals and consequently are reduced or even normalized by linagliptin treatment (all p<0.05, see FIG. 13).

Linagliptin increases the AUC of GLP-1 approximately twofold in a rat model of renal failure, and decreases gene expression of BNP, a marker of left ventricular dysfunction, as well as markers of cardiac fibrosis (TGF-β, TIMP-1, Col 1α1 and Col 3α1) in hearts of uremic rats. These effects support the use of linagliptin in treating and/or preventing uremic cardiomyopathy. Linagliptin offers a new therapeutic approach for patients with uremic cardiomyopathy.

Effect on Infarction Size and Cardiac Function after Myocardial Ischemia/Reperfusion:

The objective of this study is to evaluate the cardiac effects (particularly on myocardial ischemia/reperfusion, cardiac function or infarcation size) of a xanthine based DPP-4 inhibitor of this invention, such as e.g. in conditions involving stromal cell-derived factor-1 alpha (SDF-1α).

Male Wistar rats are divided into 3 groups: sham, ischemia/reperfusion (I/R), and I/R+DPP-4 inhibitor of this invention; n=10-12 per group. The DPP-4 inhibitor is given once daily starting 2 days before I/R. The left anterior descending coronary artery is ligated for 30 min. Echocardiography is performed after 5 days and cardiac catheterization after 7 days. The DPP-4 inhibitor significantly reduces the absolute infarction size (−27.8%; p<0.05), the proportion of infarcted tissue relative to the total area at risk (−18.5%; p<0.05) and the extent of myocardial fibrosis (−31.6%; p<0.05). The DPP-4 inhibitor significantly increases the accumulation of stem/progenitor cells as characterized by CD34-, CXCR4-, and C-kit-expression and the cardiac immunoreactivity for active SDF-1a in the infarcted myocardium. Left ventricular ejection fraction is similar in all MI groups after 7 days, however, the DPP-4 inhibition reduces infarct size, reduces fibrotic remodelling and increases the density of stem cells in infarcted areas by blocking the degradation of SDF-1α.

A xanthine based DPP-4 inhibitor of this invention is able to reduce infarct size after myocardial infarct. Mechanisms of action may include reduced degradation of SDF-1α with subsequent increased recruitment of circulating CXCR-4$^+$ stem cells and/or incretin receptor dependent pathways.

These data strengthen the usability of a xanthine based DPP-4 inhibitor of this invention for increasing recruitment of stem cells, improving tissue repair, activating myocardial regeneration, reducing infarct size, reducing fibrotic remodelling and/or increasing density of stem cells in infarcted cardiac areas in the treatment or prevention of myocardial ischemia/reperfusion and/or in cardio-protecting.

Based on that infarct size is a predictor of future events (including mortality), it is postulated that a xanthine based DPP-4 inhibitor of this invention may be further useful for improving cardiac (systolic) function, cardiac contractility and/or mortality after myocardial ischemia/reperfusion.

Effect of Linagliptin on Infarction Size and Cardiac Function after Myocardial Ischemia/Reperfusion:

Materials and methods: Male Wistar rats are divided into three groups: sham, I/R and I/R plus linagliptin (n=16-18 per group). Linagliptin is given once daily (3 mg/kg) starting 30 days before I/R. I/R is induced by ligation of the left anterior descending coronary artery for 30 min, Echocardiography is performed after 58 days and cardiac catheterization after 60 days.

Linagliptin significantly reduces the proportion of infarcted tissue relative to the total area at risk (−21%; p<0.001) as well as the absolute infarction size (−18%; p<0.05) in this ischemia reperfusion injury (I/R) model. In addition, glucagon-like peptide-1 (GLP-1) levels are increased 18-fold (p<0.0001) and DPP-4 activity is reduced by 78% (p<0.0001). Left ventricular left end diastolic and systolic pressure as well all echocardiography parameters are similar between groups, with a significant improvement of isovolumetric contractility indices (dP/dT$_{min}$) from −4771±79 mmHg/s to −4957±73 mmHg/s or improved maximum rate of left ventricular pressure decline. These data further support a cardioprotective function of linagliptin in the setting of acute myocardial infarction.

Treating ARB-Resistant Diabetic Nephropathy:

The need for an improved treatment for diabetic nephropathy is greatest in patients who do not adequately respond to angiotensin receptor blockers (ARBs). This study investigates the effect of linagliptin, alone and in combination with the ARB telmisartan, on the progression of diabetic nephropathy in diabetic eNOS knockout mice, a new model closely resembling human pathology.

Sixty-five male eNOS knockout C57BL/6J mice are divided into 4 groups after receiving intraperitoneal high-dose streptozotocin: telmisartan (1 mg/kg), linagliptin (3 mg/kg), linagliptin+telmisartan (3+1 mg/kg), and vehicle. Fourteen mice are used as non-diabetic controls. After 12 weeks, urine and blood are obtained and blood pressure measured. Glucose concentrations are increased and similar in all diabetic groups. Telmisartan alone reduces blood pressure modestly by 5.9 mmHg vs diabetic controls (111.2±2.3 mmHg vs 117.1±2.2 mmHg; mean±SEM; n=14 each; p=0.071) and none of the other treatments reaches significance. Combined treatment significantly reduces albuminuria (e.g. urinary albumin excretion per 24 h and/or the albumin/creatinine ration) compared with diabetic controls (71.7±15.3 µg/24 h vs 170.8±34.2 µg/24 h; n=12-13; p=0.017), whereas the effects of single treatment with either telmisartan (97.8±26.4 µg/24 h; n=14) or linagliptin (120.8±37.7 µg/24 h; n=11) are not statistically significant (see FIG. 14). Linagliptin, alone and in combination, leads to significantly lower plasma osteopontin levels compared with telmisartan alone where values are similar to diabetic controls. Plasma TNF-α concentrations are significantly lower in all treatment groups than with vehicle. Plasma neutrophil gelatinase-associated lipocalin (NGAL) levels are significantly increased after treatment with telmisartan compared with untreated diabetic mice, this effect is prevented by combined treatment with linagliptin.

Further, linagliptin, alone and in combination with telmisartan, leads to a significantly reduced glomerulosclerosis in the kidney measured by histological score compared with diabetic controls (2.1+/−0.0 vs 2.4+/−0.0; p<0.05), whereas the reduction achieved by telmisartan alone is not significantly different. In conclusion, linagliptin significantly reduces urinary albumin excretion in diabetic eNOS knockout mice that are refractory to ARB (e.g. in a blood pressure-independent manner). These effects may support the use of linagliptin in renoprotection and in treating and/or preventing ARB-resistant diabetic nephropathy. Linagliptin may offer a new therapeutic approach for patients resistant to ARB treatment.

Delaying Onset of Diabetes and Preserving Beta-Cell Function in Non-Obese Type-1 Diabetes:

Though reduced pancreatic T-cell migration and altered cytokine production is considered important players for the onset of insulinitis the exact mechanism and effects on the pancreatic cell pool is still incompletely understood. In an attempt to evaluate the effect of linagliptin on pancreatic inflammation and beta-cell mass it is examined the progression of diabetes in the non-obese-diabetic (NOD) mice over a 60 day experimental period coupled with terminal stereological assessment of cellular pancreatic changes.

Sixty female NOD mice (10 weeks of age) are included in the study and fed a normal chow diet or a diet containing linagliptin (0.083 g linagliptin/kg chow; corresponding to 3-10 mg/kg, p.o) throughout the study period. Bi-weekly plasma samples are obtained to determine onset of diabetes (BG>11 mmol/l). At termination, the pancreata are removed and a terminal blood sample is obtained for assessment of active GLP-1 levels. At the end of the study period the incidence of diabetes is significantly decreased in linagliptin-treated mice (9 out of 30 mice) compared with the control group (18 of 30 mice, p=0.021). The subsequent stereological assessment of beta-cell mass (identified by insulin immunoreactivity) demonstrates a significantly larger beta cell mass (veh 0.18±0.03 mg; lina 0.48±0.09 mg, p<0.01) and total islet mass (veh 0.40±0.04 mg; lina 0.70±0.09 mg, p<0.01) in linagliptin treated mice. There is a tendency for linagliptin to reduce peri-islet infiltrating lymphocytes (1.06±0.15; lina 0.79±0.12 mg, p=0.17). As expected active plasma GLP-1 are higher at termination in linagliptin treated mice.

In summary, the data demonstrate that linagliptin is able to delay the onset of diabetes in a type-1 diabetic model (NOD mouse). The pronounced beta-cell sparing effects which can be observed in this animal model indicate that such DPP-4 inhibition not only protects beta-cells by increasing active GLP-1 levels, but may also exerts direct or indirect anti-inflammatory actions. These effects may support the use of linagliptin in treating and/or preventing type 1 diabetes or latent autoimmune diabetes in adults (LADA). Linagliptin may offer a new therapeutic approach for patients with or at-risk of type 1 diabetes or LADA.

Effect of Linagliptin on Body Weight Total Body Fat, Liver Fat and Intramyocellular Fat In a further study the efficacy of chronic treatment with linagliptin on body weight, total body fat, intra-myocellular fat, and hepatic fat in a non-diabetic model of diet induced obesity (DIO) in comparison to the appetite suppressant subutramine is investigated:

Rats are fed a high-fat diet for 3 months and received either vehicle, linagliptin (10 mg/kg), or sibutramine (5 mg/kg) for 6 additional weeks, while continuing the high-fat diet. Magnetic resonance spectroscopy (MRS) analysis of total body fat, muscle fat, and liver fat is performed before treatment and at the end of the study.

Sibutramine causes a significant reduction of body weight (−12%) versus control, whereas linagliptin has no significant effect (−3%). Total body fat is also significantly reduced by sibutramine (−12%), whereas linagliptin-treated animals show no significant reduction (−5%). However, linagliptin and sibutramine result both in a potent reduction of intramyocellular fat (−24% and −34%, respectively). In addition, treatment with linagliptin results in a profound decrease of hepatic fat (−39%), whereas the effect of sibutramine (−30%) does not reach significance (see Table below). Thus, linagliptin is weight neutral but improves intra-myocellular and hepatic lipid accumulation. A reduction of steatosis, inflammation and fibrosis in the liver measured by histological scoring is also observed for linagliptin treatment.

In conclusion, linagliptin treatment provokes a potent reduction of intramyocellular lipids and hepatic fat, which are both independent of weight loss. The treatment with linagliptin provides additional benefit to patients with diabetes who are additionally affected by liver steatosis (e.g. NAFLD). The effects of sibutramine on muscular and hepatic fat are attributed mainly to the known weight reduction induced by this compound.

Linagliptin Has Similar Efficacy to Glimepiride but Improves Cardiovascular Safety Over 2 Years in Patients with Type 2 Diabetes Inadequately Controlled on Metformin:

In a 2-year double-blind trial the long-term efficacy and safety of adding linagliptin or glimepiride to ongoing metformin to treat type 2 diabetes (T2DM) is investigated. T2DM patients on stable metformin (≥1500 mg/d) for ≥10 weeks are randomized to linagliptin 5 mg/day (N=764) or glimepiride 1-4 mg/day (N=755) over 2 years. Efficacy analyses are based on HbA1c change from baseline in the full analysis set (FAS) and per-protocol (PP) population. Safety evaluations include pre-specified, prospective, and adjudicated capture of cardiovascular (CV) events (CV death, non-fatal myocardial infarction or stroke, unstable angina with hospitalization). Baseline characteristics are well balanced in the 2 groups (HbA1c 7.7% for both). In the PP population, adjusted mean (±SE) HbA1c changes from baseline are −0.4% (±0.04%) for linagliptin 5 mg/day vs −0.5% (±0.04%) for glimepiride (mean dose 3 mg/day). Mean between-group difference is 0.17% (95% CI, 0.08-0.27%; p=0.0001 for noninferiority). Similar results are observed in the FAS population. Far fewer patients experience investigator-defined, drug-related hypoglycemia with linagliptin than glimepiride (7.5% vs 36.1%; p<0.0001). Body weight is decreased with linagliptin and increased with glimepiride (−1.4 kg vs +1.3 kg; adjusted mean difference, −2.7 kg; p<0.0001). CV events occur in 13 (1.7%) linagliptin patients vs 26 (3.4%) glimepiride patients revealing a significant 50% reduction in relative risk for the combined CV endpoint (RR, 0.50; 95% CI, 0.26-0.96; p=0.04). In conclusion, when added to metformin monotherapy, linagliptin provides similar HbA1c reductions to glimepiride but with less hypoglycemia, relative weight loss, and significantly fewer adjudicated CV events.

Cardiovascular Risk with Linagliptin in Patients with Type 2 Diabetes: A Pre-Specified, Prospective, and Adjudicated Meta-Analysis from a Large Phase III Program:

The cardiovascular (CV) benefit of glucose lowering, particularly if too intensive, in type 2 diabetes mellitus (T2DM) is currently debated. Some modalities have even been reported, unexpectedly, to be associated with worse CV outcomes.

TABLE

Effect of linagliptin on body weight total body fat, liver fat and intramyocellular fat

| | Body weight | | Total body fat | | Liver fat | | Intra-myocellular fat | |
| --- | --- | --- | --- | --- | --- | --- | --- | --- |
| | % contr. | % baseli. | % contr. | % baseli. | % contr. | % baseli. | % contr. | % baseli. |
| Control | — | +15% | — | +11% | — | +27% | — | +23% |
| | | p = 0.016 | | p = 0.001 | | p = 0.09 | | p = 0.49 |
| Linagliptin | −3% | +12% | −5% | +5% | −39% | −30% | −36% | −24% |
| | p = 0.56 | p = 0.001 | p = 0.27 | p = 0.06 | p = 0.022 | p = 0.05 | p = 0.14 | p = 0.039 |
| Sibutramine | −12% | +1% | −12% | −0.4% | −30% | −29% | −55% | −34% |
| | p = 0.018 | p = 0.64 | p = 0.008 | p = 0.86 | p = 0.13 | p = 0.12 | p = 0.037 | p = 0.007 |

Linagliptin is the first once-daily DPP-4 inhibitor available as one dose without the need for dose adjustment for declining renal function. Linagliptin achieves glycemic control without weight gain or increased hypoglycemic risk that may translate into CV benefits. To investigate the CV profile of the DPP-4 inhibitor linagliptin, a pre-specified meta-analysis of all CV events from 8 phase III randomized, double blind, controlled trials (≥12 weeks) is conducted. CV events are prospectively adjudicated by a blinded independent expert committee. The primary endpoint of this analysis is a composite of CV death, non-fatal stroke, non-fatal myocardial infarction (MI), and hospitalization for unstable angina pectoris (UAP). Other secondary and tertiary CV endpoints are also assessed, including FDA-custom major adverse CV events (MACE).

Of 5239 patients included (mean baseline $HbA_{1c}$ 8.0%) 3319 receive linagliptin once daily (5 mg: 3159, 10 mg: 160) and 1920 comparator (placebo: 977, glimepiride: 781, voglibose: 162). Cumulative exposure (person yrs) is 2060 for linagliptin and 1372 for comparators. Overall, adjudicated primary CV events occurred in 11 (0.3%) patients receiving linagliptin and 23 (1.2%) receiving comparator. The hazard ratio for the primary endpoint is significantly lower for linagliptin vs comparator and hazard ratios are similar or significantly lower with linagliptin vs comparator for all other CV endpoints (TABLE).

This is the first pre-specified, prospective, and independently adjudicated CV meta-analysis of a DPP-4 inhibitor in a large Phase III program. Although a meta-analysis, with distinct limitations, the data support a potential reduction of CV events with linagliptin.

TABLE

|  | Linagliptin (n = 3319) | Comparator (n = 1920) | Hazard ratio (Cox proportional model) (95% CI) |
|---|---|---|---|
| Primary CV endpoint, n (%) | 11 (0.3) | 23 (1.2) |  |
| incidence rate/1000 pt-yr | 5.3 | 16.8 | 0.34 (0.16, 0.70)* |
| Secondary CV endpoints, incidence rate/1000 pt-yr |  |  |  |
| CV death, stroke, or MI | 4.8 | 14.6 | 0.36 (0.17, 0.78)* |
| All adjudicated CV events | 12.6 | 23.4 | 0.55 (0.33, 0.94)* |
| FDA-custom MACE | 4.3 | 13.9 | 0.34 (0.15, 0.75)* |
| Tertiary CV endpoints, incidence rate/1000 pt-yr |  |  |  |
| CV death | 1.0 | 1.5 | 0.74 (0.10, 5.33) |
| Non-fatal MI | 2.9 | 5.1 | 0.52 (0.17, 1.54) |
| Non-fatal stroke | 1.0 | 8.0 | 0.11 (0.02, 0.51)* |
| Transient ischemic attack | 0.5 | 2.9 | 0.17 (0.02, 1.53) |
| Hospitalization for UAP | 0.5 | 2.2 | 0.24 (0.02, 2.34) |

*Significant lower Hazard ratio (upper 95% CI < 1.0; p < 0.05).

Treatment of Patients with Type 2 Diabetes Mellitus at High Cardiovascular Risk

The longterm impact on cardiovascular morbidity and mortality and relevant efficacy parameters (e.g. HbA1c, fasting plasma glucose, treatment sustainability) of treatment with linagliptin in a relevant population of patients with type 2 diabetes mellitus is investigated as follows:

Type 2 diabetes patient with insufficient glycemic control (naïve or currently treated (mono or dual therapy) with e.g. metformin and/or an alpha-glucosidase inhibitor (e.g. having HbA1c 6.5-8.5%), or currently treated (mono or dual therapy) with e.g. a sulphonylurea or glinide, with or without metformin or an alpha-glucosidase inhibitor (e.g. having HbA1c 7.5-8.5%)) and high risk of cardiovascular events, e.g. defined as one or more of risk factors A), B), C) and D) indicated below, are treated over a lengthy period (e.g. for >/=2 years, 4-5 years or 1-6 years) with linagliptin (optionally in combination with one or more other active substances, e.g. such as those described herein) and compared with patients who have been treated with other antidiabetic medicaments (e.g. a sulphonylurea, such as glimepiride) or with placebo. Evidence of the therapeutic success compared with patients who have been treated with other antidiabetic medicaments or with placebo can be found in the smaller number of single or multiple complications (e.g. cardio- or cerebrovascular events such as cardiovascular death, myocardial infarction, stroke, or hospitalization (e.g. for acute coronary syndrome, leg amputation, urgent revascularization procedures or for unstable angina pectoris), or, preferably, in the longer time taken to first occurrence of such complications, e.g. time to first occurrence of any of the following components of the primary composite endpoint: cardiovascular death, non-fatal myocardial infarction, non-fatal stroke and hospitalization for unstable angina pectoris.

Additional therapeutic success can be found in greater proportion of patients on study treatment at study end maintain glycemic control (e.g. HbA1c</=7%) without need of rescue medication and without weight gain (e.g. >/=2%). Further additional therapeutic success can be found in greater proportion of patients on study treatment at study end maintain glycemic control (e.g. HbA1c</=7%) without need of rescue medication and without moderate/severe hypoglycemic episodes and without weight gain (e.g. >/=2%).

Further therapeutic success can be found e.g. in CV superiority of treatment with linagliptin versus treatment with glimepiride (each optionally as monotherapy or as add-on therapy to metformin or an alpha-glucosidase inhibitor) with a risk reduction of preferably about 20%, for example.

Risk factors A), B), C) and D) for cardiovascular events:
A) Previous vascular disease (e.g. age 40-85 years):
 myocardial infarction (e.g. >=6 weeks),
 coronary artery disease (e.g. >=50% luminal diameter narrowing of left main coronary artery or in at least two major coronary arteries in angiogram),
 percutaneous coronary intervention (e.g. >=6 weeks),
 coronary artery by-pass grafting (e.g. >=4 years or with recurrent angina following surgery),
 ischemic or hemorrhagic stroke (e.g. >=3 months),
 peripheral occlusive arterial disease (e.g. previous limb bypass surgery or percutaneous transluminal angioplasty; previous limb or foot amputation due to circulatory insufficiency, angiographic or ultrasound detected significant vessel stenosis (>50%) of major limb arteries (common iliac artery, internal iliac artery, external iliac artery, femoral artery, popliteal artery), history of intermittent claudication, with an ankle: arm blood pressure ratio <0.90 on at least one side),
B) Vascular related end-organ damage (e.g. age 40-85 years):
 impaired renal function (e.g. moderately impaired renal function as defined by MDRD formula, with eGFRF 30-59 mL/min/1.73 m2),
 micro- or macroalbuminuria (e.g. microalbuminuria, or random spot urinary albumin:creatinine ratio >/=30 μg/mg),
 retinopathy (e.g. proliferative retinopathy, or retinal neovascularisation or previous retinal laser coagulation therapy), C) Elderly (e.g. age >/=70 years),
D) At least two of the following cardiovascular risk factors (e.g. age 40-85 years):
   advanced type 2 diabetes mellitus (e.g. >10 years duration),
   hypertension (e.g. systolic blood pressure >140 mmHg or on at least one blood pressure lowering treatment),
   current daily cigarette smoking,
   (atherogenic) dyslipidemia or high LDL cholesterol blood levels (e.g. LDL cholesterol >/=135 mg/dL) or on at least one treatment for lipid abnormality,
   (visceral and/or abdominal) obesity (e.g. body mass index >/=45 kg/m2),
   age >/=40 and </=80 years.

Beneficial effects (e.g. improvement) on cognitive function (e.g. cognitive decline, changes in psychomotor speed, psychological well-being), β-cell function (e.g. insulin secretion rate derived from a 3 h meal tolerance test, long term β-cell function), renal function parameters, diurnal glucose pattern (e.g. ambulatory glucose profile, glycemic variability, biomarkers of oxidation, inflammation and endothelial function, cognition and CV morbidity/mortality), silent MI (e.g. ECG parameters, CV prophylactic properties), LADA (e.g. use of rescue therapy or disease progression in LADA) and/or durability of glucose control according to β-cell autoantibody status (e.g., GAD) of treatment with linagliptin is investigated in substudies.

The invention claimed is:

1. A method for treating oxidative stress, vascular stress and/or endothelial dysfunction in a sepsis patient in need thereof, the method comprising administering linagliptin to the patient.

2. The method of claim 1, wherein the sepsis patient is a diabetic patient or a nondiabetic patient.

3. A method for treating sepsis comprising administering linagliptin to a patient in need thereof.

4. The method of claim 3, wherein the linagliptin is administered orally to the patient.

5. The method of claim 3, wherein the linagliptin is administered intravenously to the patient.

* * * * *